US008680246B2

(12) United States Patent
McCauley et al.

(10) Patent No.: US 8,680,246 B2
(45) Date of Patent: Mar. 25, 2014

(54) ANTIBODIES THAT BIND TO LYSYL OXIDASE-LIKE 2 (LOXL2)

(75) Inventors: Scott Alan McCauley, Brisbane, CA (US); Hector Rodriguez, Brisbane, CA (US); Carlos Aurelio Garcia, San Lorenzo, CA (US); Victoria Smith, Burlingame, CA (US)

(73) Assignee: Gilead Biologics, Inc., Foster City, CA (US)

( * ) Notice: Subject to any disclaimer, the term of this patent is extended or adjusted under 35 U.S.C. 154(b) by 273 days.

(21) Appl. No.: 13/021,555

(22) Filed: Feb. 4, 2011

(65) Prior Publication Data
US 2011/0200606 A1 Aug. 18, 2011

Related U.S. Application Data

(60) Provisional application No. 61/301,550, filed on Feb. 4, 2010.

(51) Int. Cl.
C07K 16/40 (2006.01)
C07K 16/00 (2006.01)

(52) U.S. Cl.
USPC ............... 530/388.26; 530/388.1; 530/387.3; 530/387.1; 435/810

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,485,088 A | 11/1984 | Chvapil |
| 4,545,382 A | 10/1985 | Higgins et al. |
| 4,637,403 A | 1/1987 | Barcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagan et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Paifreyman et al. |
| 5,120,764 A | 6/1992 | McCarthy et al. |
| 5,182,297 A | 1/1993 | Paifreyman et al. |
| 5,192,659 A | 3/1993 | Simons |
| 5,252,608 A | 10/1993 | Paifreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,625,126 A | 4/1997 | Lonberg et al. |
| 5,633,425 A | 5/1997 | Lonberg et al. |
| 5,641,484 A | 6/1997 | Hung et al. |
| 5,661,016 A | 8/1997 | Lonberg et al. |
| 5,721,138 A | 2/1998 | Lawn |
| 6,015,562 A | 1/2000 | Hinman et al. |
| 6,140,056 A | 10/2000 | Khodadoust |
| 6,225,118 B1 | 5/2001 | Grant et al. |
| 6,277,622 B1 | 8/2001 | Weiss |
| 6,300,092 B1 | 10/2001 | Khodadoust et al. |
| 6,303,318 B1 | 10/2001 | O'Brien |
| 6,316,416 B1 | 11/2001 | Patierno et al. |
| 6,326,174 B1 | 12/2001 | Joyce et al. |
| 6,391,602 B1 | 5/2002 | Khodadoust |
| 6,534,261 B1 | 3/2003 | Cox, III et al. |
| 6,808,707 B2 | 10/2004 | Ensley |
| 7,112,668 B2 | 9/2006 | Rastelli et al. |

(Continued)

FOREIGN PATENT DOCUMENTS

EP 0186087 8/1989
EP 0375408 6/1990

(Continued)

OTHER PUBLICATIONS

Campbell (Monoclonal Antibody Technology, 1984, Chapter 1, pp. 1-32).*
Harris et al. (1974) "Connective Tissue Amine Oxidase. II. Purification and Partial Characterization of Lysyl Oxidase from Chick Aorta" *Biochim. Biophys. Acta* 341(2):332-344.
Harrison & Lazo (1987) "High Dose Continuous Infusion of Bleomycin in Mice: A New Model for Drug-Induced Pulmonary Fibrosis" *J. Pharmacol. Exp. Ther.* 243(3):1185-1194.
Hohenester et al. (1999) "Crystal Structure of a Scavenger Receptor Cysteine-Rich Domain Sheds Light on an Ancient Superfamily" *Nat. Struct. Biol.* 6(3):228-232.
Ito et al. (2001) "Molecular Cloning and Biological Activity of a Novel Lysyl Oxidase-Related Gene Expressed in Cartilage" *J. Biol. Chem.* 276(26):24023-24029.

(Continued)

Primary Examiner — Sharon Wen
(74) Attorney, Agent, or Firm — Yu-Ming Dammann

(57) ABSTRACT

The present disclosure provides lysyl oxidase-like-2 (LOXL2) polypeptide binding agents, including, for example, antibodies that specifically bind a LOXL2 polypeptide; and further provides compositions comprising same. The binding agents can be used in various treatment and diagnostic methods, which are also provided.

27 Claims, 7 Drawing Sheets

(56) References Cited

U.S. PATENT DOCUMENTS

| | | |
|---|---|---|
| 7,208,300 B2 | 4/2007 | Evans et al. |
| 7,255,856 B2 | 8/2007 | Li et al. |
| 7,255,857 B2 | 8/2007 | Li et al. |
| 7,335,294 B2 | 2/2008 | Heller et al. |
| 7,348,170 B2 | 3/2008 | Yuuki et al. |
| 7,396,920 B2 | 7/2008 | Hemmings et al. |
| 7,445,920 B2 | 11/2008 | Evans et al. |
| 7,585,634 B2 | 9/2009 | Kim et al. |
| 8,163,494 B2 | 4/2012 | Neufeld et al. |
| 8,168,180 B2 | 5/2012 | Neufeld et al. |
| 8,461,303 B2 * | 6/2013 | Smith et al. ............... 530/387.1 |
| 2001/0005581 A1 | 6/2001 | Grant et al. |
| 2001/0012890 A1 | 8/2001 | Thompson |
| 2002/0072089 A1 | 6/2002 | Holtzman et al. |
| 2002/0123476 A1 | 9/2002 | Emanuele et al. |
| 2002/0128218 A1 | 9/2002 | Emanuele et al. |
| 2002/0151007 A1 | 10/2002 | Khodadoust et al. |
| 2002/0156263 A1 | 10/2002 | Chen |
| 2003/0008023 A1 | 1/2003 | Lu |
| 2003/0017068 A1 | 1/2003 | Larrain et al. |
| 2003/0092037 A1 | 5/2003 | Matsuzaki et al. |
| 2003/0096980 A1 | 5/2003 | Froehler et al. |
| 2003/0099213 A1 | 5/2003 | Lee et al. |
| 2003/0114410 A1 | 6/2003 | Neufeld et al. |
| 2003/0129672 A1 | 7/2003 | Dyer et al. |
| 2003/0149997 A1 | 8/2003 | Hageman |
| 2003/0152926 A1 | 8/2003 | Murray et al. |
| 2003/0211076 A1 | 11/2003 | Li et al. |
| 2004/0009154 A1 | 1/2004 | Khan et al. |
| 2004/0029114 A1 | 2/2004 | Mack et al. |
| 2004/0156854 A1 | 8/2004 | Mulligan et al. |
| 2004/0171110 A1 | 9/2004 | Evans et al. |
| 2004/0176296 A1 | 9/2004 | Holtzman et al. |
| 2004/0197328 A1 | 10/2004 | Young et al. |
| 2004/0213756 A1 | 10/2004 | Michal et al. |
| 2004/0248871 A1 | 12/2004 | Farjanel et al. |
| 2004/0253220 A1 | 12/2004 | Perrier et al. |
| 2004/0253606 A1 | 12/2004 | Aziz et al. |
| 2004/0258676 A1 | 12/2004 | Perrier et al. |
| 2004/0265230 A1 | 12/2004 | Martinez et al. |
| 2005/0020521 A1 | 1/2005 | Rana et al. |
| 2005/0079538 A1 | 4/2005 | Griffin et al. |
| 2005/0119202 A1 | 6/2005 | Kreutzer et al. |
| 2005/0181375 A1 | 8/2005 | Aziz et al. |
| 2005/0259483 A1 | 11/2005 | Nakamura et al. |
| 2005/0260639 A1 | 11/2005 | Nakamura et al. |
| 2006/0019256 A1 | 1/2006 | Clarke et al. |
| 2006/0088532 A1 | 4/2006 | Alitalo et al. |
| 2006/0088882 A1 | 4/2006 | Jain et al. |
| 2006/0127402 A1 | 6/2006 | Neufeld et al. |
| 2006/0127902 A1 | 6/2006 | Madden et al. |
| 2006/0134172 A1 | 6/2006 | Shepard et al. |
| 2006/0134801 A1 | 6/2006 | Chada et al. |
| 2006/0216722 A1 | 9/2006 | Betholtz et al. |
| 2006/0223760 A1 | 10/2006 | Li et al. |
| 2007/0010469 A1 | 1/2007 | Chan et al. |
| 2007/0021365 A1 | 1/2007 | Erler et al. |
| 2007/0037203 A1 | 2/2007 | Kapeller-Libermann |
| 2007/0054278 A1 | 3/2007 | Cargill |
| 2007/0059745 A1 | 3/2007 | Sharp et al. |
| 2007/0148173 A1 | 6/2007 | Huang et al. |
| 2007/0154481 A1 | 7/2007 | Gelinas et al. |
| 2007/0184439 A1 | 8/2007 | Guilford et al. |
| 2007/0197424 A1 | 8/2007 | Friedman et al. |
| 2007/0225242 A1 | 9/2007 | Erler et al. |
| 2007/0231323 A1 | 10/2007 | Phillips |
| 2007/0243214 A1 | 10/2007 | Schiemann et al. |
| 2008/0031817 A1 | 2/2008 | Mazar et al. |
| 2008/0118928 A1 | 5/2008 | Hageman |
| 2008/0137893 A1 | 6/2008 | Ross et al. |
| 2008/0181896 A1 | 7/2008 | Khan et al. |
| 2008/0187523 A1 | 8/2008 | Zhang et al. |
| 2008/0220424 A1 | 9/2008 | Haber et al. |
| 2008/0248477 A1 | 10/2008 | Holtzman et al. |
| 2008/0261870 A1 | 10/2008 | Trackman et al. |
| 2008/0274453 A1 | 11/2008 | Hageman |
| 2008/0279857 A1 | 11/2008 | Skerry et al. |
| 2008/0286808 A1 | 11/2008 | Schellenberger et al. |
| 2008/0292547 A1 | 11/2008 | Tolleshaug et al. |
| 2008/0305965 A1 | 12/2008 | Moorhouse et al. |
| 2009/0022703 A1 | 1/2009 | Li et al. |
| 2009/0023149 A1 | 1/2009 | Knudsen et al. |
| 2009/0035348 A1 | 2/2009 | Zadini et al. |
| 2009/0053224 A1 | 2/2009 | Smith et al. |
| 2009/0104201 A1 | 4/2009 | Smith et al. |
| 2009/0142301 A1 | 6/2009 | Bevec et al. |
| 2009/0232773 A1 | 9/2009 | Kato et al. |
| 2009/0233270 A9 | 9/2009 | St. Croix et al. |
| 2009/0239947 A1 | 9/2009 | Dai et al. |
| 2009/0275633 A1 | 11/2009 | Esteller |
| 2010/0119515 A1 | 5/2010 | Neufeld et al. |
| 2010/0144603 A1 | 6/2010 | Watnick |
| 2010/0203062 A1 | 8/2010 | Stalmans et al. |
| 2010/0209415 A1 | 8/2010 | Smith et al. |
| 2010/0317721 A1 | 12/2010 | Neufeld |
| 2011/0044907 A1 | 2/2011 | Marshall et al. |
| 2011/0044981 A1 | 2/2011 | Spangler et al. |
| 2011/0076272 A1 | 3/2011 | Smith et al. |
| 2011/0076285 A1 | 3/2011 | Stalmans et al. |
| 2011/0076739 A1 | 3/2011 | McCauley et al. |
| 2011/0207144 A1 | 8/2011 | Marshall et al. |
| 2012/0087917 A1 | 4/2012 | Smith et al. |
| 2012/0165398 A1 | 6/2012 | Neufeld et al. |
| 2012/0202206 A1 | 8/2012 | Neufeld et al. |
| 2012/0309020 A1 | 12/2012 | Smith et al. |
| 2013/0017207 A1 | 1/2013 | Smith et al. |

FOREIGN PATENT DOCUMENTS

| | | |
|---|---|---|
| EP | 0799891 | 10/1997 |
| EP | 0960192 | 12/1999 |
| EP | 1149169 | 10/2001 |
| EP | 1616881 | 1/2006 |
| EP | 1690932 | 8/2006 |
| EP | 1693448 | 8/2006 |
| EP | 1715035 | 10/2006 |
| EP | 2078531 | 7/2009 |
| WO | WO 8912060 | 12/1989 |
| WO | WO 9220702 | 11/1992 |
| WO | WO 9600614 | 1/1996 |
| WO | WO 9640746 | 12/1996 |
| WO | WO 9700441 | 1/1997 |
| WO | WO 9806830 | 2/1998 |
| WO | WO 9965928 | 12/1999 |
| WO | WO 0044910 | 8/2000 |
| WO | WO 0183702 | 11/2001 |
| WO | WO 0192495 | 12/2001 |
| WO | WO 0211667 | 2/2002 |
| WO | WO 02061092 | 8/2002 |
| WO | WO 02079492 | 10/2002 |
| WO | WO 02086443 | 10/2002 |
| WO | WO 03031939 | 4/2003 |
| WO | WO 03100016 | 12/2003 |
| WO | WO 2004023973 | 3/2004 |
| WO | WO 2004047720 | 6/2004 |
| WO | WO-2004/061423 | 7/2004 |
| WO | WO 2004091655 | 10/2004 |
| WO | WO 2005100604 | 10/2005 |
| WO | WO 2006128740 | 12/2006 |
| WO | WO 2007045927 | 4/2007 |
| WO | WO 2007126457 | 11/2007 |
| WO | WO 2008063479 | 5/2008 |
| WO | WO 2008070616 | 6/2008 |
| WO | WO 2008132453 | 11/2008 |
| WO | WO 2008138578 | 11/2008 |
| WO | WO 2009010974 | 1/2009 |
| WO | WO-2009017833 | 2/2009 |
| WO | WO 2009035791 | 3/2009 |
| WO | WO-2010080769 | 7/2010 |
| WO | WO-2010091279 | 8/2010 |
| WO | WO-2011022667 | 2/2011 |
| WO | WO-2011022670 | 2/2011 |
| WO | WO-2011022706 | 2/2011 |
| WO | WO-2011022709 | 2/2011 |

(56) References Cited

FOREIGN PATENT DOCUMENTS

| WO | WO-2011022710 | 2/2011 |
|---|---|---|
| WO | WO-2011041309 | 4/2011 |
| WO | WO-2011097513 | 8/2011 |
| WO | WO-2012/139045 | 10/2012 |
| WO | WO-2012/167181 | 12/2012 |

OTHER PUBLICATIONS

Molnar et al. (2003) "Structural and functional diversity of lysyl oxidase and the LOX-like proteins" *Biochim Biophys Acta.* 1647(1-2):220-224.

Rayton et al. (1979) "Induction of Lysyl Oxidase with Copper. Properties of an In Vitro System" *J. Biol. Chem.* 254(3):621-626.

Sasaki et al. (1998) "Mac-2 Binding Protein is a Cell-Adhesive Protein of the Extracellular Matrix Which Self-Assembles into Ring-Like Structures and Binds β1 Integrins, Collagens and Fibronectin" *EMBO J.* 17(6):1606-1613.

Stassen (1976) "Properties of Highly Purified Lysyl Oxidase from Embryonic Chick Cartilage" *Biophys. Acta* 438(1):49-60.

Walters & Kleeberger (2008) "Mouse Models of Bleomycin-Induced Pulmonary Fibrosis" *Current Protocols Pharmacol.* 40:5.46.1-5.46.17.

U.S. Appl. No. 12/860,632, filed Aug. 20, 2010, Marshall, et al.

"The role of the Extracellular Matrix in Cancer" Mar. 2001, U.S. Department of Energy: http:www.science.doe.gov/Accomplishments_Awards/Decades_Discovery/85.html.

Adamson, et al. (1974) "The Pathogenesis of Bleomycin-Induced Pulmonary Fibrosis in Mice" Am. J. Pathol. 77(2):185-189.

Akagawa, et al. (2007). "Systematic screening of lysyl oxidase-like (LOXL) family genes demonstrates that LOXL2 is a susceptibility gene to intracranial aneurysms." Hum Genet 121(3-4): 377-87.

Akiri et al. (2003) "Lysyl Oxidase-Related Protein-1 Promotes Tumor Fibrosis and Tumor Progression in Vivo" *Cancer Res.* 63(7):1657-1666.

Albini et al. (1987) "A Rapid In Vitro Assay for Quantitating the Invasive Potential of Tumor Cells" *Cancer Res.* 47(12):3239-3245.

Arguello et al. (1992) "Incidence and Distribution of Experimental Metastases in Mutant Mice with Defective Organ Microenvironments (Genotypes Sl/Sld and W/Wv)" *Cancer Research* 52(8):2304-2309.

Asuncion et al. (2001) "A Novel Human Lysyl Oxidase-Like Gene (LOXL4) on Chromosome 10q24 Has an Altered Scavenger Receptor Cysteine Rich Domain" *Matrix Biol.* 20(7):487-491.

Atabani, et al. (1997) "Identification of an Immunodominant Neutralizing and Protective Epitope from Measles Virus Fusion Protein by Using Human Sera from Acute Infection" *J. Virology* 71(10):7240-7245.

Atsawasuwan, et al. (2005). "Expression of lysyl oxidase isoforms in MC3T3-E1 osteoblastic cells." Biochem Biophys Res Commun 327(4): 1042-6.

Atsawasuwan, et al. (2008). "Lysyl oxidase binds transforming growth factor-β and regulates its signaling via amine oxidase activity." J Biol Chem 283(49): 34229-40.

Auerbach et al. (2003) "Angiogenesis Assays: A Critical Overview" *Clinical Chemistry* 49(1):32-40.

Barker, et al. (2011) "LOXL2-mediated matrix remodeling in metastasis and mammary gland involution" Cancer Res., 71(5):1561-1572.

Barry-Hamilton, et al. (2010) "Allosteric inhibition of lysyl oxidase-like-2 impedes the development of a pathologic microenvironment" Nat.Med., 19(9):1009-1017.

Barzu, et al. "Characterization of B-Cell Epitopes on IpaB, an Invasion-Associated Antigen of *Shigella flexneri*: Identification of an Immunodominant Domain Recognized during Natural Infection" Infection and Immunity, Sep. 1993, vol. 61, No. 9, pp. 3825-3831.

Bendig (1995) "Humanization of Rodent Monoclonal Antibodies by CDR Grafting" Methods: Companion to Methods in Enzymology 8:83-93.

Berithaupt, et al. (2008) "Demyelinating Myelin Oligodendrocyte Glycoprotein-Specific Autoantibody Response Is Focused on one Dominant Conformational Epitope Region in Rodents" J. Immunology 181(2):1255-1263.

Betakova, et al. (1998) "Monoclonal Anti-Idiotypic Antibodies Mimicking the Immunodominant Epitope of Influenza Virus Haemagglutinin Elicit Biologically Significant Immune Responses" J. Gen. Virology 79(Pt.3):461-470.

Bhowmick, et al. (2004). "Stromal fibroblasts in cancer initiation and progression." Nature 432(7015): 332-7.

Boneberg, et. al. (2009) "Angiogenesis and lymphangiogenesis are downregulated in primary breast cancer" Br. J. Cancer, 101(4):605-614.

Borel et al. (2001) "Lysyl Oxidase-Like Protein from Bovine Aorta. Isolation and Maturation to an Active Form by Bone Morphogenetic Protein-1" *J. Biol. Chem.*276(52):48944-48949.

Bouez, et al. (2006) "The Lysyl Oxidase LOX is Absent in Basal and Squamous Cell Carcinomas and its Knockdown Induces an Invading Phenotype in a Skin Equivalent Model" Clinical Cancer Res. 12(5) 1463-1469.

Brody, et al. (1976) "Lung lysyl oxidase and elastin synthesis during compensatory lung growth" *Chest* 69(2 Suppl):271-272.

Bronson et al. (2005) "LOXL Null Mice Demonstrate Selective Dentate Structural Changes but Maintain Dentate Granule Cell and CAl Pyramidal Cell Potentiation in the Hippocampus" *Neurosci. Lett.* 390(2):118-122.

Brown, et al. (2004) "Exploiting Tumour Hypoxia in Cancer Treatment" Nature Reviews 4:437-447.

Brukamp, et al. (2007) "Hypoxia and Podocyte-Specific Vhlh Deletion Confer Risk of Glomerular Disease" Am. J. Physiol. Renal. Physiol. 293(4):F1397-F1407.

Bruns, et al. "Vascular Endothelial Growth Factor Is an In Vivo Survival Factor for Tumor Endothelium in a Murine Model of Colorectal Carcinoma Liver Metastases" *Cancer*, 2000 vol. 89, No. 3, pp. 488-499.

Burbelo, et al. (1986) "Monoclonal Antibodies to Human Lysyl Oxidase" Coll. Relat. Res. 6(2):153-62.

Butcher, et al. (2009) "A Tense Situation: Forcing Tumour Progression" Nat. Rev. Cancer 9(2):108-122.

Cairns, et al. (2004) "Acute Hypoxia Enhances Spontaneous Lymph Node Metastasis in an Orthotopic Murine Model of Human cervical Carcinoma" Cancer Res. 64:2054-2061.

Cancer Reference Information; Detailed guide: Breast cancer, how is breast cancer diagnosed? www.cancer.org/docroot/CRI_2_4_3X_How_is_breast_cancer_diagnosed, Nov. 16, 2009.

Cardone, et al. (1997). "Prognostic value of desmoplastic reaction and lymphocytic infiltration in the management of breast cancer." Panminerva Med 39(3): 174-7.

Chan, et al. (2007) "Hypoxia, Gene Expression, and Metastasis" Cancer Metastasis Rev. 26(2):333-339.

Chang & Werb (2001) "The Many Faces of Metalloproteases: Cell Growth, Invasion, Angiogenesis and Metastasis" Trends Cell. Biol. 11(11):S37-43.

Chang, et al. (2004) "Gene expression signature of fibroblast serum response predicts human cancer progression: similarities between tumors and wounds" PLoS Biol. 2(2):206-213.

Chanoki, et al. (1995) "Increased Expression of Lysyl Oxidase in Skin with Scleroderma" Br. J. Dermatol. 133(5):710-5.

Chichester, et al. (1981). "Lung lysyl oxidase and prolyl hydroxylase: increases induced by cadmium chloride inhalation and the effect of β-aminopropionitrile in rats." Am Rev Respir Dis 124(6): 709-13.

Chioza, et al. (2001). "Mutations in the lysyl oxidase gene are not associated with amyotrophic lateral sclerosis." Amyotroph Lateral Scler Other Motor Neuron Disord 2(2): 93-7.

Chow, et al. "Identification and Expression of an Allergen Asp f 13 from *Aspergillus fumigatus* and Epitope Mapping Using Human IgE Antibodies and Rabbit Polyclonal Antibodies," Biochem. J, 2000, vol. 346, pp. 423-431.

Christiansen & Rajasekaran (2006) "Reassessing Epithelial to Mesenchymal Transition as a Prerequisite for Carcinoma Invasion and Metastasis" Cancer Res., 66(17):8319-26.

(56) References Cited

OTHER PUBLICATIONS

Christiansen, et al. (2004) "Biological Impediments to Monoclonal Antibody-Based Cancer Immunotherapy" Mol. Cancer Ther. 3(11):1493-1501.
Chu & Peters (2008). "Serial analysis of the vascular endothelial transcriptome under static and shear stress conditions." Physiol Genomics 34(2): 185-92.
Chu, et al. (2008). "Glycogen synthase kinase-3β regulates DeltaNp63 gene transcription through the β-catenin signaling pathway." J Cell Biochem 105(2): 447-53.
Colman (1994) "Effects of Amino Acid Sequence Changes on Antibody-Antigen Interactions" Res. Immunol. 145(1):33-36.
Conti, et al. (2008). "The desmoplastic reaction surrounding hepatic colorectal adenocarcinoma metastases aids tumor growth and survival via alphav integrin ligation." Clin Cancer Res 14(20):6405-13.
Csiszar (2001) "Lysyl Oxidases: a Novel Multifunctional Amine Oxidase Family" Prog. Nucl. Acid Res. 70:1-32.
Csiszar, et al. (1996). "Functional analysis of the promoter and first intron of the human lysyl oxidase gene." Mol Biol Rep 23(2): 97-108.
Csiszar, et al. (2002) "Somatic Mutation of the Lysyl Oxidase Gene on Chromosome 5q23.1 in Colorectal Tumors" Int. J. Cancer 97(5):636-642.
Database Geneseq (Derwent, London, UK), Accession No. A 13B07649, Feb. 14, 2002, 99.9% identical to SEQ ID No. 2.
Database Issued Patents (United States Patent & Trademark Office, Alexandria, VA) US Patent No. 6,300,092. Oct. 9, 2001 99.9% identical to SEQ ID No. 2.
Decitre, et al. (1998) "Lysyl oxidase-like protein localizes to sites of de novo fibrinogenesis in fibrosis and in the early stromal reaction of ductal breast carcinomas" Lab. Invest. 78(2):143-151.
Denko, et al. (2003) "Investigating Hypoxic Tumor Physiology through Gene Expression Patterns" Oncogene 22:5907-5914.
Dermer (1994) "Another Anniversary for the War on Cancer" Biotechnology 12:320.
Dillman, (1989) "Monoclonal antibodies for treating cancer" Ann. Intern. Med. 111(7):592-603.
Entrez Gene data base searching result in National Library of Medicine. 2010.
Erler & Giaccia (2006). "Lysyl oxidase mediates hypoxic control of metastasis." Cancer Res 66(21): 10238-41.
Erler, et al. (2004) "627 The role of Hypoxia-Induced Lysyl Oxidase in Cancer Progression, Tumor Response to Therapy and Patient Prognosis" Eur. J. Cancer Suppl. 2(8):190.
Erler, et al. (2004) "Lysyl Oxidase is Essential for Hypoxia-Induced Metastasis" Pro. Amer. Assoc. Cancer Res. 47:570.
Erler, et al. (2005) "Hypoxia promotes invasion and metastasis of breast cancer cells by increasing lysyl oxidase expression" Breast Cancer Res. 7 (Suppl 2):P5.05.
Erler, et al. (2006) "12 LOX is Essential for Hypoxia-Induced Metastasis" Radiother. Oncol. 78:S5.
Erler, et al. (2006) "Lysyl Oxidase is Essential for Hypoxia-Induced Metastasis" Nature 440(7088):1222-1226.
Erler, et al. (2009). "Hypoxia-induced lysyl oxidase is a Critical mediator of bone marrow cell recruitment to form the premetastatic niche." Cancer Cell 15(1): 35-44.
Evans et al. (1999) "Vaccine Therapy for Cancer—Fact or Fiction?" QJM. 92(6):299-307.
Example from Wikipedia, the free encyclopedia, "Monoclonal Antibody Therapy," (http://en.wikipedia.org/wiki/Antibody_therapy), accessed on Oct. 4, 2010.
Example of the USPTO's Written Description Training Materials, Revision 1, Mar. 25, 2008, 84 pages in length.
Ferrari, et al. (1991) "Identification of Immunodominant T Cell Epitopes of the Hepatitis B Virus Nucleocapsid Antigen" J. Clin. Invest. 88(1):214-222.
Fidler, et al. (1994) "The implications of angiogenesis for the biology and therapy of cancer metastasis" Cell 79(2):185-188.
Fodstad, et al. (1988) "A New Experimental Metastasis Model in Athymic Nude Mice, the Human Malignant Melanoma Lox" Intl. J. Cancer 41:442-449.A216.

Fogelgren, et al. (2005) "Cellular fibronectin binds to lysyl oxidase with high affinity and is critical for its proteolytic activation" J Biol. Chem. 280(26):24690-24697.
Fong, et al. (2007) "Lysyl oxidase-like 2 expression is increased in colon and esophageal tumors and associated with less differentiated colon tumors" Genes, Chromosomes and Cancer vol. 46(7):644-655.
Freshney (1983) Culture of Animal Cells: A Manual of Basic Technique, Alan R. Liss Inc.: NY:4.
Gacheru, et al. (1997). "Transcriptional and post-transcriptional control of lysyl oxidase expression in vascular smooth muscle cells: effects of TGF-β1 and serum deprivation." J Cell Biochem 65(3): 395-407.
GenBank Accession No. AAA59525.1 "Lysyl Oxidase [*Homo sapiens*]".
GenBank Accession No. AAA59541.1 "Lysyl Oxidase [*Homo sapiens*]".
GenBank Accession No. AAB21243.1 "Lysyl Oxidase [*Homo sapiens*]".
GenBank Accession No. AAB23549.1 "Lysyl Oxidase [*Homo sapiens*]".
GenBank Accession No. AAD02130.1 "Lysyl Oxidase [*Homo sapiens*]".
GenBank Accession No. AAH15090.1 "Lysyl Oxidase-Like 1 [*Homo sapiens*]".
GenBank Accession No. AAH74820.1 "Lysyl Oxidase [*Homo sapiens*]".
GenBank Accession No. AAH74872.1 "Lysyl Oxidase [*Homo sapiens*]".
GenBank Accession No. AAK51671.1 "Lysyl Oxidase-Like 3 Protein [*Homo sapiens*]".
GenBank Accession No. AAK71934.1 "Lysyl Oxidase-Related Protein C [*Homo sapiens*]".
GenBank Accession No. AF039291 "*Homo sapiens* Lysyl Oxidase mRNA, Complete cds".
GenBank Accession No. AF282619 "*Homo sapiens* Lysyl Oxidase-like 3 Protein mRNA, Complete cds".
GenBank Accession No. AF338441 "*Homo sapiens* Lysyl Oxidase-Related Protein C (LOXC) mRNA, Complete cds".
GenBank Accession No. BC015090 "*Homo sapiens* Lysyl Oxidase-Like 1, mRNA (cDNA Clone MGC:16541 Image:4040510), Complete cds".
GenBank Accession No. BC018439 "*Mus musculus* Lysyl Oxidase, mRNA (cDNA Clone MGC:11525 Image:2655752), Complete cds".
GenBank Accession No. BC074820 "*Homo sapiens* Lysyl Oxidase, mRNA (cDNA Clone MGC:104085 Image:30915536), Complete cds".
GenBank Accession No. BC074872 "*Homo sapiens* Lysyl Oxidase, mRNA (cDNA Clone MGC:103851 Image:30915233), Complete cds".
GenBank Accession No. M84150 "Human Lysyl Oxidase Gene, Partial cds".
GenBank Accession No. M94054 "Human Lysyl Oxidase (LOX) mRNA, Complete cds".
GenBank Accession No. NM_002317 "*Homo sapiens* Lysyl Oxidase (LOX), Transcript Variant 1, mRNA".
GenBank Accession No. NM_033325 "*Mus musculus* Lysyl Oxidase-Like 2 (Lox12), mRNA".
GenBank Accession No. NP_002308 "Protein-Lysine 6-Oxidase Isoform 1 Preproprotein [*Homo sapiens*]".
GenBank Accession No. NP_002309 "Lysyl Oxidase Homolog 2 Precursor [*Homo sapiens*]".
GenBank Accession No. NP_005567 "Lysyl Oxidase Homolog 1 Preproprotein [*Homo sapiens*]".
GenBank Accession No. NP_034858 "Protein-Lysine 6-Oxidase Precursor [*Mus musculus*]".
GenBank Accession No. NP_034859 "Lysyl Oxidase Homolog 1 Precursor [*Mus musculus*]".
GenBank Accession No. NP_115587 "Lysyl Oxidase Homolog 4 Precursor [*Homo sapiens*]".
GenBank Accession No. NP_115882 "AP-1 Complex Subunit mu-1 Isoform 2 [*Homo sapiens*]".
GenBank Accession No. NP_201582 "Lysyl Oxidase homolog 2 Precursor [*Mus musculus*]".

(56) References Cited

OTHER PUBLICATIONS

GenBank Accession No. S45875 "Lysyl Oxidase [Human, Skin Fibroblasts, mRNA Partial, 1254 nt]".
GenBank Accession No. S78694 "Lysyl Oxidase [Human, mRNA, 1780 nt]".
GenBank Accession No. U89942 "Human Lysyl Oxidase-Related Protein (WS9-14) mRNA, Complete cds".
Giampuzzi et al. (2000) "Lysyl Oxidase Activates the Transcription Activity of Human Collagene III Promoter. Possible Involvement of Ku Antigen" *J. Biol. Chem.* 275(46):36341-36349.
Giampuzzi, et al. (2001) "Down-Regulation Oflysyloxidase-Induced Tumorigenic Transformation in NRK-49F Cells Characterized by Constitutive Activation of Ras Proto-Oncogene" J Biol. Chem. 276(31):29226-29232.
Görögh et al. (2007) "Selective Upregulation and Amplification of the Lysyl Oxidase Like-4 (LOXL4) Gene in Head and Neck Squamous cell Carcinoma" *J. Pathol.* 212(1):74-82.
Görögh, et al. (2008). "Functional analysis of the 5' flanking domain of the LOXL4 gene in head and neck squamous cell carcinoma cells." Int J Oncol 33(5): 1091-8.
Grant & Dent (2001) "Overview: Rational Integration of Agents Directed at Novel Therapeutic Targets into Combination Chemotherapeutic Regimens" *Curr. Opin. Investig Drugs* 2(11):1600-1605.
Gross, et al. (2001)"Idiopathic Pulmonary Fibrosis" N. Engl. J. Med. 345(7):517-525.
Gura (1997) "Systems for Identifying New Drugs Are Often Faulty" Science 278(5347):1041-1042.
Ham, et al. (2008) "144. Inhibition of an Extracellular Matrix Protein Increases Survival in Orthotopic Nude Mouse Models" J. Surg. Res. 144(2):239-240.
Hayashi, et al. (2004). "Comparative immunocytochemical localization of lysyl oxidase (LOX) and the lysyl oxidase-like (LOXL) proteins: changes in the expression of LOXL during development and growth of mouse tissues." J Mol Histol 35(8-9): 845-55.
Hein, et al. (2001). "Lysyl oxidases: expression in the fetal membranes and placenta." Placenta 22(1): 49-57.
Herrington et al., Principles and basic methodology of DNA/RNA detection by in situ hybridization. Chapter 4, pp. 69-102, Diagnostic Molecular Pathology vol. 1, Phenotyping and genotyping of intact cells, IRL Press, Oxford University Press, 1992.
Higgins, et al. (2007) "Hypoxia promotes a fibrogenesis in vivo via HIF-1 stimulation of epithelial-to-mesenchymal transition" Journal Clinical Investigation 117(12):3810-20.
Hockel, et al. (2001) "Tumor Hypoxia: Definitions and Current Clinical, Biologic and Molecular Aspects" Journal of the National Cancer Institute. 93(4):266-276.
Hollosi, et al. (2009). "Lysyl oxidase-like 2 promotes migration in noninvasive breast cancer cells but not in normal breast epithelial cells." Int J Cancer 125(2):318-327.
Hornstra et al. (2003) "Lysyl Oxidase is Required for Vascular and Diaphragmatic Development in Mice" *J. Biol. Chem.* 278(16):14387-14393.
Huang et al. (2001) "Cloning and Characterization of a Human Lysyl Oxidase-Like 3 Gene (hLOXL3)" *Matrix Biol.* 20(2):153-157.
Jain (1994) "Barriers to Drug Delivery in Solid Tumors" Scientific American 271(1):58-65.
Jansen & Csiszar (2007). "Intracellular localization of the matrix enzyme lysyl oxidase in polarized epithelial cells." Matrix Biol 26(2): 136-9.
Jansen, et al. (2006) "Lysyl oxidase regulates kidney epithelial cell phenotype" ASMB Meeting Abstrat/Matrix Biology 25:S92.
Jourdan Le-Saux et al. (1994) "Lysyl Oxidase cDNA of Myofibroblast from Mouse Fibrotic Liver" *Biochem. Biophys. Res. Comm.* 199(2):587-592.
Jourdan Le-Saux et al. (1999) "The LOXL2 Gene Encodes a New Lysyl Oxidase-Like Protein and Is Expressed at High Levels in Reproductive Tissues" *J. Biol. Chem.* 274(18):12939-12944.
Jourdan Le-Saux et al. (2001) "Central Nervous System, Uterus, Heart, and Leukocyte Expression of the LOXL3 Gene, Encoding a Novel Lysyl Oxidase-Like Protein" *Genomics* 74(2):211-218.
Jourdan-Le Saux, et al. (1998). "The human lysyl oxidase-related gene (LOXL2) maps between markers D8S280 and D8S278 on chromosome 8p21.2-p21.3." Genomics 51(2): 305-7.
Jourdan-Le Saux, et al. (2000). "The mouse lysyl oxidase-like 2 gene (mLOXL2) maps to chromosome 14 and is highly expressed in skin, lung and thymus." Matrix Biol 19(2): 179-83.
Jung, et al. (2003). "Purification of enzymatically active human lysyl oxidase and lysyl oxidase-like protein from *Escherichia coli* inclusion bodies." Protein Expr Purif 31(2): 240-6.
Kagan (1994) "Lysyl Oxidase: Mechanism, Regulation and Relationship to Liver Fibrosis" *Pathol. Res. Pract.* 190(9-10):910-919.
Kagan et al. (1982) "Lysyl Oxidase: Preparation and Role in Elastin Biosynthesis" *Meth. Enzymol.* 82(A):637-649.
Kagan et al. (2003) "Lysyl Oxidase: Properties, Specificity, and Biological Roles Inside and Outside of the Cell" *J. Cell. Biochem* 88(4):660-672.
Kagan, et al. (1995) "Expression of Lysyl Oxidase from cDNA Constructs in Mammalian Cells: The Propeptide Region Is Not Essential to the Folding and Secretion of the Functional Enzyme" J. Cell Biochem. 59(3):329-38.
Kagan, et al. (1995). "Catalytic properties and structural components of lysyl oxidase." *Novartis Foundation Symp.* 192: 100-15; discussion 115-21.
Kagan, H.M. (2000) "Intra-and Extracellular Enzymes of Collagen Biosynthesis as Biological and Chemical Targets in the Control of Fibrosis" Acta Tropica 77(1):147-152.
Kaku, et al. (2007). "Post-translational modifications of collagen upon BMP-induced osteoblast differentiation." Biochem Biophys Res Commun 359(3): 463-8.
Kamath et al. (2001) "Signaling from Protease-Activated Receptor-1 Inhibits Migration and Invasion of Breast Cancer Cells" *Cancer Res.* 61(15):5933-5940.
Kaneda et al. (2004) "Lysyl Oxidase is a Tumor Suppressor Gene Inactivated by Methylation and Loss of Heterozygosity in Human Gastric Cancers" Cancer Res. 64(18):6410-6415.
Kang, et al. "Prosaposin Inhibits Tumor Metastasis Via Paracrine and Endocrine Stimulation of Stromal p53 and Tsp-1" Proc. Natl. Acad. Sci. U.S.A. 106(29):12115-12120. (2009).
Kenyon, et al. (1991) "Lysyl Oxidase and rrg Messenger RNA" Science 253:802.
Kenyon, et al. (2003) "TGF-[beta]l Causes Airway Fibrosis and Increased Collagen I and III mRNA in Mice" Thorax 58(9):772-777.
Khakoo, et al. (1997) "Congenital Cutis Laxa and Lysyl Oxidase Deficiency" Clin. Genet. 51(2):109-14.
Kim et al. (1995) "A New Gene with Sequence and Structural Similarity to the Gene Encoding Human Lysyl Oxidase" *J. Biol. Chem.* 270(13):7176-7182.
Kim et al. (1999) "Coexpression of the Lysyl Oxidase-Like Gene (LOXL) and the Gene Encoding Type III Procollagen in Induced Liver Fibrosis" *J. Cell Biochem.* 72(2):181-188.
Kim et al. (2003) "Expression and Purification of Enzymatically Active Forms of the Human Lysyl Oxidase-Like Protein 4" *J. Biol. Chem.* 278(52):52071-52074.
Kim, et al. (1997). "A highly polymorphic (CA) repeat sequence in the human lysyl oxidase-like gene." Clin Genet 51(2): 131-2.
Kirschmann et al. (2002) "A Molecular Role for Lysyl Oxidase in Breast Cancer Invasion" Cancer Res. *Cancer Res.* 62(15):4478-4483.
Kirschmann, et al. (1999) "Differentially expressed genes associated with the metastatic phenotype in breast cancer" Breast Cancer Res Treat. 55(2):127-136.
Klutke, et al. (2008). "Decreased endopelvic fascia elastin content in uterine prolapse." Acta Obstet Gynecol Scand 87(1): 111-5.
Krebs & Krawetz (1993) "Lysyl Oxidase Copper-Talon Complex: A Model" Biochim. Biophys. Acta 1202(1):7-12.
Kresse, et al. (2008). "DNA copy number changes in high-grade malignant peripheral nerve sheath tumors by array CGH." Mol Cancer 7: 48.
Laczko, et al. (2007). "Active lysyl oxidase (LOX) correlates with focal adhesion kinase (FAK)/paxillin activation and migration in invasive astrocytes." Neuropathol Appl Neurobiol 33(6): 631-43.
Lazarus et al. (1995) "Induction of Human Monocyte Motility by Lysyl Oxidase" *Matrix Biol.* 14(9):727-731.

(56) References Cited

OTHER PUBLICATIONS

Le et al. (2007) "Expression and Prognostic Significance of a Panel of Tissue Hypoxia Markers in Head-and-Neck Squamous Cell Carcinoma," Int. J. Radiation Oncology Biol. Phys. 69(1):157-175.
Lelievre, et al. (2008). "VE-statin/egfl7 regulates vascular elastogenesis by interacting with lysyl oxidases." EMBO J 27(12): 1658-70.
Levene et al. (1985) "Possibilities for the Therapeutic Control of Fibrosis," Br. J. Dermatol. 112(3):363-371.
Li et al. (1997) "Localization and Activity of Lysyl Oxidase within Nuclei of Fibrogenic Cells" Proc. Natl. Acad. Sci. USA 94(24):12817-12822.
Li, et al. (2007). "Tumor microenvironment: the role of the tumor stroma in cancer." J Cell Biochem 101(4): 805-15.
Lucero & Kagan (2006). "Lysyl oxidase: an oxidative enzyme and effector of cell function." Cell Mol Life Sci 63(19-20): 2304-16.
Luo, et al. (1998) "Differential Inhibition of Fluid Accumulation and Tumor Growth in Two Mouse Ascites Tumors by an Antivascular Endothelial Growth Factor/Permeability Factor Neutralizing Antibody" Cancer Res. 58(12):2594-2600.
Luo, et al. "Significant expression of vascular endothelial growth factor/vascular permeability factor in mouse ascites tumors" Cancer Res., 1998, vol. 58, No. 12, pp. 2652-2660.
Macartney-Coxson, et al. (2008). "Metastatic susceptibility locus, an 8p hot-spot for tumour progression disrupted in colorectal liver metastases: 13 candidate genes examined at the DNA, mRNA and protein level." BMC Cancer 8: 187.
Madakamutil, et al. "Immunodominance in the TCR Repertoire of α TCR Peptide-Specific CD4+ Treg Population that Controls Experimental Autoimmune Encephalomyelitis" J. Immunology 2008, vol. 180, pp. 4577-4585.
Maki & Kivirikko (2001) "Cloning and Characterization of a Fourth Human Lysyl Oxidase Isoenzyme" Biochem. J. 355(Pt 2):381-387.
Mäki, et al. (2001). "Cloning and characterization of a fifth human lysyl oxidase isoenzyme: the third member of the lysyl oxidase-related subfamily with four scavenger receptor cysteine-rich domains." Matrix Biol 20(7): 493-6.
Mattioli, et al. "Mimicry of the Immunodominant Conformation-Dependent Antigenic Site of Hepatitis A Virus by Motifs Selected from Synthetic Peptide Libraries" Journal of Virology, Sep. 1995, vol. 69, No. 9, pp. 5294-5299.
Mbeunkui, et al. (2007) "Identification of differentially secreted biomarkers using LC-MS/MS in isogenic cell lines representing a progression of breast cancer" Journal Proteome Res. 6:2993-3002.
Molnar, et al. (2005). "Drosophila lysyl oxidases Dmloxl-1 and Dmloxl-2 are differentially expressed and the active DmLOXL-1 influences gene expression and development." J Biol Chem 280(24): 22977-85.
Monticone, et al. (2004). "Gene expression profile of human bone marrow stromal cells determined by restriction fragment differential display analysis." J Cell Biochem 92(4): 733-44.
Müller, et al. (2006). "Lung fibroblasts from patients with emphysema show markers of senescence in vitro." Respir Res 7: 32.
Murawaki et al. (1991) "Serum Lysyl Oxidase Activity in Chronic Liver Disease in Comparison with Serum Levels of Prolyl Hydroxylase and Laminin" Hepatology 14(6):1167-1173.
Nagaoka, et al. (2008). "1,25(OH)2D3 regulates collagen quality in an osteoblastic cell culture system." Biochem Biophys Res Commun 377(2): 674-8.
Nakken, et al. (2007). "Multiple inflammatory-, tissue remodelling- and fibrosis genes are differentially transcribed in the livers of Abcb4 (−/−) mice harbouring chronic cholangitis." Scand J Gastroenterol 42(10): 1245-55.
National Cancer Institute; Staging: Questions and answers, www.cancer.gov/cancertopics/factsheet/detection/staging, Nov. 6, 2009.
Nelson et al. (1988) "Effect of beta-Aminopropionitrile and Ascorbate on Fibroblast Migration" Proc. Soc. Exp. Biol. Med. 188(3):346-352.
Noblesse, et al. (2004) "Lsyl oxidase-like and lysysl oxidase are present in the dermis and epidermis of a skin equivalent and in himan skin and are associate to elastic fibers" J. Investig. Dermatol., 122:621-630.
Norrby (2006) "In vivo models of angiogenesis" J. Cell. Mol. Med. 10(3):588-612.
Ooshima & Midorikawa (1977) "Increased lysyl Oxidase Activity in Blood Vessels of Hypertensive Rats and Effect of beta-Aminopropionitrile on Arteriosclerosis" Jpn. Circ. J. 41(12):1337-40.
Orimo & Weinberg (2006). "Stromal fibroblasts in cancer: a novel tumor-promoting cell type." Cell Cycle 5(15): 1597-601.
Orimo, et al. (2001). "Cancer-associated myofibroblasts possess various factors to promote endometrial tumor progression." Clin Cancer Res 7(10): 3097-105.
Palamakumbura et al. (2002) "A Fluorometric Assay for Detection of Lysyl Oxidase Enzyme Activity in Biological Samples" Anal. Biochem. 300(2):245-251.
Palamakumbura, et al. (2004) "The Propeptide Domain of Lysyl Oxidase Induces Phenotypic Reversion of Ras-Transformed cells" J. Biol. Chem. 279(39):40593-40600.
Panchenko, et al. (1996) "Metalloproteinase activity secreted by fibrogenic cells in the processing of prolysyl oxidase Potential Role of Procollagen C-Proteinase" J Biol Chem. 271(12):7113-7119.
Pascal, et al. (2005). "Comparison of replicative senescence and stress-induced premature senescence combining differential display and low-density DNA arrays." FEBS Lett 579(17):3651-9.
Paul (1993) Fundamental Immunology, 3rd Ed., Raven Press: NY:292-295.
Payne, et al. (2005) "Lysyl oxidase regulates breast cancer cell migration and adhesion through a hydrogen peroxide-mediated mechanism" Cancer Res. 65(24):11429-11436.
Payne, et al. (2007). "Paradoxical roles for lysyl oxidases in cancer—a prospect." J Cell Biochem 101(6): 1338-54.
Peinado, et al. (2005) "A Molecular Role for Lysyl Oxidase-Like 2 Enzyme in Snail Regulation and Tumor Progression" EMBO J. 24(19):3446-3458.
Peinado, et al. (2005). "Switching on-off Snail: LOXL2 versus GSK3β." Cell Cycle 4(12): 1749-52.
Peinado, et al. (2008) "Lysyl Oxidase-like 2 as a New Poor Prognosis Marker of Squamous Cell Carcinomas" Cancer Research 68(12):4541-4550.
Peroutka, et al. (2008) "Enhanced Protein Expression in Mammalian Cells Using Engineered SUMO Fusions: Secreted phospholipase A2" Protein Sci. 17(9):1586-1595.
Peyrol, et al. (1997) "Lysyl oxidase gene expression in the stromal reaction to in situ and invasive ductal breast carcinoma" Am J. Pathol. 150(2):497-507.
Pinnell (1982) "Molecular Defects in the Ehlers-Danlos Syndrome" J. Invest. Dermatol. 79(Supp 1):905-925.
Pires Martins, et al. (2001). "Whole-body gene expression by data mining." Genomics 72(1): 34-42.
Polgar, et al. (2007). "Lysyl oxidase interacts with hormone placental lactogen and synergistically promotes breast epithelial cell proliferation and migration." J Biol Chem 282(5): 3262-72.
Postlethwaite, et al. (1987) "Stimulation of the chemotactic migration of human fibroblasts by transforming growth factor β" J. Exp. Med. 165(1):251-256.
Postovit, et al. (2008). "Hypoxia/reoxygenation: a dynamic regulator of lysyl oxidase-facilitated breast cancer migration." J Cell Biochem 103(5): 1369-78.
Pouysségur, et al. (2006) "Hypoxia Signalling in Cancer and Approaches to Enforce Tumour Regression" Nature 441(7092):437-443.
R&D Systems. Ordering Information: Catalog No. MAB2639. Anti-human lysyl oxidase homolog 2 monoclonal antibody. Apr. 18, 2005.
Radisky, et al. (2001) "Tumors Are Unique Organs Defined by Abnormal Signaling and Context" Semin. Cancer Bio. 11(2):87-95.
Rakic et al. (2003) "Placental Growth Factor, a Member of the VEGF Family, Contributes to the Development of Choroidal Neovascularization" Invest. Ophthalmol. Vis. Sci. 44(7):3186-3193.

(56) References Cited

OTHER PUBLICATIONS

Ren, et al. (1998) "Reduced lysyl oxidase messenger RNA levels in experimental and human prostate cancer" Cancer Res. 58:1285-1290.
Resnick, et al. (1994) "The SRCR Superfamily: A Family Reminiscent of the Ig Superfamily" Trends Biochem. Sci. 19(1):5-8.
Riechmann, et al. (1988) "Reshaping Human Antibodies for Therapy" Nature 332(6162):323-327.
Rodriguez et al. (2010) "Modulation of lysyl oxidase-like 2 enzymatic activity by an allosteric antibody inhibitor" J. Biol. Chem. 285:20964-20974.
Rodriguez, et al. (2008) Regulation of lysyl oxidase in vascular cells: lysyl oxidase as a new player in cardiovascular diseases. Cardiovasc Res. 79(1):7-13.
Rost, et al. (2003) "Reduction of LOX- and LOXL2-mRNA expression in head and neck squamous cell carcinomas" Anticancer Res. 23(2B):1565-1573.
Royce, et al. (1980) "Reduced Lysyl Oxidase Activity in Skin Fibroblasts from Patients with Menkes' Syndrome" Biochem. J. 192(2):579-86.
Rozalski, et al. "Epitope Specificities of Murine Monoclonal and Rabbit Polyclonal Antibodies against Enterobacterial Lipopolysaccharides of the Re Chemotype" Infection and Immunity, Sep. 1989, vol. 57, No. 9, pp. 2645-2652.
Rucker et al. (1998) "Copper, Lysyl Oxidase, and Extracellular Matrix Protein Cross-Linking" Am. J. Clin. Nutr. 67(5 Suppl):996S-1002S.
Rudikoff, et al. (1982) "Single Amino Acid Substitution Altering Antigen-Binding Specificity" PNAS USA 79(6):1979-1983.
Saito, et al. (1997) "Regulation of a novel gene encoding a lysyl o5cidase-related protein in cellular adhesion and senescence" J. Biol Chem. 272(13):8157-8160.
Salnikow, et al. (2008). "Regulation of hypoxia-inducible genes by ETS1 transcription factor." Carcinogenesis 29(8): 1493-9.
Sappino, et al. (1988) "Smooth-Muscle Differentiation in Stromal Cells of Malignant and Non-Malignant Breast Tissues" Int. J. Cancer 41(5):707-712. Abstract Only.
Satoh, et al. (2003) "Inhibition of local adhesion kinase by antisense oligonucleotides enhances the sensitivity of breast cancer cells to camptothecins" Biocell 27(1):47-55.
Schlotzer-Schrehardt, et al. (2008). "Genotype-correlated expression of lysyl oxidase-like 1 in ocular tissues of patients with pseudoexfoliation syndrome/glaucoma and normal patients." Am J Pathol 173(6): 1724-35.
Schmidt, et al. (2007). "[Mapping of a deletion interval on 8p21-22 in prostate cancer by gene dosage PCR]." Verh Dtsch Ges Pathol 91: 302-7.
Sebban, et al. (2009). "Lysyl oxidase-like 4 is alternatively spliced in an anatomic site-specific manner in tumors involving the serosal cavities." Virchows Arch 454(1): 71-9.
Selman, et al. (2006) "Gene Expression Profiles Distinguish Idiopathic Pulmonary Fibrosis from Hypersensitivity Pneumonitis" Am. J. Respir. Crit.Care Med. 173(2):188-198.
Sevil, et al. (1996) "Pharmacokinetic Analysis of Beta-Aminopropionitrile in Rabbits" Vet Res. 27(2):117-123 (Abstract only).
Sheppard (2006) "Transforming Growth Factor β: A Central Modulator of Pulmonary and Airway Inflammation and Fibrosis" Proc. Am. Thorac. Soc. 3(5):413-417.
Sheridan, et al. (1979) "Increased Lysyl Oxidase Activity in Aortas of Hypertensive Rats and Effect of Beta-Aminopropionitrile" Exp Mol Pathol. 30(2):315-324.
Shieh, et al. (2007) "Association of expression aberrances and genetic polymorphisms of lysyl oxidase with areca-associated oral tumorigenesis" Clinical Cancer Res. 13(15):4378-4385.
Siegel et al. (1978) "Biochemical and Immunochemical Study of Lysyl Oxidase in Experimental Hepatic Fibrosis in the Rat" Proc. Natl. Acad. Sci. USA 75(6):2945-2949.
Siegers, et al. (1986) "Hepatoprotection by Malotilate against Carbon Tetrachloride-Alcohol Induced Liver Fibrosis" Inflammation Res. 18(5-6):600-603. Abstract Only.
Sion, et al. (2006) "Lysyl oxidase (lox) and hypoxia-induced metastases" Cancer Biology & Therapy, 5(8):909-911.
Sivakumar, et al. (2008) "Upregulation of Lysyl Oxidase and MMPs During Cardiac Remodeling in Human Dilated Cardiomyopathy" Mol Cell Biochem 307(1-2):159-167.
Smith-Mungo & Kagan (1998) "Lysyl Oxidase: Properties, Regulation and Multiple Functions in Biology" Matrix Biol. 16: 387-98.
Sommer, et al. (1993) "Transient expression of lysyl oxidase by liver myofibroblasts in murine schistosomiasis" Laboratory Investigation 69(4):460-470.
Sørensen, et al. (2007) "Hypoxia-induced Expression of Endogenous Markers in Vitro is Highly Influenced by pH" Radiotherapy and Oncology 83:362-366.
Stapleton, et al. "Neutralization Escape Mutants Define a Dominant Immunogenic Neutralization Site on Hepatitis A Virus" Journal of Virology, Feb. 1987, vol. 61, No. 2, pp. 491-498.
Stassar, et al. (2001) "Identification of Human renal cell carcinoma associated genes by suppression subtractive hybridization" Br. J. Cancer 85(9):1372-1382.
Szabo, et al. (1997). "The human lysyl oxidase-like gene maps between STS markers D15S215 and GHLC.GCT7C09 on chromosome 15." Hum Genet 101(2): 198-200.
Szauter, et al. (2005). "Lysyl oxidase in development, aging and pathologies of the skin." Pathol Biol (Paris) 53(7): 448-56.
Tamura, et al. (1998) "Inhibition of Cell Migration, Spreading, and Focal Adhesions by Tumor Suppressor PTEN" Science 280:1614-1618.
Tang, et al. (1983). "Reaction of aortic lysyl oxidase with β-aminopropionitrile." J Biol Chem 258(7): 4331-8.
Tang, et al. (1984). "β-substituted ethylamine derivatives as suicide inhibitors of lysyl oxidase." J Biol Chem 259(2): 975-9.
Tarp, et al. "Identification of a Novel Cancer-Specific Immunodominant Glycopeptide Epitope in the MUC1 Tandem Repeat" Glycobiology, 2007, vol. 17, No. 2, pp. 197-209.
Thiery, et al. (2003) "Epithelial-Mesenchymal Transitions in Development and Pathologies" Curr. Opin. Cell. Biol. 15(6):740-6.
Thomassin, et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.
Tockman, et al. (1992) "Consideration in Bringing a Cancer Biomarker to Clinical Application" Cancer Res. 52:2711s-2718s.
Topp, et al. (1998) "Antibody Transport in Cultured Tumor Cell Layers" J. Control. Release 53(1-3):15-23.
Trackman & Kagan (1979). "Nonpeptidyl amine inhibitors are substrates of lysyl oxidase." J Biol Chem 254(16): 7831-6.
Trackman et al. (1981) "Development of a Peroxidase-Coupled Fluorometric Assay for Lysyl Oxidase" Anal. Biochem. 113(2):336-342.
Trackman, et al. (1991) "Cloning of rat aorta lysyl oxidase cDNA: Complete codons and predicted amino acid sequence" Biochem. 29(20)4863-4870 (1990 and Corrected Page: Biochem. 30(33):8282.
Trentham, et al. (1977) "Autoimmunity to Type II Collagen: An Experimental Model of Arthritis" J. Experimental Medicine 146:857-868.
Trivedy, et al. (1999) "The Upregulation of Lysyl Oxidase in Oral Submucous Fibrosis and Squamous Cell Carcinoma" J. Oral Pathol. Med. 28(6):246-251.
Understanding Cancer Series: Cancer Slide 8: Invasion and Metastasis, www.cancer.gov/cancertopics/understandingcancer/cancer/slide8.
Vadasz, et al. (2005). "Abnormal deposition of collagen around hepatocytes in Wilson's disease is associated with hepatocyte specific expression of lysyl oxidase and lysyl oxidase like protein-2." J Hepatol 43(3): 499-507.
Van Lancker, et al. (1995) "Patterns of axillary lymph node metastasis in breast cancer" Am. J. Clin. Oncol. 18(3):267-272.
Van Roy, et al. (1986) "Invasiveness and Metastatic Capability of Rat Fibroblast-like Cells before and after Transfection with Immortalizing and Transforming Genes" Cancer Res. 46:4787-4795.

(56) References Cited

OTHER PUBLICATIONS

Vautherot, et al. "Bovine Coronavirus Spike Glycoprotein: Localization of an Immunodominant Region at the Amino-Terminal End of S2" *Journal of General Virology*, 1992, vol. 73, pp. 3289-3294.
Waldmann (2003) "Immunotherapy: Past, Present and Future" *Nat. Med.* 9(3):269-277.
Walling, et al. (2004) "Agiessive basal cell carcinoma: Presentation, pathogenesis, and management" Cancer and Metastasis Reviews 23:389-402.
Wang, et al. (2007) "Lysyl Oxidase Inhibition Reduces Rat Liver Fibrosis after Bile Duct Ligation" Gastroenterology & Digestive Disease Week Meeting—108th Annual Meeting of the American-Gastroenterological-Association. Washington, DC. May 19-24, 2007; 132(4):A827.
Watters, et al. (1987) "Idiopathic Pulmonary Fibrosis. Pretreatment Bronchoalveolar Lavage Cellular Constituents and Their Relationships with Lung Histopathology and Clinical Response to Therapy" Am. Rev. Respir. Dis. 135(3):696-704. Abstract Only.
Weiner, (1999) "An Overview of Monoclonal Antibody Therapy of Cancer" Seminars Oncology 26(4):41-50.
Weise, et al. (2008). "LOXL4 is a selectively expressed candidate diagnostic antigen in head and neck cancer." Eur J Cancer 44(9): 1323-31.
Wu et al. (2007) "LOXL1 and LOXL4 are Epigenetically Silenced and Can Inhibit Ras/Extracellular Signal-Regulated Kinase Signaling Pathway in Human Bladder Cancer" *Cancer Res.* 67(9):4123-4129.
Zhang, et al. (2007) "Hypoxia Enhances Metastatic Efficiency in HT-1060 Fibrosarcoma Cells by Increasing Cell Survival in Lungs Not Cell Adhesion and Invasion" Cancer Res. 67(18):7789-7797.
Aplin, et al. (1998) "Signal Transduction and Signal Modulation by Cell Adhesion Receptors: The Role of Integrins, Cadherins, Immunoglobulin-Cell Adhesion Molecules and Selectins" *Pharmacol. Rev.* 50(2):197-263.
GenBank Accession No. AAA59525.1 "Lysyl Oxidase [*Homo sapiens*]" dated Jan. 7, 1995.
GenBank Accession No. AAA59541.1 "Lysyl Oxidase [*Homo sapiens*]" dated Jan. 7, 1995.
GenBank Accession No. AAB21243.1 "Lysyl Oxidase [*Homo sapiens*]" dated May 7, 1993.
GenBank Accession No. AAB23549.1 "Lysyl Oxidase [*Homo sapiens*]" dated May 8, 1993.
GenBank Accession No. AAD02130.1 "Lysyl Oxidase [*Homo sapiens*]" dated May 6, 1999.
GenBank Accession No. AAH15090.1 "Lysyl Oxidase-Like 1 [*Homo sapiens*]" dated Oct. 4, 2001.
GenBank Accession No. AAH74820.1 "Lysyl Oxidase [*Homo sapiens*]" dated Jul. 7, 2004.
GenBank Accession No. AAH74872.1 "Lysyl Oxidase [*Homo sapiens*]" dated Aug. 4, 2004.
GenBank Accession No. AAK51671.1 "Lysyl Oxidase-Like 3 Protein [*Homo sapiens*]" dated May 9, 2001.
GenBank Accession No. AAK71934.1 "Lysyl Oxidase-Related Protein C [*Homo sapiens*]" dated Jul. 11, 2001.
GenBank Accession No. AF039291 "*Homo sapiens* Lysyl Oxidase mRNA, Complete cds" May 6, 1999.
GenBank Accession No. AF282619 "*Homo sapiens* Lysyl Oxidase-like 3 Protein mRNA, Complete cds" dated May 9, 2001.
GenBank Accession No. AF338441 "*Homo sapiens* Lysyl Oxidase-Related Protein C (LOXC) mRNA, Complete cds" dated Jul. 11, 2001.
GenBank Accession No. BC015090 "*Homo sapiens* Lysyl Oxidase-Like 1, mRNA (cDNA Clone MGC:16541 Image:4040510), Complete cds" dated Oct. 4, 2001.
GenBank Accession No. BC018439 "*Mus musculus* Lysyl Oxidase, mRNA (cDNA Clone MGC:11525 Image:2655752), Complete cds" dated Dec. 6, 2001.
GenBank Accession No. BC074820 "*Homo sapiens* Lysyl Oxidase, mRNA (cDNA Clone MGC:104085 Image:30915536), Complete cds" dated Jul. 7, 2004.
GenBank Accession No. BC074872 "*Homo sapiens* Lysyl Oxidase, mRNA (cDNA Clone MGC:103851 Image:30915233), Complete cds" dated Jul. 7, 2004.
GenBank Accession No. M84150 "Human Lysyl Oxidase Gene, Partial cds" dated Jan. 7, 1995.
GenBank Accession No. M94054 "Human Lysyl Oxidase (LOX) mRNA, Complete cds" dated Jan. 7, 1995.
GenBank Accession No. NM_002317 "*Homo sapiens* Lysyl Oxidase (LOX), Transcript Variant 1, mRNA" dated Apr. 15, 2002.
GenBank Accession No. NM_033325 "*Mus musculus* Lysyl Oxidase-Like 2 (Lox12), mRNA" dated Aug. 12, 2003.
GenBank Accession No. NP_002308 "Protein-Lysine 6-Oxidase Isoform 1 Preproprotein [*Homo sapiens*]" dated Apr. 15, 2002.
GenBank Accession No. NP_002309 "Lysyl Oxidase Homolog 2 Precursor [*Homo sapiens*]" dated Feb. 1, 2002.
GenBank Accession No. NP_005567 "Lysyl Oxidase Homolog 1 Preproprotein [*Homo sapiens*]"dated Nov. 5, 2002.
GenBank Accession No. NP_034858 "Protein-Lysine 6-Oxidase Precursor [*Mus musculus*]"dated Jan. 7, 2002.
GenBank Accession No. NP_034859 "Lysyl Oxidase Homolog 1 Precursor [*Mus musculus*]"dated Mar. 17, 2004.
GenBank Accession No. NP_115587 "Lysyl Oxidase Homolog 4 Precursor [*Homo sapiens*]"dated May 19, 2001.
GenBank Accession No. NP_115882 "AP-1 Complex Subunit mu-1 Isoform 2 [*Homo sapiens*]"dated May 27, 2001.
GenBank Accession No. NP_201582 "Lysyl Oxidase homolog 2 Precursor [*Mus musculus*]"dated Aug. 12, 2003.
GenBank Accession No. 545875 "Lysyl Oxidase [Human, Skin Fibroblasts, mRNA Partial, 1254 nt]" May 8, 1993.
GenBank Accession No. 578694 "Lysyl Oxidase [Human, mRNA, 1780 nt]" dated May 7,1993.
GenBank Accession No. U89942 "Human Lysyl Oxidase-Related Protein (WS9-14) mRNA, Complete cds" dated Aug. 18, 2003.
Kaiser, et al. "First Pass at Cancer Genome Reveals Complex Landscape" (2006) *Science* 313(5792):1370.
Office Action mailed Sep. 23, 2010 in U.S. Appl. No. 12/185,054.
Office Action mailed Feb. 15, 2011 in U.S. Appl. No. 12/185,054.
International Preliminary Report on Patentability Chapter I issued Feb. 2, 2010, in PCT/US2008/009354.
Written Opinion of the ISA mailed Apr. 29, 2009, in PCT/US2008/009354.
International Search Report mailed Apr. 29, 2009, in PCT/US2008/009354.
Invitation to Pay Additional Fees mailed Jan. 14, 2009 (including Annex "Communication Relating to the Results of Partial International Search"), in PCT/US2008/009354.
Communication pursuant to Article 94(3) EPC dated Jun. 8, 2010, in EP 08795003.6-1222.
Communication pursuant to Article 94(3) EPC dated Jul. 19, 2011, in EP 08795003.6-1222.
Communication under Rule 71(3) EPC dated Jul. 23, 2012, in EP 08795003.6-1222.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.
International Preliminary Examination Report mailed Dec. 8, 2003, in PCT/IL01/00728.
Written Opinion mailed Jun. 6, 2003, in PCT/IL01/00728.
International Search Report mailed Dec. 17, 2002, in PCT/IL01/00728.
Invitation to Pay Additional Fees mailed May 23, 2002, in PCT/IL01/00728.
International Search Report mailed Jan. 5, 2006, in PCT/IL03/01008.
Invitation to Pay Additional Fees mailed Jun. 13, 2005, in PCT/IL03/01008.

(56) References Cited

OTHER PUBLICATIONS

European Search Report mailed Jul. 29, 2005, in EP 01958338.Apr. 2406.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
European Search Report mailed Feb. 29, 2008, in EP 03777136.7-1222.
Communication pursuant to Article 94(3) EPC mailed May 29, 2008, in EP 03777136.7-1222.
European Search Report mailed Dec. 21, 2009, in EP 08020754.1-2402.
European Search Opinion mailed Dec. 21, 2009, in EP 08020754.1-2402.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
European Search Report mailed Jun. 3, 2009, in EP 08020752.5-1222.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Report mailed Jun. 3, 2009, in EP 08020753.3-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jul. 13, 2011, in EP 10012458.5-2406.
European Search Opinion mailed Jul. 13, 2011, in EP 10012458.5-2406.
European Search Report mailed Jun. 27, 2011, in EP 10012457.7-2406.
European Search Opinion mailed Jun. 27, 2011, in EP 10012457.7-2406.
Office Action mailed Sep. 23, 2010, in U.S. Appl. No. 12/185,050.
Office Action mailed Feb. 15, 2011, in U.S. Appl. No. 12/185,050.
International Preliminary Report on Patentability Chapter I issued May 11, 2010, in PCT/US2008/072039.
Written Opinion of the ISA mailed Jan. 13, 2009, in PCT/US2008/072039.
International Search Report mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.
Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
International Search Report mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
International Search Report mailed Apr. 15, 2010, in PCT/US2010/023359.
International Preliminary Report on Patentability Chapter I issued Feb. 21, 2012, in PCT/US2010/046192.
Written Opinion of the ISA mailed Feb. 17, 2011, in PCT/US2010/046192.
International Search Report mailed Feb. 17, 2011, in PCT/US2010/046192.
Invitation to Pay Additional Fees mailed Nov. 18, 2010, in PCT/US2010/046192.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
International Search Report mailed Jan. 7, 2011, in PCT/US2010/046248.
Office Action mailed Jul. 12, 2012, in U.S. Appl. No. 12/860,693.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Search Report mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Search Report mailed May 17, 2011, in PCT/US2011/023791.
International Preliminary Report on Patentability Chapter I issued Feb. 21, 2012, in PCT/US2010/046244.
Written Opinion of the ISA mailed Feb. 8, 2011, in PCT/US2010/046244.
International Search Report mailed Feb. 8, 2011, in PCT/US2010/046244.
Invitation to Pay Additional Fees mailed Dec. 3, 2010, in PCT/US2010/046244.
Written Opinion of the ISA mailed Jun. 14, 2012, in PCT/US2012/032600.
International Search Report mailed Jun. 14, 2012, in PCT/US2012/032600.
Written Opinion of the ISA mailed Aug. 10, 2012, in PCT/US2012/037580.
International Search Report mailed Aug. 10, 2012, in PCT/US2012/037580.
Written Opinion of the ISA mailed Sep. 10, 2012, in PCT/US2012/040585.

(56) References Cited

OTHER PUBLICATIONS

International Search Report mailed Sep. 10, 2012, in PCT/US2012/040585.
Akhtar et al. (2002) "The sponge/Matrigel angiogenesis assay" Angiogenesis 5(1-2):75-80.
Albini et al. (2004) "The chemoinvasion assay: a tool to study tumor and endothelial cell invasion of basement membranes," Int. J. Dev. Biol. 48:563-571.
Armstrong et al. (1999) "Changes in Collagen Turnover in Early Acute Respiratory Distress Syndrome," Am. J. Respir. Crit. Care Med. 160:1910-1915.
Auerbach et al. (1974) "A simple procedure for the long-term cultivation of chicken embryos" Devel. Biol. 41(2):391-394.
Bedogni et al. (2004) "Topical treatment with inhibitors of the phosphatidylinositol 3'- kinase/Akt and Raf/mitogen-activated protein kinase kinase/extracellular signal-regulated kinase pathways reduces melanoma development in severe combined immunodeficient mice" Cancer Res. 64(7):2552-2560.
Beilmann et al. (2004) "Human primary co-culture angiogenesis assay reveals additive stimulation and different angiogenic properties of VEGF and HGF" Cytokine 26(4):178-185.
Berger et al. (2004) "A murine model of ex vivo angiogenesis using aortic disks grown in fibrin clot" Microvascular Res. 68(3):179-187.
Blacher et al. (2001) "Improved quantification of angiogenesis in the rat aortic ring assay" Angiogenesis 4(2):133-142.
BLAST 2 Sequences (LOR-1 and LOR-2) results version BLASTP 2.2.14, Apr. 9, 2006.
Brown et al. (1996) "A novel in vitro assay for human angiogenesis" Laboratory Investigation 75(4):539-555.
Castera (2011) "Invasive and Non-Invasive Methods for the Assessment of Fibrosis and Disease Progression in Chronic Liver Disease," Best Pract. Res. Clin. Gastroent. 25:291-303.
Chen (2005) "Boyden chamber assay" Methods Mol. Biol. 294:15-22.
Chua et al. (2005) "Pulmonary Fibrosis Searching for Model Answers," Am J. Respir. Cell. Mol. Biol. 33:9-13.
Database EMBL [Online] Oct. 28, 2008, "Sequence 15133 from Patent WO2004061423", retrieved from EBI accession No. EMBL: FB530075, Database accession No. FB530075.
De Eguileor et al. (2004) "Hirudo medicinalis: avascular tissues for clear-cut angiogenesis studies?" Current Pharmaceutical Design 10(16):1979-1998.
Gelatt (1977) "Animal models for glaucoma" Invest. Ophthalmol. Visual Sci. 16(7):592-596.
Grigorescu (2006) "Noninvasive Biochemical Markers of Liver Fibrosis," J. Gastrointestin. Liver Dis. 15(2):149-159.
Go et al. (2003) "The rat aortic ring assay for in vitro study of angiogenesis" Methods Mol. Med. 85:59-64.
González-Iriate et al. (2003) "A modified chorioallantoic membrane assay allows for specific detection of endothelial apoptosis induced by antiangiogenic substances" Angiogenesis 6(3):251-254.
Greenbaum et al. (2003) "Comparing protein abundance and mRNA expression levels on a genomic scale", Genome Biology 40 (9):117.01-117.08.
Guedez et al. (2003) "Quantitative assessment of angiogenic responses by the directed in vivo angiogenesis assay" Am. J. Pathol. 162(5):1431-1439.
Gulec et al. (2004) "A new in vitro assay for human tumor angiogenesis: three-dimensional human tumor angiogenesis assay" Ann. Surgical Oncology 11(1):99-104.
Hartwell (1998) "Angiogenesis in P- and E-selectin-deficient mice" Microcirculation 5(2-3):173-178.
Ishak et al. (1995) "Histological Grading and Staging of Chronic Hepatitis," J. Hepatol. 22:696-699.
Jakobsson et al .(1994) "A Morphometric Method to Evaluate Angiogenesis Kinetics in the Rat Mesentry" Intl. J. Exp. Pathol. 75(3):214-219.

Julien et al., (2008) "A reproducible and quantifiable model of choroidal neovascularization induced by VEGF A after subretinal adenoviral gene transfer in the rabbit" Molecular Vision 14: 1358-1372.
Knodell et al. (1981) "Formulation and Application of a Numerical Scoring System for Assessing Histological Activity in Asymptomatic Chronic Active Hepatitis," Hepatol. 1(5):431-435.
Kragh et al. (2003) "In vivo chamber angiogenesis assay: an optimized Matrigel plug assay for fast assessment of anti-angiogenic activity" Intl. J. Oncology 22(2):305-311.
Kragh et al. (2004) "A versatile in vivo chamber angiogenesis assay for measuring anti-angiogenic activity in mice" Oncology Reports 11(2):303-307.
Li et al. (1999) "Liver Fibrogenesis and the Role of Hepatic Stellate Cells: New Insights and Prospects for Therapy," J. of Gastroentero. and Hepatol. 14:618-633.
Lichtenberg et al. (1999) "The rat Subcutaneous Air Sac model: a quantitative assay of antiangiogenesis in induced vessels" Am. J. Pharmacol. Toxicology 84(1):34-40.
Lugassy, et al. (2012) "The Enzymatic Activity of Lysyl Oxidaslike-2 (LOXL2) Is Not Required for LOXL2-induced Inhibition of Keratinocyte Differentiation", Journal of Biological Chemistry 287(5):3541-3549.
Maier et al. (2009) "Correlation of mRNA and protein in complex biological samples", FEBS Letters 583 (24):3966-3973.
Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. (2011) 54 Supplement 1: S55-S56.
Masson et al. (2002) "Mouse Aortic Ring Assay: A New Approach of the Molecular Genetics of Angiogenesis" Biol. Proc. Online 4:24-31.
McKechnie et al. (2003) "Hr44 Secreted wtih exosomes: Loss from Ciliary epithelium in response to inflammation" IOVS 44(6): 2650-2656.
Mehal et al. (2011) "Expressway to the Core of Fibrosis," Nat. Med. 17(5):552-553.
Miller et al. (2004) "A novel technique for quantifying changes in vascular density, endothelial cell proliferation and protein expression in response to modulators of angiogenesis using the chick chorioallantoic membrane (CAM) assay" J. Translational Med. 2(1):4.
Morbidelli et al. (2004) "The rabbit corneal pocket assay for the study of angiogenesis" Cancer Treatment Res. 117:147-151.
NCBI dbSNP record for LOXL2, available at http://www.ncbi.nlm.nih.gov/projects/SNP/snp_ref.cqi?locusld=4017, retrieved Apr. 19, 2012.
Nehls et al. (1995) "A novel, microcarrier-based in vitro assay for rapid and reliable quantification of three-dimensional cell migration and angiogenesis" Microvascular Res. 50(3):311-322.
Nguyen et al. (1994) "Quantitation of angiogenesis and antiangiogenesis in the chick embryo chorioallantoic membrane" Microvascular Res. 47(1):31-40.
Nicosia et al. (1990) "Growth of microvessels in serum-free matrix culture of rat aorta. A quantitative assay of angiogenesis in vitro" Laboratory Investig. 63(1):115-122.
Nissanov et al. (1995) "Automatic vessel segmentation and quantification of the rat aortic ring assay of angiogenesis" Laboratory Investig. 73(5):734-739.
Norrby (1992) "On the quantitative rat mesenteric-window angiogenesis assay" EXS 61:282-286.
Okada et al. (1995) "A quantative in vivo method of analyzing human tumor-induced angiogenesis in mice using agarose microencapsulation and hemoglobin enzyme-linked immunosorbent assay" Japan. J. Cancer Res. 86(12):1182-1188.
Ogata et al. (1996) "Changes in alveolar capilary formation in growing rat lung by repeated injections of a lathyrogen" Growth, Development and Aging 60:153-160.
Parsons-Wingerter et al. (2000) "Fibroblast growth factor-2 selectively stimulates angiogenesis of small vessels in arterial tree" Arteriosclerosis Thrombosis Vasc. Biol. 20(5):1250-1256.
Presta et al. (1999) "Purine analogue 6-methylmercaptopurine riboside inhibits early and late phases of the angiogenesis process" Cancer Res. 59(10):2417-2424.

(56) References Cited

OTHER PUBLICATIONS

Reed et al.(2007) "Culture of murine aortic explants in 3-dimensional extracellular matrix: a novel, miniaturized assay of angiogenesis in vitro" Microvascular Res. 73(3):248-252.
Ribatti (2004) "The first evidence of the tumor-induced angiogenesis in vivo by using the chorioallantoic membrane assay dated 1913" Leukemia 18(8):1350-1351.
Ribatti et al. (1996) "The chick embryo chorioallantoic membrane as a model for in vivo research on angiogenesis" Intl. J. Devel. Biol. 40(6):1189-1197.
Ribatti et al. (1997) "New model for the study of angiogenesis and antiangiogenesis in the chick embryo chorioallantoic membrane: the gelatin sponge/chorioallantoic membrane assay" J. Vascular Res. 34(6):455-463.
Ribatti et al. (2000) "The Chick Embryo Chorioallantoic Membrane as a Model for In Vivo Research on Anti-Angiogenesis" Curr. Pharmacol. Biotechnol. 1(1):73-82.
Richardson et al. (2003) "Observations on the use of the avian chorioallantoic membrane (CAM) model in investigations into angiogenesis" Curr. Drug Targets Cardiovasc. Hematol. Disorders 3(2):155-185.
Roskoski (2007) "Vascular endothelial growth factor (VEGF) signaling in tumor progression" Critical Reviews in Oncology/Hematology 62:179-213.
Ruckert et al. (2009) "Functional analysis of LOXL2 in pancreatic carcinoma" International Journal of Colorectal Disease; Clinical and Molecular Gastroenterology and Surgery, Springer, Berlin, DE, 25(3):303-311.
Schena et al. (2005) "Pathogenic Mechanisms of Diabetic Nephropathy," J. Am. Soc. Nephrol. 16:S30-S33.
Scheuer (1991) "Classification of Chronic Viral Hepatitis: A Need for Reassessment," J. Hepatol. 13:372-374.
Sequence search result (Neufeld) 2010.
Siemann et al. "Tumor Vasculature: a Target for Anticancer Therapies" in: "Vascular-Targeted Therapies in Oncology", Mar. 10, 2006, John Wiley & Sons. Ltd. Chichester, UK.
Stiffey-Wilusz et al. (2001) "An ex vivo angiogenesis assay utilizing commercial porcine carotid artery: modification of the rat aortic ring assay" Angiogenesis 4(1):3-9.
Tzortzaki et al. (2006) "Active Remodeling in Idiopathic Interstitial Pneumonias: Evaluation of Collagen Types XII and XIV," J. Histochem. & Cytochem. 54(6):693-700.
Van Bergen et al. "The role of LOXa nd LOXL2 in wound healing after glaucoma filtration surgery", European association for vision and eye research, Oct. 8, 2010, Retrieved from the Internet: URL:http://www.ever.be/view_abstract.php?abs_id=5411.
Watanabe et al. (2010) "Nucleolin as cell surface receptor for tumor necrosis factor-alpha inducing protein: a carcinogenic factor of *Helicobacter pylori*", Journal of Cancer Research and Clinical Oncology 136(6):911-921.
Whaley-Connell et al. (2006) "Chronic Kidney Disease and the Cardiometabolic Syndrome," J. Clin. Hypert. 8(8):546-548.
Zhu et al. (2002) "The thin prep rat aortic ring assay: a modified method for the characterization of angiogenesis in whole mounts" Angiogenesis 5(1-2):81-86.
Caldas et al. (2003) "Humanization of the Anti-CD 18 Antibody 6.7: An Unexpected Effect of a Framework Residue in Binding to Antigen," Mol. Immunol. 39(15):941-952.
Casset et al. (2003) "A Peptide Mimetic of an Anti-CD4 Monoclonal Antibody by Rational Design," Biochem. Biophys. Res. Commun. 307(1): 198-205.
Chien et al. (1989) "Significant Structural and Functional Change of an Antigen-binding Site by a Distant Amino Acid Substitution: Proposal of a Structural Mechanism," Proc. Natl. Acad. Sci. USA 86(14): 5532-5536.
Giusti et al. (1987) "Somatic Diversification of S107 from an Antiphosphocholine to an Anti-DNA Autoantibody is Due to a Single Base Change in its Heavy Chain Variable Region," Proc. Natl. Acad. Sci. USA 84(9):2926-2930.
Gussow et al. (1991) "Humanization of Monoclonal Antibodies," Methods in Enzymology 203:99-121.
Harmsen and Haard (2007) "Properties, Production, and Applications of Camelid Single-domain Antibody Fragments," Appl. Microbiol. Biotechnol. 77:13-22.
Holm et al. (2007) "Functional Mapping and Single Chain Construction of the Anti-Cytokeratin 8 Monoclonal Antibody TS1," Mol. Immunol. 44(6):1075-1084.
Jiang et al., (2005) "A Novel Peptide Isolated from a Phage Display Peptide Library with Trastuzumab can Mimic Antigen Epitope of HER-2" J. Biol. Chem. 280(6):4656-4662.
MacCallum et al. (1996) "Antibody-antigen Interactions: Contact Analysis and Binding Site Topography," J. Mol. Biol. 262(5):732-745.
Mariuzza et al. (1987) "The Structural Basis of Antigen-antibody Recognition," Annu. Rev. Biophys. Chem. 16:139-159.
Pascalis, et al. (2002) "Grafting of "Abbreviated" Complementarity-Determining Regions Containing Specificity-Determining Residues Essential for Ligand Contact to Engineer a Less Immunogenic Humanized Monoclonal Antibody," J. Immunol. 169(6):3076-3084.
Stancoviski et al. (1991) "Mechanistic Aspects of the Opposing Effects of Monoclonal Antibodies to the ERBB2 Receptor on Tumor Growth," Proc. Natl. Acad. Sci USA 88:8691-8695.
Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.
Wu et al. (1999) "Humanization of a Murine Monoclonal Antibody by Simultaneous Optimization of Framework and CDR Residues," J. Mol. Biol. 294(1):151-162.
First Examination Report for New Zealand Patent Application No. 601615 mailed Apr. 4, 2013.
Notice of the Second Office Action for CN 200880110519.8, mailed Dec. 31, 2012.
Office Action mailed Jun. 3, 2013, in U.S. Appl. No. 13/619,139.
Office Action mailed Jan. 28, 2013 in U.S. Appl. No. 12/185,054.
Final Office Action mailed May 10, 2013 in U.S. Appl. No. 12/185,054.
Office Action mailed Apr. 2, 2013, in U.S. Appl. No. 13/707,495.
Partial European Search Report mailed Nov. 28, 2012 for EP 12172214.4.
Patent Examination Report No. 1 issued Nov. 19, 2012 for AU 2008282739.
Notice of Allowance mailed Feb. 6, 2013, in U.S. Appl. No. 12/185,050.
Office Action mailed Nov. 26, 2012, in U.S. Appl. No. 13/204,336.
Office Action mailed Jan. 7, 2013, in U.S. Appl. No. 13/204,336.
Communication pursuant to Article 94(3) EPC mailed Nov. 22, 2012 for EP 08 830 207.0.
European Search Report mailed Nov. 28, 2012 for EP 12172222.7.
Patent Examination Report No. 1 mailed Dec. 12, 2012 for AU 2008299784.
Notice on the Second Office Action (translation) mailed Nov. 23, 2012 for CN 200880101321.3.
Notice of Reasons for Rejection (translation) mailed Feb. 1, 2013 for JP 2010-519263.
Office Action mailed Feb. 28, 2013, in U.S. Appl. No. 12/652,687.
Communication pursuant to Rules 70(2) and 70a(2) EPC mailed Nov. 5, 2012 for EP 10739181.5.
Notice of Allowance mailed Nov. 23, 2012 for U.S. Appl. No. 12/860,625.
Supplementary European Search Report mailed Nov. 26, 2012 for EP 10810673.3.
Examination Report mailed Nov. 5, 2012 for NZ 598466.
Final Office Action mailed Nov. 15, 2012 for U.S. Appl. No. 12/860,693.
Supplementary European Search Report mailed Dec. 4, 2012 for EP 10810675.8.
Non-Final Office Action mailed Jan. 10, 2013 for U.S. Appl. No. 12/860,834.
Examination Report mailed Nov. 6, 2012 for NZ 598456.
Examination Report mailed Nov. 5, 2012 for NZ 598464.
Extended Search Report mailed Mar. 5, 2013, for EP 10810702.0.

(56) References Cited

OTHER PUBLICATIONS

Communication Pursuant to Rules 70(2) and 70a(2) EPC mailed Mar. 22, 2013, for EP 10810702.0.
Extended Search Report mailed Mar. 21, 2013, for EP 12172214.4.
Fujimoto et al. (2009) "Reciprocal Regulation of LOX and LOXL2 Expression During Cell Adhesion and Terminal Differentiation in Epidermal Keratinocytes," Journal of Dermatological Science 55(2):91-98.
Maki et al. (2002) "Inactivation of the Lysyl Oxidase Gene Lox Leads to Aortic Aneurysms, Cardiovascular Dysfunction, and Perinatal Death in Mice," Circulation 106(19):2503-2509.
Mollenhauer, et al. (1987) "Distribution of Extracellular Matrix Proteins in Pancreatic Ductal Adenocarcinoma and Its Influence on Tumor Cell Proliferation in Vitro," 2(1): 14-24.
Portolano, et al. (1993). "Lack of Promiscuity in Autoantigen-Specific H and L Chain Combinations as Revealed by Human H and L Chain 'Roulette'". J Immunol 150(3):880-887.
Tannock. "Experimental Chemotherapy," Ch. 19, p. 338 and 352-359, in The Basic Science of Oncology, Tannock and Hill, eds., New York 1992.
Terui, et al. (2006) "Blockade of Bulky Lymphoma-Associated CD55 Expression by RNA Interference Overcomes Resistance to Complement-Dependent Cytotoxicity with Rituximab," Cancer Sci. 97:72-79.
Final Office Action for U.S. Appl. No. 12/860,834, mailed Jul. 26, 2013.
Final Office Action for U.S. Appl. No. 12/652,687 mailed Aug. 1, 2013.
Notice of Allowance (translation) for JP 2010-519263, mailed Jun. 21, 2013.
Advisory Action for U.S. Appl. No. 12/185,054 mailed Aug. 20, 2013.
Office Action (translation) for Japanese Application No. 2010-519951 mailed Jul. 12, 2013.
Decision on Rejection (translation) for CN 200880101321.3 mailed Jul. 3, 2013.
First Office Action (translation) for CN 201080047979.8 mailed Jun. 28, 2013.
Non-Final Office Action for U.S. Appl. No. 13/487,109 mailed Aug. 8, 2013.
Decision to Grant for EP 10012458.5 dated Sep. 12, 2013.
Search Report and Written Opinion for SN 201201215-9 mailed Jul. 19, 2013.
First Office Action (translation) for CN 201080047970.7 mailed Jul. 26, 2013.
American Thoracic Society International Consensus Statement (2000) "Idiopathic Pulmonary Fibrosis: Diagnosis and Treatment" Am J Respir Grit Care Med 161:646-664.
Peng et al. (2009) "Secreted LOXL2 is a Novel Therapeutic Target that Promotes Gastric Cancer Metastasis via the Src/FAK Pathway," Carcinogenesis 30(10):1660-1669.
Schietke et al. (2010) "The Lysyl Oxidases LOX and LOXL2 are Necessary and Sufficient to Repress E-cadherin in Hypoxia: Insights into Cellular Transformation Processes Mediated by HIF-1," Journal of Biological Chemistry 285(9):6658-6669 (Published, JBC Papers in Press, Dec. 21, 2009).

\* cited by examiner

FIGURE 1

MERPLCSHLC SCLAMLALLS PLSLAQYDSW PHYPEYFQQP APEYHQPQAP ANVAKIQLRL 60
    SIGNAL PEPTIDE

AGQKRKHSEG RVEVYYDGQW GTVCDDDFSI HAAHVVCREL GYVEAKSWTA SSSYGKGEGP 120
                           SRCR1

IWLDNLHCTG NEATLAACTS NGWGVTDCKH TEDVGVVCSD KRIPGFKFDN SLINQIENLN 180

IQVEDIRIRA ILSTYRKRTP VMEGYVEVKE GKTWKQICDK HWTAKNSRVV CGMFGFPGER 240

TYNTKVYKMF ASRRKQRYWP FSMDCTGTEA HISSCKLGPQ VSLDPMKNVT CENGLPAVVS 300
                           SRCR2

CVPGQVFSPD GPSRFRKAYK PEQPLVRLRG GAYIGEGRVE VLKNGEWGTV CDDKWDLVSA 360

SVVCRELGFG SAKEAVTGSR LGQGIGPIHL NEIQCTGNEK SIIDCKFNAE SQGCNHEEDA 420
                           SRCR3

GVRCNTPAMG LQKKLRLNGG RNPYEGRVEV LVERNGSLVW GMVCGQNWGI VEAMVVCRQL 480

GLGFASNAFQ ETWYWHGDVN SNKVVMSGVK CSGTELSLAH CRHDGEDVAC PQGGVQYGAG 540
                           SRCR4

VACSETAPDL VLNAEMVQQT TYLEDRPMFM LQCAMEENCL SASAAQTDPT TGYRRLLRFS 600
                 CATALYTIC DOMAIN

SQIHNNGQSD FRPKNGRHAW IWHDCHRHYH SMEVFTHYDL LNLNGTKVAE GHKASFCLED 660

TECEGDIQKN YECANFGDQG ITMGCWDMYR HDIDCQWVDI TDVPPGDYLF QVVINPNFEV 720

AESDYSNNIM KCRSRYDGHR IWMYNCHIGG SFSEETEKKF EHFSGLLNNQ LSPQ    774

SEQ ID NO:1

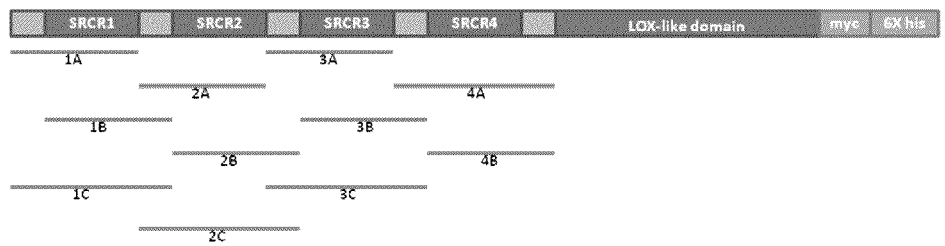

B

SRCR1A (aa1-159)

MERPLCSHLCSCLAMLALLSPLSLAQYDSWPHYPEYFQQPAPEYHQPQAPANVAKIQLRLAGQK
RKHSEGRVEVYYDGQWGTVCDDDFSIHAAHVVCRELGYVEAKSWTASSSYGKGEGPIWLDNLHC
TGNEATLAACTSNGWGVTDCKHTEDVGVVCS     (SEQ ID NO:14)

SRCR1B (aa58-187)
LRLAGQKRKHSEGRVEVYYDGQWGTVCDDDFSIHAAHVVCRELGYVEAKSWTASSSYGKGEGPI
WLDNLHCTGNEATLAACTSNGWGVTDCKHTEDVGVVCSDKRIPGFKFDNSLINQIENLNIQVED
IR   (SEQ ID NO:15)

SRCR1C (aa1-187)
MERPLCSHLCSCLAMLALLSPLSLAQYDSWPHYPEYFQQPAPEYHQPQAPANVAKIQLRLAGQK
RKHSEGRVEVYYDGQWGTVCDDDFSIHAAHVVCRELGYVEAKSWTASSSYGKGEGPIWLDNLHC
TGNEATLAACTSNGWGVTDCKHTEDVGVVCSDKRIPGFKFDNSLINQIENLNIQVEDIR
(SEQ ID NO:16)

SRCR2A (aa160-302)
DKRIPGFKFDNSLINQIENLNIQVEDIRIRAILSTYRKRTPVMEGYVEVKEGKTWKQICDKHWT
AKNSRVVCGMFGFPGERTYNTKVYKMFASRRKQRYWPFSMDCTGTEAHISSCKLGPQVSLDPMK
NVTCENGLPAVVSCV   (SEQ ID NO:17)

FIGURE 2 (CON'T)

B (CON'T)

SRCR2B (aa188-324)
IRAILSTYRKRTPVMEGYVEVKEGKTWKQICDKHWTAKNSRVVCGMFGFPGERTYNTKVYKMFA
SRRKQRYWPFSMDCTGTEAHISSCKLGPQVSLDPMKNVTCENGLPAVVSCVPGQVFSPDGPSRF
RKAYKPEQP  (SEQ ID NO:18)

SRCR2C (aa160-324)
DKRIPGFKFDNSLINQIENLNIQVEDIRIRAILSTYRKRTPVMEGYVEVKEGKTWKQICDKHWT
AKNSRVVCGMFGFPGERTYNTKVYKMFASRRKQRYWPFSMDCTGTEAHISSCKLGPQVSLDPMK
NVTCENGLPAVVSCVPGQVFSPDGPSRFRKAYKPEQP  (SEQ ID NO:19)

SRCR3A (aa303-425)
PGQVFSPDGPSRFRKAYKPEQPLVRLRGGAYIGEGRVEVLKNGEWGTVCDDKWDLVSASVVCRE
LGFGSAKEAVTGSRLGQGIGPIHLNEIQCTGNEKSIIDCKFNAESQGCNHEEDAGVRCN
(SEQ ID NO:20)

SRCR3B (aa325-434)
LVRLRGGAYIGEGRVEVLKNGEWGTVCDDKWDLVSASVVCRELGFGSAKEAVTGSRLGQGIGPI
HLNEIQCTGNEKSIIDCKFNAESQGCNHEEDAGVRCNTPAMGLQKK  (SEQ ID NO:21)

SRCR3C (303-434)
PGQVFSPDGPSRFRKAYKPEQPLVRLRGGAYIGEGRVEVLKNGEWGTVCDDKWDLVSASVVCRE
LGFGSAKEAVTGSRLGQGIGPIHLNEIQCTGNEKSIIDCKFNAESQGCNHEEDAGVRCNTPAMG
LQKK  (SEQ ID NO:22)

SRCR4A (aa426-547)
TPAMGLQKKLRLNGGRNPYEGRVEVLVERNGSLVWGMVCGQNWGIVEAMVVCRQLGLGFASNAF
QETWYWHGDVNSNKVVMSGVKCSGTELSLAHCRHDGEDVACPQGGVQYGAGVACSETA  (SEQ
ID NO:23)

SRCR4B (435-547)
LRLNGGRNPYEGRVEVLVERNGSLVWGMVCGQNWGIVEAMVVCRQLGLGFASNAFQETWYWHGD
VNSNKVVMSGVKCSGTELSLAHCRHDGEDVACPQGGVQYGAGVACSETA (SEQ ID NO:24)

FIGURE 4

Alignment of SRCR4 Domain of Human LOXL2, LOXL3, and LOXL4

```
LOXL2  LRLNGGRNPY EGRVEVLVER NGSLVWGMVC GQNWGIVEAM VVCRQLGLGF ASNAFQETWY
LOXL3  IRLSGGRSQH EGRVEVQIGG PGPLRWGLIC GDDWGTLEAM VACRQLGLGY ANHGLQETWY
LOXL4  VRLAGGRIPE EGLLEVQVEV NGVPRWGSVC SENWGLTEAM VACRQLGLGF AIHAYKETWF

LOXL2  WHGDVNSNKV VMSGVKCSGT ELSLAHCRHD GEDVACPQGG VQYGAGVACS  (SEQ ID NO:35)
LOXL3  WDSG-NITEV VMSGVRCTGT ELSLDQCAHH GTHITCKRTG TRFTAGVICS  (SEQ ID NO:36)
LOXL4  WSGTPRAQEV VMSGVRCSGT ELALQQCQRH GP-VHCSHGG GRFLAGVSCM  (SEQ ID NO:37)
```

FIGURE 5

```
H:  PDLVLNAEMV  QQTTYLEDRP  MFMLQCAMEE  NCLSASAAQT  DPTTGYRRLL  RFSSQIHNNG
M:  PDLVLNAEIV  QQTAYLEDRP  MSLLQCAMEE  NCLSASAVHT  DPTRGHRRLL  RFSSQIHNNG
R:  PDLVLNAEIV  QQTAYLEDRP  MALLQCAMEE  NCLSASAVHT  DPTRGHRRLL  RFSSQIHNNG
C:  PDLVLNAEMV  QQTTYLEDRP  MFMLQCAMEE  NCLSASAAQT  NPTTGYRRLL  RFSSQIHNNG

H:  QSDFRPKNGR  HAWIWHDCHR  HYHSMEVFTH  YDLLNLNGTK  VAEGHKASFC  LEDTECEGDI
M:  QSDFRPKNGR  HAWIWHDCHR  HYHSMEVFTY  YDLLSLNGTK  VAEGHKASFC  LEDTECEGDI
R:  QSDFRPKNGR  HAWIWHDCHR  HYHSMEVFTY  YDLLSLNGTK  VAEGHKASFC  LEDTECEGDI
C:  QSDFRPKNGR  HAWIWHDCHR  HYHSMEVFTH  YDLLNLNGTK  VAEGHKASFC  LEDTECEGDI

*
H:  QKNYECANFG  DQGITMGCWD  MYRHDIDCQW  VDITDVPPGD  YLFQVVINPN  FEVAESDYSN
M:  QKSYECANFG  EQGITMGCWD  MYRHDIDCQW  IDITDVPPGD  YLFQVVINPN  YEVPESDFSN
R:  QKSYECANFG  EQGITMGCWD  MYRHDIDCQW  IDITDVPPGD  YLFQVVINPN  YEVPESDFSN
C:  QKNYECANFG  DQGITMGCWD  MYRHDIDCQW  IDITDVPPGD  YLFQVVINPN  FEVAESDYSN

*
H:  NIMKCRSRYD  GHRIWMYNCH  IGGSFSEETE  KKFEHFSGLL  NNQLSPQ  (SEQ ID NO:38)
M:  NIMKCRSRYD  GYRIWMYNCH  VGGAFSEETE  QKFEHFSGLL  NNQLSVQ  (SEQ ID NO:39)
R:  NIMKCRSRYD  GYRIWMYNCH  VGGAFSEETE  QKFEHFSGLL  NNQLSVQ  (SEQ ID NO:40)
C:  NIMKCRSRYD  GHRIWMYNCH  IGGSFSEETE  KKFEHFSGLL  NNQLSPQ  (SEQ ID NO:41)
```

FIGURE 6

AB0023 V$_H$ sequence:

MEWSRVFIFLLSVTAGVHSQVQLQQSGAELVRPGTSVKVSCKASGYAFTYYLIEWVKQ
RPGQGLEWIGVINPGSGGTNYNEKFKGKATLTADKSSSTAYMQLSSLTSDDSAVYFCAR
NWMNFDYWGQGTTLTVSS (SEQ ID NO:42)

AB0023 V$_L$ sequence:

MRCLAEFLGLLVLWIPGAIGDIVMTQAAPSVSVTPGESVSISCRSSKSLLHSNGNTYLYW
FLQRPGQSPQFLIYRMSNLASGVPDRFSGSGSGTAFTLRISRVEAEDVGVYYCMQHLEYP
YTFGGGTKLEIK (SEQ ID NO:43)

AB0024 V$_H$ sequence:

MGWSLILLFLVAVATRVHSQVQLVQSGAEVKKPGASVKVSCKASGYAFTYYLIEWVRQ
APGQGLEWIGVINPGSGGTNYNEKFKGRATITADKSTSTAYMELSSLRSEDTAVYFCAR
NWMNFDYWGQGTTVTVSSASTKGPSVFPLAPCSRSTSESTAALGCLVKDYFPEPVTVS
WNSGALTSGVHTFPAVLQSSGLYSLSSVVTVPSSSLGTKTYTCNVDHKPSNTKVDKRVE
SKYGPPCPPCPAPEFLGGPSVFLFPPKPKDTLMISRTPEVTCVVVDVSQEDPEVQFNWYV
DGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID
NO:44)

AB0024 V$_L$ sequence:

MRVPAQLLGLLLLWLPGARCDIVMTQTPLSLSVTPGQPASISCRSSKSLLHSNGNTYLY
WFLQKPGQSPQFLIYRMSNLASGVPDRFSGSGSGTDFTLKISRVEAEDVGVYYCMQHLE
YPYTFGGGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNR
GEC (SEQ ID NO:45)

SEQUENCE LISTING

<160> NUMBER OF SEQ ID NOS: 45

<210> SEQ ID NO 1
<211> LENGTH: 774
<212> TYPE: PRT
<213> ORGANISM: Homo sapiens

<400> SEQUENCE: 1

```
Met Glu Arg Pro Leu Cys Ser His Leu Cys Ser Cys Leu Ala Met Leu
 1               5                  10                  15

Ala Leu Leu Ser Pro Leu Ser Leu Ala Gln Tyr Asp Ser Trp Pro His
                20                  25                  30

Tyr Pro Glu Tyr Phe Gln Gln Pro Ala Pro Glu Tyr His Gln Pro Gln
            35                  40                  45

Ala Pro Ala Asn Val Ala Lys Ile Gln Leu Arg Leu Ala Gly Gln Lys
        50                  55                  60

Arg Lys His Ser Glu Gly Arg Val Glu Val Tyr Tyr Asp Gly Gln Trp
 65                  70                  75                  80

Gly Thr Val Cys Asp Asp Phe Ser Ile His Ala Ala His Val Val
                 85                  90                  95

Cys Arg Glu Leu Gly Tyr Val Glu Ala Lys Ser Trp Thr Ala Ser Ser
                100                 105                 110

Ser Tyr Gly Lys Gly Glu Gly Pro Ile Trp Leu Asp Asn Leu His Cys
            115                 120                 125

Thr Gly Asn Glu Ala Thr Leu Ala Ala Cys Thr Ser Asn Gly Trp Gly
        130                 135                 140

Val Thr Asp Cys Lys His Thr Glu Asp Val Gly Val Val Cys Ser Asp
145                 150                 155                 160

Lys Arg Ile Pro Gly Phe Lys Phe Asp Asn Ser Leu Ile Asn Gln Ile
                165                 170                 175

Glu Asn Leu Asn Ile Gln Val Glu Asp Ile Arg Ile Arg Ala Ile Leu
            180                 185                 190

Ser Thr Tyr Arg Lys Arg Thr Pro Val Met Glu Gly Tyr Val Glu Val
        195                 200                 205

Lys Glu Gly Lys Thr Trp Lys Gln Ile Cys Asp Lys His Trp Thr Ala
    210                 215                 220

Lys Asn Ser Arg Val Val Cys Gly Met Phe Gly Phe Pro Gly Glu Arg
225                 230                 235                 240

Thr Tyr Asn Thr Lys Val Tyr Lys Met Phe Ala Ser Arg Arg Lys Gln
                245                 250                 255

Arg Tyr Trp Pro Phe Ser Met Asp Cys Thr Gly Thr Glu Ala His Ile
            260                 265                 270

Ser Ser Cys Lys Leu Gly Pro Gln Val Ser Leu Asp Pro Met Lys Asn
        275                 280                 285

Val Thr Cys Glu Asn Gly Leu Pro Ala Val Val Ser Cys Val Pro Gly
    290                 295                 300

Gln Val Phe Ser Pro Asp Gly Pro Ser Arg Phe Arg Lys Ala Tyr Lys
305                 310                 315                 320

Pro Glu Gln Pro Leu Val Arg Leu Arg Gly Gly Ala Tyr Ile Gly Glu
                325                 330                 335

Gly Arg Val Glu Val Leu Lys Asn Gly Glu Trp Gly Thr Val Cys Asp
            340                 345                 350

Asp Lys Trp Asp Leu Val Ser Ala Ser Val Val Cys Arg Glu Leu Gly
        355                 360                 365
```

```
Phe Gly Ser Ala Lys Glu Ala Val Thr Gly Ser Arg Leu Gly Gln Gly
            370                 375                 380
Ile Gly Pro Ile His Leu Asn Glu Ile Gln Cys Thr Gly Asn Glu Lys
385                 390                 395                 400
Ser Ile Ile Asp Cys Lys Phe Asn Ala Glu Ser Gln Gly Cys Asn His
                405                 410                 415
Glu Glu Asp Ala Gly Val Arg Cys Asn Thr Pro Ala Met Gly Leu Gln
            420                 425                 430
Lys Lys Leu Arg Leu Asn Gly Gly Arg Asn Pro Tyr Glu Gly Arg Val
            435                 440                 445
Glu Val Leu Val Glu Arg Asn Gly Ser Leu Val Trp Gly Met Val Cys
            450                 455                 460
Gly Gln Asn Trp Gly Ile Val Glu Ala Met Val Val Cys Arg Gln Leu
465                 470                 475                 480
Gly Leu Gly Phe Ala Ser Asn Ala Phe Gln Glu Thr Trp Tyr Trp His
                485                 490                 495
Gly Asp Val Asn Ser Asn Lys Val Val Met Ser Gly Val Lys Cys Ser
            500                 505                 510
Gly Thr Glu Leu Ser Leu Ala His Cys Arg His Asp Gly Glu Asp Val
            515                 520                 525
Ala Cys Pro Gln Gly Val Gln Tyr Gly Ala Gly Val Ala Cys Ser
530                 535                 540
Glu Thr Ala Pro Asp Leu Val Leu Asn Ala Glu Met Val Gln Gln Thr
545                 550                 555                 560
Thr Tyr Leu Glu Asp Arg Pro Met Phe Met Leu Gln Cys Ala Met Glu
                565                 570                 575
Glu Asn Cys Leu Ser Ala Ser Ala Ala Gln Thr Asp Pro Thr Thr Gly
            580                 585                 590
Tyr Arg Arg Leu Leu Arg Phe Ser Ser Gln Ile His Asn Asn Gly Gln
            595                 600                 605
Ser Asp Phe Arg Pro Lys Asn Gly Arg His Ala Trp Ile Trp His Asp
            610                 615                 620
Cys His Arg His Tyr His Ser Met Glu Val Phe Thr His Tyr Asp Leu
625                 630                 635                 640
Leu Asn Leu Asn Gly Thr Lys Val Ala Glu Gly His Lys Ala Ser Phe
                645                 650                 655
Cys Leu Glu Asp Thr Glu Cys Glu Gly Asp Ile Gln Lys Asn Tyr Glu
            660                 665                 670
Cys Ala Asn Phe Gly Asp Gln Gly Ile Thr Met Gly Cys Trp Asp Met
            675                 680                 685
Tyr Arg His Asp Ile Asp Cys Gln Trp Val Asp Ile Thr Asp Val Pro
            690                 695                 700
Pro Gly Asp Tyr Leu Phe Gln Val Val Ile Asn Pro Asn Phe Glu Val
705                 710                 715                 720
Ala Glu Ser Asp Tyr Ser Asn Asn Ile Met Lys Cys Arg Ser Arg Tyr
                725                 730                 735
Asp Gly His Arg Ile Trp Met Tyr Asn Cys His Ile Gly Gly Ser Phe
            740                 745                 750
Ser Glu Glu Thr Glu Lys Lys Phe Glu His Phe Ser Gly Leu Leu Asn
            755                 760                 765
Asn Gln Leu Ser Pro Gln
770
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Thr Pro Ala Met Gly Leu Gln Lys Lys
 1               5

<210> SEQ ID NO 3
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 3

Val Trp Gly Met Val Cys Gly Gln Asn Trp Gly Ile Val Glu Ala Met
 1               5                   10                  15

Val Val Cys Arg Gln Leu Gly Leu Gly Phe Ala Ser Asn Ala Phe Gln
                20                  25                  30

Glu Thr Trp Tyr Trp His Gly
            35

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

His His His His His His
 1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Cys Tyr Pro Tyr Asp Val Pro Asp Tyr Ala
 1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Asp Tyr Lys Asp Asp Asp Asp Lys
 1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 7
```

```
Cys Glu Gln Lys Leu Ile Ser Glu Glu Asp Leu
1               5                   10
```

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 8

```
His His His His His
1               5
```

<210> SEQ ID NO 9
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 9

```
Trp Ser His Pro Gln Phe Glu Lys
1               5
```

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

```
Tyr Pro Tyr Asp Val Pro Asp Tyr Ala
1               5
```

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 11

```
Arg Tyr Ile Arg Ser
1               5
```

<210> SEQ ID NO 12
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 12

```
Phe His His Thr
1
```

<210> SEQ ID NO 13
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 13

```
Trp Glu Ala Ala Ala Arg Glu Ala Cys Cys Arg Glu Cys Cys Ala Arg
1               5                   10                  15
```

Ala

<210> SEQ ID NO 14
<211> LENGTH: 159
<212> TYPE: PRT
<213> ORGANISM: Homo sapiens

<400> SEQUENCE: 14

Met Glu Arg Pro Leu Cys Ser His Leu Cys Ser Cys Leu Ala Met Leu
1               5                   10                  15

Ala Leu Leu Ser Pro Leu Ser Leu Ala Gln Tyr Asp Ser Trp Pro His
            20                  25                  30

Tyr Pro Glu Tyr Phe Gln Gln Pro Ala Pro Glu Tyr His Gln Pro Gln
        35                  40                  45

Ala Pro Ala Asn Val Ala Lys Ile Gln Leu Arg Leu Ala Gly Gln Lys
    50                  55                  60

Arg Lys His Ser Glu Gly Arg Val Glu Val Tyr Tyr Asp Gly Gln Trp
65                  70                  75                  80

Gly Thr Val Cys Asp Asp Asp Phe Ser Ile His Ala Ala His Val Val
                85                  90                  95

Cys Arg Glu Leu Gly Tyr Val Glu Ala Lys Ser Trp Thr Ala Ser Ser
            100                 105                 110

Ser Tyr Gly Lys Gly Glu Gly Pro Ile Trp Leu Asp Asn Leu His Cys
        115                 120                 125

Thr Gly Asn Glu Ala Thr Leu Ala Ala Cys Thr Ser Asn Gly Trp Gly
    130                 135                 140

Val Thr Asp Cys Lys His Thr Glu Asp Val Gly Val Val Cys Ser
145                 150                 155

<210> SEQ ID NO 15
<211> LENGTH: 130
<212> TYPE: PRT
<213> ORGANISM: Homo sapiens

<400> SEQUENCE: 15

Leu Arg Leu Ala Gly Gln Lys Arg Lys His Ser Glu Gly Arg Val Glu
1               5                   10                  15

Val Tyr Tyr Asp Gly Gln Trp Gly Thr Val Cys Asp Asp Asp Phe Ser
            20                  25                  30

Ile His Ala Ala His Val Val Cys Arg Glu Leu Gly Tyr Val Glu Ala
        35                  40                  45

Lys Ser Trp Thr Ala Ser Ser Ser Tyr Gly Lys Gly Glu Gly Pro Ile
    50                  55                  60

Trp Leu Asp Asn Leu His Cys Thr Gly Asn Glu Ala Thr Leu Ala Ala
65                  70                  75                  80

Cys Thr Ser Asn Gly Trp Gly Val Thr Asp Cys Lys His Thr Glu Asp
                85                  90                  95

Val Gly Val Val Cys Ser Asp Lys Arg Ile Pro Gly Phe Lys Phe Asp
            100                 105                 110

Asn Ser Leu Ile Asn Gln Ile Glu Asn Leu Asn Ile Gln Val Glu Asp
        115                 120                 125

Ile Arg
    130

<210> SEQ ID NO 16
<211> LENGTH: 187
<212> TYPE: PRT

<213> ORGANISM: Homo sapiens

<400> SEQUENCE: 16

Met Glu Arg Pro Leu Cys Ser His Leu Cys Ser Cys Leu Ala Met Leu
1               5                   10                  15

Ala Leu Leu Ser Pro Leu Ser Leu Ala Gln Tyr Asp Ser Trp Pro His
            20                  25                  30

Tyr Pro Glu Tyr Phe Gln Gln Pro Ala Pro Glu Tyr His Gln Pro Gln
        35                  40                  45

Ala Pro Ala Asn Val Ala Lys Ile Gln Leu Arg Leu Ala Gly Gln Lys
    50                  55                  60

Arg Lys His Ser Glu Gly Arg Val Glu Val Tyr Tyr Asp Gly Gln Trp
65              70                  75                  80

Gly Thr Val Cys Asp Asp Phe Ser Ile His Ala Ala His Val Val
                85                  90                  95

Cys Arg Glu Leu Gly Tyr Val Glu Ala Lys Ser Trp Thr Ala Ser Ser
            100                 105                 110

Ser Tyr Gly Lys Gly Glu Gly Pro Ile Trp Leu Asp Asn Leu His Cys
        115                 120                 125

Thr Gly Asn Glu Ala Thr Leu Ala Ala Cys Thr Ser Asn Gly Trp Gly
    130                 135                 140

Val Thr Asp Cys Lys His Thr Glu Asp Val Gly Val Val Cys Ser Asp
145                 150                 155                 160

Lys Arg Ile Pro Gly Phe Lys Phe Asp Asn Ser Leu Ile Asn Gln Ile
                165                 170                 175

Glu Asn Leu Asn Ile Gln Val Glu Asp Ile Arg
            180                 185

<210> SEQ ID NO 17
<211> LENGTH: 143
<212> TYPE: PRT
<213> ORGANISM: Homo sapiens

<400> SEQUENCE: 17

Asp Lys Arg Ile Pro Gly Phe Lys Phe Asp Asn Ser Leu Ile Asn Gln
1               5                   10                  15

Ile Glu Asn Leu Asn Ile Gln Val Glu Asp Ile Arg Ile Arg Ala Ile
            20                  25                  30

Leu Ser Thr Tyr Arg Lys Arg Thr Pro Val Met Glu Gly Tyr Val Glu
        35                  40                  45

Val Lys Glu Gly Lys Thr Trp Lys Gln Ile Cys Asp Lys His Trp Thr
    50                  55                  60

Ala Lys Asn Ser Arg Val Val Cys Gly Met Phe Gly Phe Pro Gly Glu
65              70                  75                  80

Arg Thr Tyr Asn Thr Lys Val Tyr Lys Met Phe Ala Ser Arg Arg Lys
                85                  90                  95

Gln Arg Tyr Trp Pro Phe Ser Met Asp Cys Thr Gly Thr Glu Ala His
            100                 105                 110

Ile Ser Ser Cys Lys Leu Gly Pro Gln Val Ser Leu Asp Pro Met Lys
        115                 120                 125

Asn Val Thr Cys Glu Asn Gly Leu Pro Ala Val Val Ser Cys Val
    130                 135                 140

<210> SEQ ID NO 18
<211> LENGTH: 137
<212> TYPE: PRT
<213> ORGANISM: Homo sapiens

```
<400> SEQUENCE: 18

Ile Arg Ala Ile Leu Ser Thr Tyr Arg Lys Arg Thr Pro Val Met Glu
 1               5                  10                  15

Gly Tyr Val Glu Val Lys Glu Gly Lys Thr Trp Lys Gln Ile Cys Asp
             20                  25                  30

Lys His Trp Thr Ala Lys Asn Ser Arg Val Val Cys Gly Met Phe Gly
         35                  40                  45

Phe Pro Gly Glu Arg Thr Tyr Asn Thr Lys Val Tyr Lys Met Phe Ala
     50                  55                  60

Ser Arg Arg Lys Gln Arg Tyr Trp Pro Phe Ser Met Asp Cys Thr Gly
 65                  70                  75                  80

Thr Glu Ala His Ile Ser Ser Cys Lys Leu Gly Pro Gln Val Ser Leu
             85                  90                  95

Asp Pro Met Lys Asn Val Thr Cys Glu Asn Gly Leu Pro Ala Val Val
            100                 105                 110

Ser Cys Val Pro Gly Gln Val Phe Ser Pro Asp Gly Pro Ser Arg Phe
        115                 120                 125

Arg Lys Ala Tyr Lys Pro Glu Gln Pro
    130                 135

<210> SEQ ID NO 19
<211> LENGTH: 165
<212> TYPE: PRT
<213> ORGANISM: Homo sapiens

<400> SEQUENCE: 19

Asp Lys Arg Ile Pro Gly Phe Lys Phe Asp Asn Ser Leu Ile Asn Gln
 1               5                  10                  15

Ile Glu Asn Leu Asn Ile Gln Val Glu Asp Ile Arg Ile Arg Ala Ile
             20                  25                  30

Leu Ser Thr Tyr Arg Lys Arg Thr Pro Val Met Glu Gly Tyr Val Glu
         35                  40                  45

Val Lys Glu Gly Lys Thr Trp Lys Gln Ile Cys Asp Lys His Trp Thr
     50                  55                  60

Ala Lys Asn Ser Arg Val Val Cys Gly Met Phe Gly Phe Pro Gly Glu
 65                  70                  75                  80

Arg Thr Tyr Asn Thr Lys Val Tyr Lys Met Phe Ala Ser Arg Arg Lys
             85                  90                  95

Gln Arg Tyr Trp Pro Phe Ser Met Asp Cys Thr Gly Thr Glu Ala His
            100                 105                 110

Ile Ser Ser Cys Lys Leu Gly Pro Gln Val Ser Leu Asp Pro Met Lys
        115                 120                 125

Asn Val Thr Cys Glu Asn Gly Leu Pro Ala Val Val Ser Cys Val Pro
    130                 135                 140

Gly Gln Val Phe Ser Pro Asp Gly Pro Ser Arg Phe Arg Lys Ala Tyr
145                 150                 155                 160

Lys Pro Glu Gln Pro
                165

<210> SEQ ID NO 20
<211> LENGTH: 123
<212> TYPE: PRT
<213> ORGANISM: Homo sapiens

<400> SEQUENCE: 20

Pro Gly Gln Val Phe Ser Pro Asp Gly Pro Ser Arg Phe Arg Lys Ala
```

```
                1               5                  10                 15
Tyr Lys Pro Glu Gln Pro Leu Val Arg Leu Arg Gly Gly Ala Tyr Ile
                        20                 25                 30

Gly Glu Gly Arg Val Glu Val Leu Lys Asn Gly Glu Trp Gly Thr Val
                35                 40                 45

Cys Asp Asp Lys Trp Asp Leu Val Ser Ala Ser Val Val Cys Arg Glu
        50                 55                 60

Leu Gly Phe Gly Ser Ala Lys Glu Ala Val Thr Gly Ser Arg Leu Gly
65                 70                 75                 80

Gln Gly Ile Gly Pro Ile His Leu Asn Glu Ile Gln Cys Thr Gly Asn
                        85                 90                 95

Glu Lys Ser Ile Ile Asp Cys Lys Phe Asn Ala Glu Ser Gln Gly Cys
                100                105                110

Asn His Glu Glu Asp Ala Gly Val Arg Cys Asn
                115                120
```

<210> SEQ ID NO 21
<211> LENGTH: 110
<212> TYPE: PRT
<213> ORGANISM: Homo sapiens

<400> SEQUENCE: 21

```
Leu Val Arg Leu Arg Gly Gly Ala Tyr Ile Gly Glu Gly Arg Val Glu
1               5                  10                 15

Val Leu Lys Asn Gly Glu Trp Gly Thr Val Cys Asp Asp Lys Trp Asp
                20                 25                 30

Leu Val Ser Ala Ser Val Val Cys Arg Glu Leu Gly Phe Gly Ser Ala
        35                 40                 45

Lys Glu Ala Val Thr Gly Ser Arg Leu Gly Gln Gly Ile Gly Pro Ile
    50                 55                 60

His Leu Asn Glu Ile Gln Cys Thr Gly Asn Glu Lys Ser Ile Ile Asp
65                 70                 75                 80

Cys Lys Phe Asn Ala Glu Ser Gln Gly Cys Asn His Glu Glu Asp Ala
                        85                 90                 95

Gly Val Arg Cys Asn Thr Pro Ala Met Gly Leu Gln Lys Lys
                100                105                110
```

<210> SEQ ID NO 22
<211> LENGTH: 132
<212> TYPE: PRT
<213> ORGANISM: Homo sapiens

<400> SEQUENCE: 22

```
Pro Gly Gln Val Phe Ser Pro Asp Gly Pro Ser Arg Phe Arg Lys Ala
1               5                  10                 15

Tyr Lys Pro Glu Gln Pro Leu Val Arg Leu Arg Gly Gly Ala Tyr Ile
                        20                 25                 30

Gly Glu Gly Arg Val Glu Val Leu Lys Asn Gly Glu Trp Gly Thr Val
                35                 40                 45

Cys Asp Asp Lys Trp Asp Leu Val Ser Ala Ser Val Val Cys Arg Glu
        50                 55                 60

Leu Gly Phe Gly Ser Ala Lys Glu Ala Val Thr Gly Ser Arg Leu Gly
65                 70                 75                 80

Gln Gly Ile Gly Pro Ile His Leu Asn Glu Ile Gln Cys Thr Gly Asn
                        85                 90                 95

Glu Lys Ser Ile Ile Asp Cys Lys Phe Asn Ala Glu Ser Gln Gly Cys
                100                105                110
```

Asn His Glu Glu Asp Ala Gly Val Arg Cys Asn Thr Pro Ala Met Gly
        115                 120                 125

Leu Gln Lys Lys
        130

<210> SEQ ID NO 23
<211> LENGTH: 122
<212> TYPE: PRT
<213> ORGANISM: Homo sapiens

<400> SEQUENCE: 23

Thr Pro Ala Met Gly Leu Gln Lys Lys Leu Arg Leu Asn Gly Gly Arg
 1               5                  10                  15

Asn Pro Tyr Glu Gly Arg Val Glu Val Leu Val Glu Arg Asn Gly Ser
            20                  25                  30

Leu Val Trp Gly Met Val Cys Gly Gln Asn Trp Gly Ile Val Glu Ala
        35                  40                  45

Met Val Val Cys Arg Gln Leu Gly Leu Gly Phe Ala Ser Asn Ala Phe
50                  55                  60

Gln Glu Thr Trp Tyr Trp His Gly Asp Val Asn Ser Asn Lys Val Val
65                  70                  75                  80

Met Ser Gly Val Lys Cys Ser Gly Thr Glu Leu Ser Leu Ala His Cys
                85                  90                  95

Arg His Asp Gly Glu Asp Val Ala Cys Pro Gln Gly Gly Val Gln Tyr
            100                 105                 110

Gly Ala Gly Val Ala Cys Ser Glu Thr Ala
        115                 120

<210> SEQ ID NO 24
<211> LENGTH: 113
<212> TYPE: PRT
<213> ORGANISM: Homo sapiens

<400> SEQUENCE: 24

Leu Arg Leu Asn Gly Gly Arg Asn Pro Tyr Glu Gly Arg Val Glu Val
 1               5                  10                  15

Leu Val Glu Arg Asn Gly Ser Leu Val Trp Gly Met Val Cys Gly Gln
            20                  25                  30

Asn Trp Gly Ile Val Glu Ala Met Val Val Cys Arg Gln Leu Gly Leu
        35                  40                  45

Gly Phe Ala Ser Asn Ala Phe Gln Glu Thr Trp Tyr Trp His Gly Asp
50                  55                  60

Val Asn Ser Asn Lys Val Val Met Ser Gly Val Lys Cys Ser Gly Thr
65                  70                  75                  80

Glu Leu Ser Leu Ala His Cys Arg His Asp Gly Glu Asp Val Ala Cys
                85                  90                  95

Pro Gln Gly Gly Val Gln Tyr Gly Ala Gly Val Ala Cys Ser Glu Thr
            100                 105                 110

Ala

<210> SEQ ID NO 25
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 25

```
Leu Arg Leu Asn Gly Gly Arg Asn Pro Tyr Glu Gly Arg Val Glu
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 26

```
Arg Val Glu Val Leu Val Glu Arg Asn Gly Ser Leu Val Trp Gly
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 27

```
Val Trp Gly Met Val Cys Gly Gln Asn Trp Gly Ile Val Glu Ala
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 28

```
Val Glu Ala Met Val Val Cys Arg Gln Leu Gly Leu Gly Phe Ala
1               5                   10                  15
```

<210> SEQ ID NO 29
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 29

```
Gly Phe Ala Ser Asn Ala Phe Gln Glu Thr Trp Tyr Trp His Gly
1               5                   10                  15
```

<210> SEQ ID NO 30
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 30

```
Trp His Gly Asp Val Asn Ser Asn Lys Val Val Met Ser Gly Val
1               5                   10                  15
```

<210> SEQ ID NO 31
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 31

```
Ser Gly Val Lys Cys Ser Gly Thr Glu Leu Ser Leu Ala His Cys
1               5                   10                  15
```

```
<210> SEQ ID NO 32
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 32

Ala His Cys Arg His Asp Gly Glu Asp Val Ala Cys Pro Gln Gly
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

Pro Gln Gly Gly Val Gln Tyr Gly Ala Gly Val Ala Cys Ser Glu
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Cys Ser Glu Thr Ala Pro Asp Leu Val Leu Asn Ala Glu Met Val
 1               5                  10                  15

<210> SEQ ID NO 35
<211> LENGTH: 110
<212> TYPE: PRT
<213> ORGANISM: Homo sapiens

<400> SEQUENCE: 35

Leu Arg Leu Asn Gly Gly Arg Asn Pro Tyr Glu Gly Arg Val Glu Val
 1               5                  10                  15

Leu Val Glu Arg Asn Gly Ser Leu Val Trp Gly Met Val Cys Gly Gln
                20                  25                  30

Asn Trp Gly Ile Val Glu Ala Met Val Val Cys Arg Gln Leu Gly Leu
            35                  40                  45

Gly Phe Ala Ser Asn Ala Phe Gln Glu Thr Trp Tyr Trp His Gly Asp
        50                  55                  60

Val Asn Ser Asn Lys Val Val Met Ser Gly Val Lys Cys Ser Gly Thr
65                  70                  75                  80

Glu Leu Ser Leu Ala His Cys Arg His Asp Gly Glu Asp Val Ala Cys
                85                  90                  95

Pro Gln Gly Gly Val Gln Tyr Gly Ala Gly Val Ala Cys Ser
            100                 105                 110

<210> SEQ ID NO 36
<211> LENGTH: 109
<212> TYPE: PRT
<213> ORGANISM: Homo sapiens

<400> SEQUENCE: 36

Ile Arg Leu Ser Gly Gly Arg Ser Gln His Glu Gly Arg Val Glu Val
 1               5                  10                  15
```

```
Gln Ile Gly Gly Pro Gly Pro Leu Arg Trp Gly Leu Ile Cys Gly Asp
            20                  25                  30

Asp Trp Gly Thr Leu Glu Ala Met Val Ala Cys Arg Gln Leu Gly Leu
        35                  40                  45

Gly Tyr Ala Asn His Gly Leu Gln Glu Thr Trp Tyr Trp Asp Ser Gly
 50                  55                  60

Asn Ile Thr Glu Val Val Met Ser Gly Val Arg Cys Thr Gly Thr Glu
 65                  70                  75                  80

Leu Ser Leu Asp Gln Cys Ala His His Gly Thr His Ile Thr Cys Lys
                85                  90                  95

Arg Thr Gly Thr Arg Phe Thr Ala Gly Val Ile Cys Ser
            100                 105

<210> SEQ ID NO 37
<211> LENGTH: 109
<212> TYPE: PRT
<213> ORGANISM: Homo sapiens

<400> SEQUENCE: 37

Val Arg Leu Ala Gly Gly Arg Ile Pro Glu Glu Gly Leu Leu Glu Val
 1               5                  10                  15

Gln Val Glu Val Asn Gly Val Pro Arg Trp Gly Ser Val Cys Ser Glu
            20                  25                  30

Asn Trp Gly Leu Thr Glu Ala Met Val Ala Cys Arg Gln Leu Gly Leu
        35                  40                  45

Gly Phe Ala Ile His Ala Tyr Lys Glu Thr Trp Phe Trp Ser Gly Thr
 50                  55                  60

Pro Arg Ala Gln Glu Val Val Met Ser Gly Val Arg Cys Ser Gly Thr
 65                  70                  75                  80

Glu Leu Ala Leu Gln Gln Cys Gln Arg His Gly Pro Val His Cys Ser
                85                  90                  95

His Gly Gly Gly Arg Phe Leu Ala Gly Val Ser Cys Met
            100                 105

<210> SEQ ID NO 38
<211> LENGTH: 227
<212> TYPE: PRT
<213> ORGANISM: Homo sapiens

<400> SEQUENCE: 38

Pro Asp Leu Val Leu Asn Ala Glu Met Val Gln Gln Thr Thr Tyr Leu
 1               5                  10                  15

Glu Asp Arg Pro Met Phe Met Leu Gln Cys Ala Met Glu Glu Asn Cys
            20                  25                  30

Leu Ser Ala Ser Ala Ala Gln Thr Asp Pro Thr Thr Gly Tyr Arg Arg
        35                  40                  45

Leu Leu Arg Phe Ser Ser Gln Ile His Asn Asn Gly Gln Ser Asp Phe
 50                  55                  60

Arg Pro Lys Asn Gly Arg His Ala Trp Ile Trp His Asp Cys His Arg
 65                  70                  75                  80

His Tyr His Ser Met Glu Val Phe Thr His Tyr Asp Leu Leu Asn Leu
                85                  90                  95

Asn Gly Thr Lys Val Ala Glu Gly His Lys Ala Ser Phe Cys Leu Glu
            100                 105                 110

Asp Thr Glu Cys Glu Gly Asp Ile Gln Lys Asn Tyr Glu Cys Ala Asn
        115                 120                 125

Phe Gly Asp Gln Gly Ile Thr Met Gly Cys Trp Asp Met Tyr Arg His
```

```
                130                 135                 140
Asp Ile Asp Cys Gln Trp Val Asp Ile Thr Asp Val Pro Pro Gly Asp
145                 150                 155                 160

Tyr Leu Phe Gln Val Val Ile Asn Pro Asn Phe Glu Val Ala Glu Ser
                165                 170                 175

Asp Tyr Ser Asn Asn Ile Met Lys Cys Arg Ser Arg Tyr Asp Gly His
                180                 185                 190

Arg Ile Trp Met Tyr Asn Cys His Ile Gly Gly Ser Phe Ser Glu Glu
                195                 200                 205

Thr Glu Lys Lys Phe Glu His Phe Ser Gly Leu Leu Asn Asn Gln Leu
                210                 215                 220

Ser Pro Gln
225

<210> SEQ ID NO 39
<211> LENGTH: 227
<212> TYPE: PRT
<213> ORGANISM: Mus musculus

<400> SEQUENCE: 39

Pro Asp Leu Val Leu Asn Ala Glu Ile Val Gln Gln Thr Ala Tyr Leu
  1               5                  10                  15

Glu Asp Arg Pro Met Ser Leu Leu Gln Cys Ala Met Glu Glu Asn Cys
                 20                  25                  30

Leu Ser Ala Ser Ala Val His Thr Asp Pro Thr Arg Gly His Arg Arg
                 35                  40                  45

Leu Leu Arg Phe Ser Ser Gln Ile His Asn Asn Gly Gln Ser Asp Phe
 50                  55                  60

Arg Pro Lys Asn Gly Arg His Ala Trp Ile Trp His Asp Cys His Arg
 65                  70                  75                  80

His Tyr His Ser Met Glu Val Phe Thr Tyr Tyr Asp Leu Leu Ser Leu
                 85                  90                  95

Asn Gly Thr Lys Val Ala Glu Gly His Lys Ala Ser Phe Cys Leu Glu
                100                 105                 110

Asp Thr Glu Cys Glu Gly Asp Ile Gln Lys Ser Tyr Glu Cys Ala Asn
                115                 120                 125

Phe Gly Glu Gln Gly Ile Thr Met Gly Cys Trp Asp Met Tyr Arg His
                130                 135                 140

Asp Ile Asp Cys Gln Trp Ile Asp Ile Thr Asp Val Pro Pro Gly Asp
145                 150                 155                 160

Tyr Leu Phe Gln Val Val Ile Asn Pro Asn Tyr Glu Val Pro Glu Ser
                165                 170                 175

Asp Phe Ser Asn Asn Ile Met Lys Cys Arg Ser Arg Tyr Asp Gly Tyr
                180                 185                 190

Arg Ile Trp Met Tyr Asn Cys His Val Gly Gly Ala Phe Ser Glu Glu
                195                 200                 205

Thr Glu Gln Lys Phe Glu His Phe Ser Gly Leu Leu Asn Asn Gln Leu
                210                 215                 220

Ser Val Gln
225

<210> SEQ ID NO 40
<211> LENGTH: 227
<212> TYPE: PRT
<213> ORGANISM: Rattus norvegicus

<400> SEQUENCE: 40
```

```
Pro Asp Leu Val Leu Asn Ala Glu Ile Val Gln Gln Thr Ala Tyr Leu
1               5                   10                  15

Glu Asp Arg Pro Met Ala Leu Leu Gln Cys Ala Met Glu Glu Asn Cys
            20                  25                  30

Leu Ser Ala Ser Ala Val His Thr Asp Pro Thr Arg Gly His Arg Arg
        35                  40                  45

Leu Leu Arg Phe Ser Ser Gln Ile His Asn Asn Gly Gln Ser Asp Phe
    50                  55                  60

Arg Pro Lys Asn Gly Arg His Ala Trp Ile Trp His Asp Cys His Arg
65                  70                  75                  80

His Tyr His Ser Met Glu Val Phe Thr Tyr Tyr Asp Leu Leu Ser Leu
                85                  90                  95

Asn Gly Thr Lys Val Ala Glu Gly His Lys Ala Ser Phe Cys Leu Glu
            100                 105                 110

Asp Thr Glu Cys Glu Gly Asp Ile Gln Lys Ser Tyr Glu Cys Ala Asn
        115                 120                 125

Phe Gly Glu Gln Gly Ile Thr Met Gly Cys Trp Asp Met Tyr Arg His
    130                 135                 140

Asp Ile Asp Cys Gln Trp Ile Asp Ile Thr Asp Val Pro Pro Gly Asp
145                 150                 155                 160

Tyr Leu Phe Gln Val Val Ile Asn Pro Asn Tyr Glu Val Pro Glu Ser
                165                 170                 175

Asp Phe Ser Asn Asn Ile Met Lys Cys Arg Ser Arg Tyr Asp Gly Tyr
            180                 185                 190

Arg Ile Trp Met Tyr Asn Cys His Val Gly Gly Ala Phe Ser Glu Glu
        195                 200                 205

Thr Glu Gln Lys Phe Glu His Phe Ser Gly Leu Leu Asn Asn Gln Leu
    210                 215                 220

Ser Val Gln
225

<210> SEQ ID NO 41
<211> LENGTH: 227
<212> TYPE: PRT
<213> ORGANISM: Macaca fascicularis

<400> SEQUENCE: 41

Pro Asp Leu Val Leu Asn Ala Glu Met Val Gln Gln Thr Thr Tyr Leu
1               5                   10                  15

Glu Asp Arg Pro Met Phe Met Leu Gln Cys Ala Met Glu Glu Asn Cys
            20                  25                  30

Leu Ser Ala Ser Ala Ala Gln Thr Asn Pro Thr Thr Gly Tyr Arg Arg
        35                  40                  45

Leu Leu Arg Phe Ser Ser Gln Ile His Asn Asn Gly Gln Ser Asp Phe
    50                  55                  60

Arg Pro Lys Asn Gly Arg His Ala Trp Ile Trp His Asp Cys His Arg
65                  70                  75                  80

His Tyr His Ser Met Glu Val Phe Thr His Tyr Asp Leu Leu Asn Leu
                85                  90                  95

Asn Gly Thr Lys Val Ala Glu Gly His Lys Ala Ser Phe Cys Leu Glu
            100                 105                 110

Asp Thr Glu Cys Glu Gly Asp Ile Gln Lys Asn Tyr Glu Cys Ala Asn
        115                 120                 125

Phe Gly Asp Gln Gly Ile Thr Met Gly Cys Trp Asp Met Tyr Arg His
    130                 135                 140
```

Asp Ile Asp Cys Gln Trp Ile Asp Ile Thr Asp Val Pro Pro Gly Asp
145                 150                 155                 160

Tyr Leu Phe Gln Val Val Ile Asn Pro Asn Phe Glu Val Ala Glu Ser
            165                 170                 175

Asp Tyr Ser Asn Asn Ile Met Lys Cys Arg Ser Arg Tyr Asp Gly His
            180                 185                 190

Arg Ile Trp Met Tyr Asn Cys His Ile Gly Gly Ser Phe Ser Glu Glu
            195                 200                 205

Thr Glu Lys Lys Phe Glu His Phe Ser Gly Leu Leu Asn Asn Gln Leu
210                 215                 220

Ser Pro Gln
225

<210> SEQ ID NO 42
<211> LENGTH: 135
<212> TYPE: PRT
<213> ORGANISM: Mus musculus

<400> SEQUENCE: 42

Met Glu Trp Ser Arg Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
            35                  40                  45

Thr Tyr Tyr Leu Ile Glu Trp Val Lys Gln Arg Pro Gly Gln Gly Leu
50                  55                  60

Glu Trp Ile Gly Val Ile Asn Pro Gly Ser Gly Gly Thr Asn Tyr Asn
65                  70                  75                  80

Glu Lys Phe Lys Gly Lys Ala Thr Leu Thr Ala Asp Lys Ser Ser Ser
            85                  90                  95

Thr Ala Tyr Met Gln Leu Ser Ser Leu Thr Ser Asp Asp Ser Ala Val
            100                 105                 110

Tyr Phe Cys Ala Arg Asn Trp Met Asn Phe Asp Tyr Trp Gly Gln Gly
            115                 120                 125

Thr Thr Leu Thr Val Ser Ser
130                 135

<210> SEQ ID NO 43
<211> LENGTH: 132
<212> TYPE: PRT
<213> ORGANISM: Mus musculus

<400> SEQUENCE: 43

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Ser
            20                  25                  30

Val Thr Pro Gly Glu Ser Val Ser Ile Ser Cys Arg Ser Ser Lys Ser
            35                  40                  45

Leu Leu His Ser Asn Gly Asn Thr Tyr Leu Tyr Trp Phe Leu Gln Arg
50                  55                  60

Pro Gly Gln Ser Pro Gln Phe Leu Ile Tyr Arg Met Ser Asn Leu Ala
65                  70                  75                  80

```
Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
            115                 120                 125

Leu Glu Ile Lys
    130

<210> SEQ ID NO 44
<211> LENGTH: 462
<212> TYPE: PRT
<213> ORGANISM: Mus musculus

<400> SEQUENCE: 44

Met Gly Trp Ser Leu Ile Leu Phe Leu Val Ala Val Ala Thr Arg
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Ala Phe
         35                  40                  45

Thr Tyr Tyr Leu Ile Glu Trp Val Arg Gln Ala Pro Gly Gln Gly Leu
 50                  55                  60

Glu Trp Ile Gly Val Ile Asn Pro Gly Ser Gly Gly Thr Asn Tyr Asn
 65                  70                  75                  80

Glu Lys Phe Lys Gly Arg Ala Thr Ile Thr Ala Asp Lys Ser Thr Ser
             85                  90                  95

Thr Ala Tyr Met Glu Leu Ser Ser Leu Arg Ser Glu Asp Thr Ala Val
            100                 105                 110

Tyr Phe Cys Ala Arg Asn Trp Met Asn Phe Asp Tyr Trp Gly Gln Gly
            115                 120                 125

Thr Thr Val Thr Val Ser Ser Ala Ser Thr Lys Gly Pro Ser Val Phe
            130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300
```

```
Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Gln Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
                420                 425                 430

Gln Glu Gly Asn Val Phe Ser Cys Ser Val Met His Glu Ala Leu His
            435                 440                 445

Asn His Tyr Thr Gln Lys Ser Leu Ser Leu Ser Leu Gly Lys
        450                 455                 460

<210> SEQ ID NO 45
<211> LENGTH: 239
<212> TYPE: PRT
<213> ORGANISM: Mus musculus

<400> SEQUENCE: 45

Met Arg Val Pro Ala Gln Leu Leu Gly Leu Leu Leu Leu Trp Leu Pro
1               5                   10                  15

Gly Ala Arg Cys Asp Ile Val Met Thr Gln Thr Pro Leu Ser Leu Ser
                20                  25                  30

Val Thr Pro Gly Gln Pro Ala Ser Ile Ser Cys Arg Ser Ser Lys Ser
            35                  40                  45

Leu Leu His Ser Asn Gly Asn Thr Tyr Leu Tyr Trp Phe Leu Gln Lys
        50                  55                  60

Pro Gly Gln Ser Pro Gln Phe Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Met Gln His Leu Glu Tyr Pro Tyr Thr Phe Gly Gly Gly Thr Lys
            115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220
```

```
Gly Leu Ser Ser Pro Val Thr Lys Ser Phe Asn Arg Gly Glu Cys
225                 230                 235
```

ANTIBODIES THAT BIND TO LYSYL OXIDASE-LIKE 2 (LOXL2)

CROSS-REFERENCE TO RELATED APPLICATIONS

The present application claims the benefit of U.S. Provisional Patent Application No. 61/301,550 filed on Feb. 4, 2010, the disclosure of which is incorporated by reference in its entirety for all purposes.

BACKGROUND

Cancer is a serious public health problem in the United States and other developed countries. Currently, one in four deaths in the United States is due to cancer. Cancer therapy involves treating patients with chemotherapeutic drugs to kill tumor cells. However, subsets of tumor cells are frequently resistant to drug therapy and survive to re-populate at sites of origin and at distant metastatic sites, leading to detectable disease recurrence and morbidity. Many carcinoma tumor cells that have the properties of increased invasive and metastatic capacity, and altered drug resistance, are thought to have undergone a morphological transformation encompassing or similar to EMT (epithelial-mesenchymal transition). Cells undergoing EMT lose the normal adhesive properties of epithelial cells and undergo a spectrum of changes including loss of E-cadherin expression and expression of mesenchymal markers, increased motility, increased invasiveness, and increased resistance to cell death.

Lysyl oxidase-type enzymes have been purified from chicken, rat, mouse, bovines and humans. The known lysyl oxidase-type enzymes contain a common catalytic domain, approximately 205 amino acids in length, located in the carboxyl-terminal portion of the protein and containing the active site of the enzyme. The active site contains a copper-binding site which includes a conserved amino acid sequence containing four histidine residues which coordinate a Cu(II) atom. The active site also contains a lysyltyrosyl quinone (LTQ) cofactor, formed by intramolecular covalent linkage between a lysine and a tyrosine residue (corresponding to lys314 and tyr349 in rat lysyl oxidase, and to lys320 and tyr355 in human lysyl oxidase). The sequence surrounding the tyrosine residue that forms the LTQ cofactor is also conserved among lysyl oxidase-type enzymes. The catalytic domain also contains ten conserved cysteine residues, which participate in the formation of five disulfide bonds. The catalytic domain also includes a fibronectin binding domain. Finally, an amino acid sequence similar to a growth factor and cytokine receptor domain, containing four cysteine residues, is present in the catalytic domain.

SUMMARY

The present disclosure provides antibodies that specifically bind a LOXL2 polypeptide; and further provides compositions comprising same. The antibodies can be used in various treatment and diagnostic methods, which are also provided.

Accordingly, the present disclosure comprises, inter alia, the following embodiments.

1. An isolated antibody to lysyl oxidase-like-2 (LOXL2) that specifically binds to an epitope defined by amino acids 325 through 434 of the sequence depicted in FIG. 1 and set forth in SEQ ID NO:1.

2. The isolated antibody of embodiment 1, wherein the epitope comprises amino acids within the sequence TPAM-GLQKK (SEQ ID NO:2).

3. The isolated antibody of embodiment 1, wherein the antibody inhibits enzymatic activity of a LOXL2 polypeptide.

4. The isolated antibody of embodiment 1, wherein the antibody does not inhibit enzymatic activity of a LOXL2 polypeptide.

5. The isolated antibody of embodiment 1, wherein the antibody binds the epitope with an affinity of from about $10^7$ $M^{-1}$ to about $10^{12}$ $M^{-1}$.

6. The isolated antibody of embodiment 1, wherein the antibody comprises a heavy chain, and wherein the heavy chain of the antibody is of the isotype IgG1, IgG2, IgG3, or IgG4.

7. The isolated antibody of embodiment 1, wherein the binding agent is detectably labeled.

8. The isolated antibody of embodiment 1, wherein the antibody is a Fv, scFv, Fab, F(ab')2, or Fab'.

9. The isolated antibody of embodiment 1, wherein the antibody is humanized.

10. The isolated antibody of embodiment 1, wherein the antibody is chimeric.

11. The isolated antibody of embodiment 1, wherein the antibody comprises a covalently linked moiety selected from the group consisting of a non-peptide synthetic polymer, a lipid, a fatty acid, a polysaccharide, a carbohydrate, or a contrast agent.

12. The isolated antibody of embodiment 11, wherein the synthetic polymer is poly(ethylene glycol) polymer.

13. The isolated antibody of embodiment 1, wherein the antibody is immobilized on a solid support.

14. The isolated antibody of embodiment 1, wherein the antibody comprises a cancer chemotherapeutic agent covalently or non-covalently linked to the antibody.

15. A kit for treating a condition associated with LOXL2 comprising
a composition comprising an isolated LOXL2 binding agent of embodiment 1 and
a pharmaceutically acceptable carrier or excipient.

16. The kit of embodiment 15, wherein said condition associated with LOXL2 is a tumor, a metastasis, angiogenesis, or fibrosis.

17. The kit of embodiment 15, wherein the LOXL2 binding agent comprises a detectable label, a therapeutic agent or both.

18. A method of diagnosing a condition associated with LOXL2 comprising:
assessing a level of LOXL2 in a sample of a subject by contacting said sample with an isolated antibody according to embodiment 1,
wherein a change in level of LOXL2 in the sample in comparison with a reference sample indicates the presence of the condition associated with LOXL2.

19. The method of embodiment 18, wherein said condition associated with LOXL2 is a tumor, a metastasis, angiogenesis, or fibrosis.

20. The method of embodiment 19, wherein an increase in LOXL2 levels in the sample in comparison with a reference sample indicates the presence of a tumor or metastasis thereof, or an increase in tumor or metastatic growth.

21. The method of embodiment 20, wherein the reference sample is a sample taken from the subject at an earlier time point or from unaffected tissue of the same type, or is a sample from another individual.

22. The method of embodiment 18, wherein the antibody is detectably labeled.

23. A method of inhibiting LOXL2 activity by contacting a sample or a cellular tissue with an isolated antibody according to embodiment 1.

24. The method of embodiment 23, wherein contacting occurs in vitro or ex vivo.

25. The method of embodiment 23, wherein contacting occurs in vivo.

26. The method of embodiment 23, wherein inhibiting LOXL2 reduces a condition in a subject selected from the group consisting of tumor growth, angiogenesis, and fibrosis.

27. A method of reducing growth of a tumor in a subject, comprising administering the antibody of embodiment 1 to the subject.

28. The method of embodiment 27, wherein said tumor is a primary tumor or a metastatic tumor.

29. The method of embodiment 27, wherein said tumor is a solid tumor.

30. A method of inhibiting angiogenesis in a subject comprising administering the antibody of embodiment 1 to the subject.

31. A method of inhibiting a fibrotic disease in a subject by administering the antibody of embodiment 1 to the subject.

32. A method of monitoring a subject's response to an anti-LOXL2 therapy by detecting LOXL2 levels and/or activity using an antibody according to embodiment 1.

BRIEF DESCRIPTION OF THE DRAWINGS

FIG. 1 shows the amino acid sequence of the human LOXL2 protein (SEQ ID NO:1). The signal peptide sequence (amino acids 1-25), the four scavenger receptor cysteine-rich (SRCR) domains, and the catalytic domain are indicated. SRCR1 extends from amino acids 58-159 inclusive; SRCR2 extends from amino acids 188-302 inclusive, SRCR3 extends from amino acids 325-425 inclusive, SRCR4 extends from amino acids 435-544 inclusive and the catalytic domain extends from amino acids 548-774 inclusive.

FIG. 2, Panel A shows a schematic drawing of the human LOXL2 protein, with the SRCR1, SRCR2, SRCR3 and SRCR4 domains indicated. Also indicated are the catalytic domain (labeled "LOX-like domain"), and the locations of a myc epitope tag and a His6 purification tag (labeled "6×his") that are present in certain synthetic LOXL2 constructs. Below the schematic, the portions of the sequence represented by a collection of domain polypeptides, used in the mapping experiments discussed in Example 4, is shown. See also Table 2.

FIG. 2, Panel B shows the amino acid sequences of the polypeptides shown schematically in FIG. 2, Panel A.

FIG. 4 shows an alignment among the amino acid sequences of the SRCR4 domains from human LOXL2, human LOXL3 and human LOXL4.

FIG. 5 shows an alignment of the amino acid sequences of the catalytic domains of LOXL2 proteins from human (H), mouse (M), rat (R) and *Cynomolgus* monkey (C). Residues in the mouse, rat and *Cynomolgus* protein, which differ from that of the human protein, are indicated by underlining. The two residues at which a single amino acid change from the rat to the human sequence allows the rat protein to be bound by the AB0030 antibody are indicated by asterisks above the sequence.

FIG. 6 provides amino acid sequences of the variable regions of the AB0023 heavy and light chains ($V_H$ and $V_L$, respectively); and the full-length amino acid sequences of the heavy and light chains of AB0024.

DEFINITIONS

Figure 3:
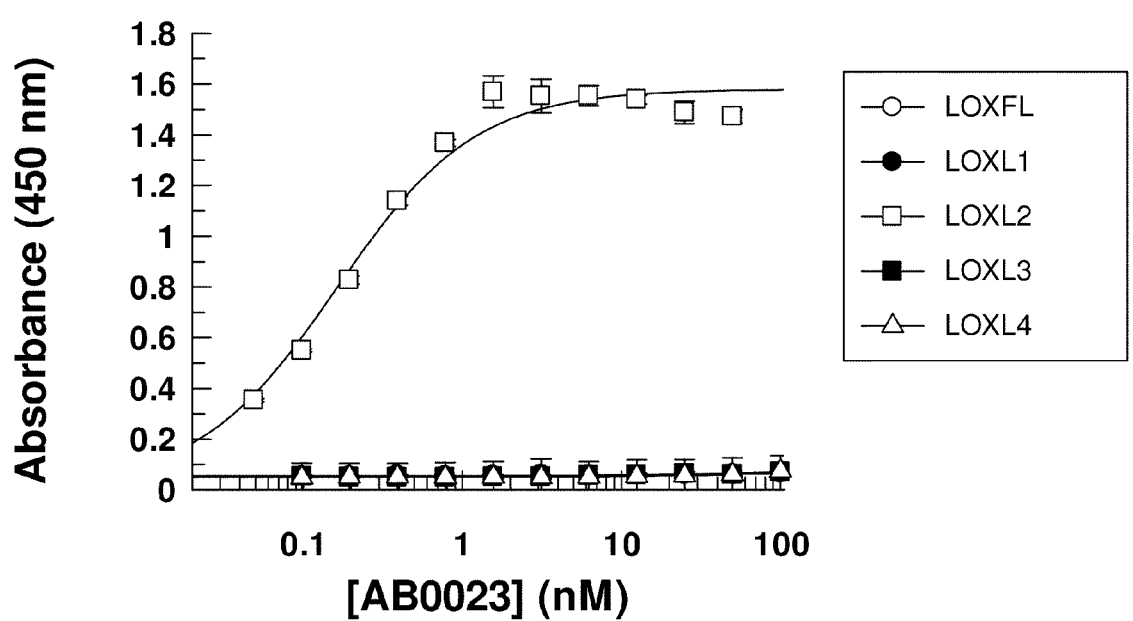
FIG. 3 shows results of ELISA experiments conducted to assess the binding of AB0023 to the different human lysyl oxidase-type proteins (lysyl oxidase, designated "LOXFL" in the figure; LOXL1; LOXL2; LOXL3 and LOXL4). Varying concentrations of the anti-LOXL2 antibody AB0023 were used to probe 1 ug/ml of target protein. Only LOXL2 is bound by the antibody.

As used herein, the term "lysyl oxidase-type enzyme" refers to a member of a family of proteins that catalyzes oxidative deamination of ε-amino groups of lysine and hydroxylysine residues, resulting in conversion of peptidyl lysine to peptidyl-α-aminoadipic-δ-semialdehyde (allysine) and the release of stoichiometric quantities of ammonia and hydrogen peroxide:

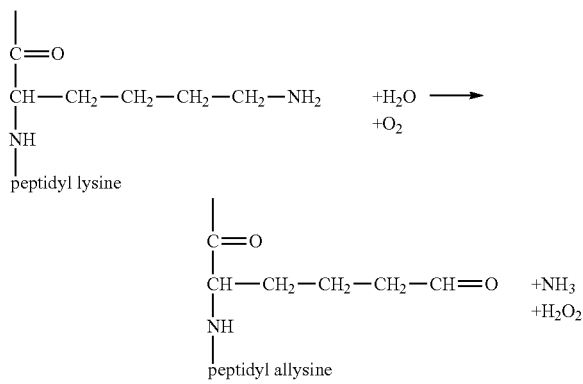

This reaction most often occurs extracellularly, on lysine residues in collagen and elastin. The aldehyde residues of allysine are reactive and can spontaneously condense with other allysine and lysine residues, resulting in crosslinking of collagen molecules to form collagen fibrils.

Lysyl oxidase-type enzymes have been purified from chicken, rat, mouse, bovines and humans. The known lysyl oxidase-type enzymes contain a common catalytic domain, approximately 205 amino acids in length, located in the carboxyl-terminal portion of the protein and containing the active site of the enzyme. The active site contains a copper-binding site which includes a conserved amino acid sequence containing four histidine residues which coordinate a Cu(II) atom. The active site also contains a lysyltyrosyl quinone (LTQ) cofactor, formed by intramolecular covalent linkage between a lysine and a tyrosine residue (corresponding to lys314 and tyr349 in rat lysyl oxidase, and to lys320 and tyr355 in human lysyl oxidase). The sequence surrounding the tyrosine residue that forms the LTQ cofactor is also conserved among lysyl oxidase-type enzymes. The catalytic domain also contains ten conserved cysteine residues, which participate in the formation of five disulfide bonds. The catalytic domain also includes a fibronectin binding domain. Finally, an amino acid sequence similar to a growth factor and cytokine receptor domain, containing four cysteine residues, is present in the catalytic domain.

The first member of this family of enzymes to be isolated and characterized was lysyl oxidase (EC 1.4.3.13); also known as protein-lysine 6-oxidase, protein-L-lysine:oxygen 6-oxidoreductase (deaminating), or LOX. See, e.g., Harris et al., *Biochim. Biophys. Acta* 341:332-344 (1974); Rayton et al., *J. Biol. Chem.* 254:621-626 (1979); Stassen, *Biophys. Acta* 438:49-60 (1976).

Additional lysyl oxidase-type enzymes were subsequently discovered. These proteins have been dubbed "LOX-like," or "LOXL." They all contain the common catalytic domain described above and have similar oxidative lysine deaminase enzymatic activity. Currently, five different lysyl oxidase-type enzymes are known to exist in both humans and mice: LOX and the four LOX related, or LOX-like proteins LOXL1 (also denoted "lysyl oxidase-like," "LOXL" or "LOL"), LOXL2 (also denoted "LOR-1"), LOXL3, and LOXL4. The genes encoding each of the five lysyl oxidase-type enzymes reside on a different chromosome. See, for example, Molnar et al. (2003) *Biochim Biophys Acta.* 1647:220-224; Csiszar (2001) *Prog. Nucl. Acid Res.* 70:1-32; WO 01/83702 published on Nov. 8, 2001, and U.S. Pat. No. 6,300,092, all of which are incorporated by reference herein. A LOX-like protein termed LOXC, with some similarity to LOXL4 but with a different expression pattern, has been isolated from a murine EC cell line. Ito et al. (2001) *J. Biol. Chem.* 276: 24023-24029. Two lysyl oxidase-type enzymes, DmLOXL-1 and DmLOXL-2, have been isolated from *Drosophila*.

Although all lysyl oxidase-type enzymes share a common catalytic domain, they also differ from one another, particularly within their amino-terminal regions. The four LOXL proteins have amino-terminal extensions, compared to LOX. Thus, while human preproLOX (i.e., the primary translation product prior to signal sequence cleavage, see below) contains 417 amino acid residues; LOXL1 contains 574, LOXL2 contains 638, LOXL3 contains 753 and LOXL4 contains 756.

Within their amino-terminal regions, LOXL2, LOXL3 and LOXL4 contain four repeats of the scavenger receptor cysteine-rich (SRCR) domain. These domains are not present in LOX or LOXL1. SRCR domains are found in secreted, transmembrane, or extracellular matrix proteins, and are known to mediate ligand binding in a number of secreted and receptor proteins. Hoheneste et al. (1999) *Nat. Struct. Biol.* 6:228-232; Sasaki et al. (1998) *EMBO J.* 17:1606-1613. In addition to its SRCR domains, LOXL3 contains a nuclear localization signal in its amino-terminal region. A proline-rich domain appears to be unique to LOXL1. Molnar et al. (2003) *Biochim. Biophys. Acta* 1647:220-224. The various lysyl oxidase-type enzymes also differ in their glycosylation patterns.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-Chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

As used herein, the term "affinity" refers to the equilibrium constant for the reversible binding of two agents and is expressed as a dissociation constant (Kd). Affinity of an antibody for a specific antigen can be at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-LOXL2 (e.g., an anti-LOXL2 antibody or antigen-binding fragment) binds specifically to an epitope within a LOXL2 polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

utes. In some embodiments, the antibody will be purified (1) to greater than 95% by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined in which amino acids within a group are exchanged preferentially with each other, and therefore resemble each other most in their impact on the overall protein structure (Schulz, G. E. and R. H. Schirmer, Principles of Protein Structure, Springer-Verlag). Examples of amino acid groups defined in this manner include (i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic non-polar group, consisting of Val, Leu and Ile,
(vii) a slightly-polar group, consisting of Met and Cys,

TABLE 1

CDR Definitions

| (1) | | (2) | Kabat[1] | (3) | Chothia[2] | (4) | MacCallum[3] |
|---|---|---|---|---|---|---|---|
| (5) | $V_H$CDR1 | (6) | 31-35 | (7) | 26-32 | (8) | 30-35 |
| (9) | $V_H$CDR2 | (10) | 50-65 | (11) | 53-55 | (12) | 47-58 |
| (13) | $V_H$CDR3 | (14) | 95-102 | (15) | 96-101 | (16) | 93-101 |
| (17) | $V_L$CDR1 | (18) | 24-34 | (19) | 26-32 | (20) | 30-36 |
| (21) | $V_L$CDR2 | (22) | 50-56 | (23) | 50-52 | (24) | 46-55 |
| (25) | $V_L$CDR3 | (26) | 89-97 | (27) | 91-96 | (28) | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous sol- (viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site is occupied by a similar amino acid residue (e.g., similar in steric and/or electronic nature), then the molecules can be referred to as homologous (similar) at that position. Expression of a percentage of homology/similarity or identity refers to a function of the number of identical or similar amino acids at positions shared by the compared sequences. A sequence which is "unrelated" or "non-homologous" shares less than 40% identity, or less than 25% identity, with a reference sequence. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. A reference amino acid (protein) sequence (e.g., a sequence shown herein) may be used as a "query sequence" to perform a search against public databases to, for example, identify other family members, related sequences or homologs. Such searches can be performed using the NB LAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to a reference nucleic acid. BLAST amino acid searches can be performed with the XBLAST program, score=50, wordlength=3 to obtain amino acid sequences homologous to a reference amino acid sequence. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used (see the world wide web at: ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

The term "substantially identical" means identity between a first amino acid sequence that contains a sufficient or minimum number of amino acid residues that are (i) identical to, or (ii) conservative substitutions of, aligned amino acid residues in a second amino acid sequence such that the first and second amino acid sequences can have a common structural domain and/or common functional activity. For example, amino acid sequences that contain a common structural domain having at least about 90%, 91%, 92%, 93%, 94%, 95%, 96%, 97%, 98% or 99% identity to LOXL2 are termed sufficiently or substantially identical to the LOXL2 polypeptide. In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound (e.g. a subject antibody) that, when administered to a mammal or other subject for treating a disease, is sufficient to effect such treatment for the disease. The "therapeutically effective amount" will vary depending on the antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed embodiments. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art of the disclosure. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the presently-claimed subject matter is not entitled to antedate such publication by virtue of prior invention. Further, the dates of publication provided may be different from the actual publication dates which may need to be independently confirmed.

DETAILED DESCRIPTION

The present disclosure provides lysyl oxidase-like-2 (LOXL2) polypeptide binding agents, i.e., antibodies that specifically bind a LOXL2 polypeptide; and further provides compositions comprising same. The binding agents can be used in various treatment and diagnostic methods, which are also provided.

The present disclosure provides an isolated lysyl oxidase-like-2 (LOXL2) binding agent (i.e., and anti-LOXL2 antibody) that that specifically binds to a LOXL2 epitope, wherein the LOXL2 epitope is defined by amino acids within the amino acid sequence depicted in FIG. 1 (SEQ ID NO:1).

In some embodiments, the epitope bound by a subject anti-LOXL2 antibody can be: 1) defined by amino acids within amino acids 303 to 547 of the amino acid sequence depicted in FIG. 1 and set forth in SEQ ID NO:1; 2) defined by amino acids within amino acids 303 to 425 of the amino acid sequence depicted in FIG. 1 and set forth in SEQ ID NO:1; 3) defined by amino acids within amino acids 325 to 434 of the amino acid sequence depicted in FIG. 1 and set forth in SEQ ID NO:1; 4) defined by amino acids within amino acids 303 to 434 of the amino acid sequence depicted in FIG. 1 and set forth in SEQ ID NO:1; 5) defined by amino acids within amino acids 426 to 547 of the amino acid sequence depicted in FIG. 1 and set forth in SEQ ID NO:1; or 6) defined by amino acids within amino acids 435 to 547 of the amino acid sequence depicted in FIG. 1 and set forth in SEQ ID NO: 1. The epitope bound by a subject anti-LOXL2 antibody can comprise amino acids within the sequence TPAMGLQKK (SEQ ID NO:2).

The epitope bound by a subject anti-LOXL2 antibody can comprise amino acids within the sequence VWGMVCGQNWGIVEAMVVCRQLGLGFASNAFQETWYWHG (SEQ ID NO:3).

In some embodiments, a subject isolated LOXL2 binding agent inhibits enzymatic activity of a LOXL2 polypeptide. In some embodiments, the inhibition is non-competitive. In some embodiments, a subject isolated LOXL2 binding agent does not inhibit enzymatic activity of a LOXL2 polypeptide. In some embodiments, a subject isolated LOXL2 binding agent competes with an AB0023 antibody for binding to a LOXL2 epitope. In some embodiments, a subject isolated LOXL2 binding agent does not compete with an AB0023 antibody for binding to a LOXL2 epitope.

In some embodiments, the epitope bound by a subject anti-LOXL2 antibody can be: 1) defined by amino acids within amino acids 58 to 324 of the amino acid sequence depicted in FIG. 1 and set forth in SEQ ID NO:1; 2) defined by amino acids within amino acids 58 to 159 of the amino acid sequence depicted in FIG. 1 and set forth in SEQ ID NO:1; 3) defined by amino acids within amino acids 58 to 187 of the amino acid sequence depicted in FIG. 1 and set forth in SEQ ID NO:1; 4) defined by amino acids within amino acids 160 to 302 of the amino acid sequence depicted in FIG. 1 and set forth in SEQ ID NO:1; or 5) defined by amino acids within amino acids 188 to 302 of the amino acid sequence depicted in FIG. 1 and set forth in SEQ ID NO:1. In some of these embodiments, the agent inhibits enzymatic activity of a LOXL2 polypeptide. In some embodiments, the inhibition is non-competitive. In some of these embodiments, the agent does not inhibit enzymatic activity of a LOXL2 polypeptide.

In some embodiments, the epitope bound by a subject anti-LOXL2 antibody can be: 1) defined by amino acids within amino acids 546 to 744 of the amino acid sequence depicted in FIG. 1 and set forth in SEQ ID NO:1. In some of these embodiments, the agent inhibits enzymatic activity of a LOXL2 polypeptide. In some embodiments, the inhibition is non-competitive. In some of these embodiments, the agent does not inhibit enzymatic activity of a LOXL2 polypeptide.

In any one of the above embodiments, a subject binding agent binds the epitope with an affinity of from about $10^7$ $M^{-1}$ to about $10^{12}$ $M^{-1}$. In any one of the above embodiments, a subject antibody comprises an immunoglobulin heavy chain, and the heavy chain of the antibody can be of the isotype IgG1, IgG2, IgG3, or IgG4. In any one of the above embodiments, a subject binding agent can be detectably labeled. In any one of the above embodiments, a subject antibody can be a Fv, scFv, Fab, F(ab')$_2$, or Fab'. A subject antibody can be humanized or chimeric.

In any one of the above embodiments, a subject binding agent can be modified. For example, a subject binding agent or a subject antibody: 1) comprises a covalently linked non-peptide synthetic polymer; 2) comprises a poly(ethylene glycol) polymer; 3) comprises a covalently linked lipid or fatty acid moiety; 4) comprises a covalently linked polysaccharide or carbohydrate moiety; 5) comprises a contrast agent; 6) is immobilized on a solid support; 7) is a single chain Fv (scFv) antibody; 8) is a multimerized scFv; or 9) comprises a cancer chemotherapeutic agent covalently or non-covalently linked to the antibody.

The present disclosure provides a kit for treating a condition associated with LOXL2 comprising: a composition comprising an isolated LOXL2 binding agent as described herein; and a pharmaceutically acceptable carrier or excipient. In some embodiments, the condition associated with LOXL2 is a tumor, metastasis, angiogenesis, or fibrosis. In some embodiments, the LOXL2 binding agent comprises a detectable label, a therapeutic moiety or both. In some embodiments, the composition is free of pyrogens. In some embodiments, the composition is lyophilized.

The present disclosure provides a method of diagnosing a condition associated with LOXL2 comprising: assessing a level of LOXL2 in a sample of a subject by contacting said sample with a subject isolated LOXL2 binding agent, wherein a change in level of LOXL2 in the sample in comparison with a reference sample indicates the presence of the condition associated with LOXL2. In some embodiments, the condition associated with LOXL2 is a tumor, metastasis, angiogenesis, or fibrosis. In some embodiments, an increase in LOXL2 levels in the sample in comparison with a reference sample indicates the presence of a tumor or metastasis thereof, or an increase in tumor or metastatic growth. In some embodiments, the reference sample is a sample taken from the subject at an earlier time point or from unaffected tissue of the same type, or is a sample from another individual. In some embodiments, the LOXL2 binding agent is detectably labeled.

The present disclosure provides a method of inhibiting LOXL2 by contacting a sample, a cell, or a tissue with a subject isolated LOXL2 binding agent, i.e., an anti-LOXL2 antibody or an antigen-binding fragment thereof, or by administering a LOXL2 binding agent of the disclosure to a subject. In some embodiments, binding of said agent to LOXL2 inhibits enzymatic activity of LOXL2. In some embodiments, contacting occurs in vitro or ex vivo. In some embodiments, contacting occurs in vivo. In some embodiments, inhibiting LOXL2 reduces tumor growth and/or metastasis in a subject. In some embodiments, inhibiting LOXL2 reduces angiogenesis in a subject. In some embodiments, inhibiting LOXL2 reduces fibrosis in a subject.

The present disclosure provides a method of reducing growth of a tumor in a subject, comprising administering a subject anti-LOXL2 binding agent. In some embodiments, the tumor is a primary tumor or a metastatic tumor. In some embodiments, the tumor is a solid tumor.

The present disclosure provides a method of inhibiting angiogenesis in a subject comprising administering a subject isolated anti-LOXL2 binding agent.

The present disclosure provides a method of inhibiting a fibrotic disease in a subject comprising administering a subject isolated anti-LOXL2 binding agent.

In any one of the above treatment methods, administration or contacting can be by parenteral administration. In any one of the above treatment methods, the method can further comprise co-administering a second therapeutic agent. The second therapeutic agent can be a therapeutic biologic (e.g., an antibody) or a chemotherapeutic agent.

The present disclosure provides a method of monitoring a subject's response to administration of a subject anti-LOXL2 binding agent by detecting LOXL2 levels and/or activity.

In any one of the above-noted methods, the anti-LOXL2 binding agent can be labeled with a detectable label or conjugated, either covalently or non-covalently, to a therapeutic moiety.

LOXL2 Binding Agents

The present disclosure provides agents that bind a region in the LOXL2 polypeptide, referred to generally herein as "LOXL2 polypeptide binding agents," "LOXL2 binding agents," or "anti-LOXL2 binding agents". Anti-LOXL2 binding agents include binding agents that bind a region of LOXL2 and binding agents that inhibit LOXL2 enzymatic activity. Such inhibitory binding agents include agents that act as competitive inhibitors or as noncompetitive inhibitors. Suitable LOXL2 binding agents are anti-LOXL2 antibodies (or antigen-binding fragments thereof).

The present disclosure provides antibodies that specifically bind LOXL2. Such antibodies are also referred to herein as "anti-LOXL2 antibodies." A subject anti-LOXL2 antibody specifically binds an epitope present within a portion of LOXL2, as described in more detail below.

"Epitope" as used herein refers to the contiguous or non-contiguous amino acid residues in a LOXL2 polypeptide which facilitate a binding interaction between the LOXL2 polypeptide and the anti-LOXL2 binding agent. Epitopes bound by an anti-LOXL2 binding agent, such as an anti-LOXL2 antibody, include linear epitopes (e.g., epitopes formed by contiguous stretches of amino acids) and conformational epitopes (e.g., epitopes formed by non-contiguous stretches of amino acids). An epitope specifically bound by an anti-LOXL2 binding agent, such as an anti-LOXL2 antibody, is also referred to herein as a "LOXL2 epitope." A LOXL2 epitope (e.g., residues within a LOXL2 polypeptide that define an epitope) can have a total length of from about 3 amino acids to about 15 amino acids or greater, e.g., a LOXL2 epitope can have a total length of 3 amino acids (aa), 4 aa, 5 aa, 6 aa, 7 aa, 8 aa, 9 aa, 10 aa, 11 aa, 12 aa, 13 aa, 14 aa, 15 aa, 20 aa, 25aa, 30aa, 40aa or 50aa. As noted above, the amino acids that comprise a LOXL2 epitope may be contiguous, or may be non-contiguous.

As illustrated in FIG. 1, an unprocessed LOXL2 polypeptide comprises, in order from amino terminus to carboxyl terminus: a) a signal peptide; b) a first scavenger receptor cysteine-rich (SRCR) domain, referred to herein as SRCR1; c) a second SRCR domain, referred to herein as SRCR2; d) a third SRCR domain, referred to herein as SRCR3; e) a fourth SRCR domain, referred to herein as SRCR4; and f) a catalytic domain. SRCR1 and SRCR2 are joined by 28 amino acids; SRCR2 and SRCR3 are joined by 22 amino acids; and SRCR3 and SRCR4 are joined by 9 amino acids, where the joining amino acids are referred to herein as "linker" amino acids or "linkers." The mature (or processed) form of LOXL2 is generated from the unprocessed form by cleavage between SRCR2 and SRCR3 to release a polypeptide comprising the signal sequence, SRCR1, and SRCR2. Thus, the mature, processed form of LOXL2 comprises, in order from amino terminus to carboxyl terminus: i) SRCR3; ii) linker; iii) SRCR4; iv) linker; and v) catalytic domain.

A LOXL2 polypeptide comprises an amino acid sequence having at least about 90%, at least about 95%, at least about 98%, at least about 99%, or 100%, amino acid sequence identity with a contiguous stretch of from about 400 amino acids (aa) to about 450 aa, from about 450 aa to about 500 aa, from about 500 aa to about 550 aa, from about 550 aa to about 600 aa, from about 600 aa to about 650 aa, from about 650 aa to about 700 aa, from about 700 aa to about 750 aa, or from about 750 aa to about 774 aa, of the amino acid sequence depicted in FIG. 1 (SEQ ID NO:1). As used herein, "LOXL2 polypeptide" includes a human LOXL2 polypeptide.

In some embodiments, a LOXL2 polypeptide comprises an amino acid sequence having at least about 90%, at least about 95%, at least about 98%, at least about 99%, or 100%, amino acid sequence identity with amino acids 1 to 774 of the amino acid sequence depicted in FIG. 1 (SEQ ID NO:1).

In some embodiments, a LOXL2 polypeptide comprises, in order from amino terminus to carboxyl terminus: i) SRCR3; ii) linker; iii) SRCR4; iv) linker; and v) catalytic domain; and comprises an amino acid sequence having at least about 90%, at least about 95%, at least about 98%, at least about 99%, or 100%, amino acid sequence identity with amino acids 325 to 774 of the amino acid sequence depicted in FIG. 1 (SEQ ID NO:1).

In some embodiments, a LOXL2 polypeptide comprises, in order from amino terminus to carboxyl terminus: i) SRCR1; ii) linker; iii) SRCR2; iv) linker; SRCR3; v) linker; vi) SRCR4; vii) linker; and a catalytic domain; and comprises an amino acid sequence having at least about 90%, at least about 95%, at least about 98%, at least about 99%, or 100%, amino acid sequence identity with amino acids 58 to 774 of the amino acid sequence depicted in FIG. 1 (SEQ ID NO:1).

The unprocessed and the mature forms of the LOXL2 polypeptide as depicted in FIG. 1 have about 55% amino acid sequence identity with the unprocessed and mature forms of human LOXL3 and human LOXL4. The SRCR3-4 region of the LOXL2 polypeptide as depicted in FIG. 1 has about 58% to 60% amino acid sequence identity with the SRCR3-4 regions of human LOXL3 and human LOXL4. The SRCR3 region of the LOXL2 polypeptide as depicted in FIG. 1 has about 64% amino acid sequence identity with the SRCR3 region of human LOXL3 and human LOXL4. The SRCR4 region of the LOXL2 polypeptide as depicted in FIG. 1 has about 55% to 57% amino acid sequence identity with the SRCR4 region of human LOXL3 and human LOXL4. The SRCR1-2 region of the LOXL2 polypeptide as depicted in FIG. 1 has about 45% to 48% amino acid sequence identity with the SRCR1-2 region of human LOXL3 and human LOXL4. The SRCR1 region of the LOXL2 polypeptide as depicted in FIG. 1 has about 57% to 59% amino acid sequence identity with the SRCR1 region of human LOXL3 and human LOXL4. The SRCR2 region of the LOXL2 polypeptide as depicted in FIG. 1 has about 39% to 44% amino acid sequence identity with the SRCR2 region of human LOXL3 and human LOXL4. The catalytic domain of the LOXL2 polypeptide as depicted in FIG. 1 has about 65% to 67% amino acid sequence identity with the catalytic domain of human LOXL3 and human LOXL4.

In some embodiments, a subject anti-LOXL2 antibody exhibits inhibitory activity toward LOXL2, e.g., in some embodiments, a subject anti-LOXL2 antibody inhibits enzymatic activity of a LOXL2 polypeptide. In some embodiments, a subject anti-LOXL2 antibody reduces tumor growth and/or metastasis. Thus, e.g., in some embodiments, a subject anti-LOXL2 antibody: 1) specifically binds an epitope present with in a portion of LOXL2; 2) inhibits enzymatic activity of a LOXL2 polypeptide; and 3) reduces tumor growth and/or metastasis. In other embodiments, a subject anti-LOXL2 antibody: 1) specifically binds an epitope present with in a portion of LOXL2; but does not substantially inhibit enzymatic activity of a LOXL2 polypeptide, and does not substantially reduce tumor growth and/or metastasis.

In some embodiments, subject anti-LOXL2 antibody inhibits LOXL-2 enzymatic activity by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the enzymatic activity of the LOXL2 polypeptide in the absence of the agent.

A subject anti-LOXL2 antibody will in some embodiments inhibit enzymatic activity of a LOXL2 polypeptide with a half maximal inhibitory concentration ($IC_{50}$) of from about 1 nM to about 500 nM, or less than 1 nM. For example, in some embodiments, in which a subject anti-LOXL2 antibody inhibits enzymatic activity of a LOXL2 polypeptide, the anti-LOXL2 antibody inhibits the enzymatic activity with an $IC_{50}$ of from about 1 nM to about 10 nM, from about 10 nM to about 50 nM, from about 50 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some embodiments, in which a subject anti-LOXL2 antibody inhibits enzymatic activity of a LOXL2 polypeptide, the anti-LOXL2 antibody inhibits the enzymatic activity with an $IC_{50}$ of less than 1 nM.

Whether an anti-LOXL2 binding agent inhibits enzymatic activity of LOXL2 can be assessed by any suitable method described herein or known in the art. Examples of assay methods suitable for use in determining the effect of a subject anti-LOXL2 antibody on enzymatic activity of a LOXL2 polypeptide are provided in the Examples. A subject anti-LOXL2 antibody can inhibit enzymatic activity of a LOXL2 polypeptide acting on a collagen substrate (e.g., collagen type I).

In some embodiments, a subject anti-LOXL2 antibody does not substantially inhibit enzymatic activity of a LOXL2 polypeptide. For instance, in some embodiments, a subject anti-LOXL2 antibody inhibits enzymatic activity of a LOXL2 polypeptide, if to any detectable degree, by less than about 10%, less than about 5%, less than about 2%, less than about 1%, compared to the enzymatic activity of the LOXL2 polypeptide in the absence of the anti-LOXL2 antibody. Thus, in the discussion below, if a subject anti-LOXL2 antibody is said to exhibit "no inhibition" of enzymatic activity a LOXL2 polypeptide, or if a subject anti-LOXL2 antibody is said to "not inhibit" enzymatic activity a LOXL2 polypeptide, the anti-LOXL2 antibody inhibits enzymatic activity of a LOXL2 polypeptide, if to any detectable degree, by less than about 10%, less than about 5%, less than about 2%, less than about 1%, compared to the enzymatic activity of the LOXL2 polypeptide in the absence of the anti-LOXL2 antibody.

In some embodiments, a subject antibody reduces tumor growth and/or metastasis. In some embodiments, a subject antibody reduces the incidence of metastasis relative to that observed in the absence of the antibody and, in further testing, inhibits metastatic tumor growth. Tumor inhibition can be quantified using any convenient method of measurement. The incidence of metastasis can be assessed by examining relative dissemination (e.g., number of organ systems involved) and relative tumor burden in these sites. Metastatic growth can be ascertained by microscopic or macroscopic analysis, as appropriate. Tumor metastasis can be reduced by about 10%, 20%, 30%, 40%, 50%, 60%, 70%, 80%, 90%, 95% or greater. In some embodiments, the antibody can be assessed relative to other antibodies or compounds that do not reduce LOXL2 enzymatic activity. The test antibodies can be administered at the time of tumor inoculation, after the establishment of primary tumor growth, or after the establishment of local and/or distant metastases. Single or multiple administration of the test antibody can be given using any convenient mode of administration including, but not limited to, intravenous, intraperitoneal, intratumoral, subcutaneous and intradermal.

A subject anti-LOXL2 antibody exhibits high affinity binding to an epitope within a LOXL2 polypeptide. For example, a subject antibody binds to an epitope within a LOXL2 polypeptide with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on a LOXL2 polypeptide with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

For example, in some embodiments, a subject anti-LOXL2 antibody specifically binds to a LOXL2 polypeptide (e.g., a human LOXL2 polypeptide) with a dissociation constant (Kd) equal to or lower than about 100 nM, lower than about 10 nM, lower than about 1 nM, lower than about 0.5 nM, lower than about 0.1 nM, lower than about 0.01 nM, or lower than about 0.005 nM, measured at a temperature of about 4° C., 25° C., 37° C. or 42° C.

In some embodiments, a subject anti-LOXL2 antibody is of the isotype IgG1, IgG2, IgG3, or IgG4. In some embodiments, a subject anti-LOXL2 antibody is an IgG4 isotype. In some embodiments, the antibody comprises a Ser-to-Pro substitution at amino acid 241 of the heavy chain: See, e.g., Angal et al. (1993) *Molec. Immunol.* 30:105.

LOXL2 Binding Agents that Bind an Epitope within the SRCR3-Linker-SRCR4 Region

In some embodiments, a subject anti-LOXL2 antibody specifically binds an epitope within the SRCR3-linker-SRCR4 region, where such region is referred to as "SRCR3-4." An SRCR3-4 region can comprise an amino acid sequence that has at least about 90%, at least about 95%, at least about 98%, at least about 99%, or 100%, amino acid sequence identity with amino acids 325 to 544, with amino acids 325 to 547, with amino acids 303 to 544, or with amino acids 303 to 547, of SEQ ID NO:1. Thus, e.g., in some embodiments, a subject anti-LOXL2 antibody specifically binds an epitope within an amino acid sequence that has at least about 90%, at least about 95%, at least about 98%, at least about 99%, or 100%, amino acid sequence identity with amino acids 325 to 544, with amino acids 325 to 547, with amino acids 303 to 544, or with amino acids 303 to 547, of SEQ ID NO:1.

A subject anti-LOXL2 antibody will in some instances compete for binding with an AB0023 antibody as described in WO 2009/035791 and US 2009/0053224, and/or AB0024, a counterpart to the AB0023 antibody that includes human framework (FR) sequences, as described in WO 2009/035791 and US 2009/0053224. An AB0023 and an AB0024 antibody as described in WO 2009/035791 and US 2009/0053224 are referred to herein as "AB0023" and "AB0024," respectively. In some embodiments, a subject anti-LOXL2 antibody: a) specifically binds an epitope within SRCR3-4; and ii) competes with an AB0023 antibody and/or an AB0024 antibody for binding to an epitope within SRCR3-4. Amino acid sequences from AB0023 and AB0024 are depicted in FIG. 6.

A subject anti-LOXL2 antibody that competes with an AB0023 antibody and/or an AB0024 antibody for binding to an epitope within SRCR3-4 will in some embodiments bind the same epitope as AB0023 and AB0024. A subject anti-LOXL2 antibody that competes with an AB0023 antibody and/or an AB0024 antibody for binding to an epitope within SRCR3-4 will in some embodiments bind an epitope that overlaps with the epitope bound by AB0023 and AB0024. A subject anti-LOXL2 antibody that competes with an AB0023 antibody and/or an AB0024 antibody for binding to an epitope within SRCR3-4 will in some embodiments bind an epitope that is non-overlapping with the epitope bound by AB0023 and AB0024; such inhibition can be due, for example, to steric hindrance of binding of AB0023 or AB0024 to their epitope when a subject anti-LOXL2 is already bound to its epitope within the SRCR3-4 region, or to an allosteric change in the epitope bound by AB0023 and AB0024 induced by binding of the anti-LOXL2 to its epitope.

As noted above, in some embodiments, a subject anti-LOXL2 antibody inhibits enzymatic activity of a LOXL2 polypeptide. Thus, in some embodiments, a subject anti-LOXL2 antibody: a) specifically binds an epitope within SRCR3-4; and b) inhibits LOXL2 enzymatic activity. In some embodiments, a subject anti-LOXL2 antibody: a) specifically binds an epitope within SRCR3-4; b) inhibits LOXL2 enzymatic activity; and c) competes with an AB0023 antibody and/or an AB0024 antibody for binding to an epitope within SRCR3-4. In other embodiments, a subject anti-LOXL2 antibody: a) specifically binds an epitope within SRCR3-4; b) inhibits LOXL2 enzymatic activity; and c) does not compete with an AB0023 antibody and/or an AB0024 antibody for binding to an epitope within SRCR3-4.

In certain embodiments, an AB0023 antibody and an AB0024 antibody are specifically excluded.

In other embodiments, a subject anti-LOXL2 antibody: a) specifically binds an epitope within SRCR3-4; and ii) does not compete with an AB0023 antibody and/or an AB0024 antibody for binding to an epitope within SRCR3-4.

In some embodiments, a subject anti-LOXL2 antibody comprises a $V_H$ and a $V_L$ region, where: 1) the $V_H$ region comprises one, two, or three heavy chain variable region CDRs comprising an amino acid sequence that is 85%, 86%, 87%, 88%, 89%, 90%, 91%, 92%, 93%, 94%, 95%, 96%, 97%, 98% or 99% identical to an AB0023 heavy chain variable region CDR: and 2) the $V_L$ region comprises one, two, or three light chain variable region CDRs comprising an amino acid sequence that is 85%, 86%, 87%, 88%, 89%, 90%, 91%, 92%, 93%, 94%, 95%. 96%, 97%, 98% or 99% identical to an AB0023 light chain variable region CDR.

Epitopes within the Linker-SRCR3-Linker-SRCR4-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 544, amino acids 303 to 545, amino acids 303 to 546, or amino acids 303 to 547 of SEQ ID NO:1; b) does not inhibit LOXL2 enzymatic activity; and c) does not compete with an AB0023 antibody and/or an AB0024 antibody for binding to an epitope within SRCR3-4.

Epitopes within SRCR3-Linker-SRCR4-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 544, amino acids 325 to 545, amino acids 325 to 546, or amino acids 325 to 547, of SEQ ID NO:1; b) does not inhibit LOXL2 enzymatic activity; and c) does not compete with an AB0023 antibody and/or an AB0024 antibody for binding to an epitope within SRCR3-4.

Epitopes within the Linker-SRCR3-Linker Region

In certain embodiments, a subject anti-LOXL2 antibody specifically binds an epitope within the SRCR3 region (and not within SRCR4). An SRCR3 region can comprise an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO: 1. Thus, e.g., in some embodiments, a subject anti-LOXL2 antibody specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) does not inhibit LOXL2 enzymatic activity; and c) does not compete with an AB0023 antibody and/or an AB0024 antibody for binding to an epitope within SRCR3-4.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 425, with amino acids 303 to 425, with amino acids 303 to 434, or with amino acids 325 to 434, of SEQ ID NO:1; b) does not inhibit LOXL2 enzymatic activity; and c) does not compete with an AB0023 antibody and/or an AB0024 antibody for binding to an epitope within SRCR3-4.

Epitopes within the Linker-SRCR3 Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 303 to 425 of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of t SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of SEQ ID NO:1; b) does not inhibit LOXL2 enzymatic activity; and c) competes with an AB0023 antibody and/or an AB0024 antibody for binding to an epitope within SRCR3-4, e.g. i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 425 of SEQ ID NO:1; b) does not inhibit LOXL2 enzymatic activity; and c) does not compete with an AB0023 antibody and/or an AB0024 antibody for binding to an epitope within SRCR3-4.

Epitopes within SRCR3-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 325 to 434 of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 325 to 434 of SEQ ID NO:1; b) does not inhibit LOXL2 enzymatic activity; and c) does not compete with an AB0023 antibody and/or an AB0024 antibody for binding to an epitope within SRCR3-4.

Epitopes within the Linker-SRCR3-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 303 to 434 of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 303 to 434 of SEQ ID NO:1; b) does not inhibit LOXL2 enzymatic activity; and c) does not compete with an AB0023 antibody and/or an AB0024 antibody for binding to an epitope within SRCR3-4.

Epitopes within the Linker-SRCR4-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically hinds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 426 to 544, amino acids 426 to 545, amino acids 426 to 546, or amino acids 426 to 547, of SEQ ID NO:1; b) does not inhibit LOXL2 enzymatic activity; and c) does not compete with an AB0023 antibody and/or an AB0024 antibody for binding to an epitope within SRCR3-4.

Epitopes within the SRCR4-Linker Region

In certain embodiments, a subject anti-LOXL2 antibody specifically binds an epitope within the SRCR4 region (and not within SRCR3). An SRCR4 region can comprise an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1. Thus, e.g., in some embodiments, a subject anti-LOXL2 antibody specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 435 to 544, amino acids 435 to 545, amino acids 435 to 546, or with amino acids 435 to 547, of SEQ ID NO:1; b) does not inhibit LOXL2 enzymatic activity; and c) does not compete with an AB0023 antibody and/or an AB0024 antibody for binding to an epitope within SRCR3-4.

Epitopes within the Linker Between SRCR3 and SRCR4

In certain instances, a subject anti-LOXL2 antibody specifically binds an epitope that includes amino acids in the linker region between SRCR3 and SRCR4. The linker region between SRCR3 and SRCR4 can comprise an amino acid sequence that has at least about 90%, at least about 95%, at least about 98%, at least about 99%, or 100%, amino acid sequence identity with the following amino acid sequence: TPAMGLQKK (SEQ ID NO:2). Thus, e.g. in some embodiments, a subject anti-LOXL2 antibody specifically binds an epitope within an amino acid sequence that has at least about 90%, at least about 95%, at least about 98%, at least about 99%, or 100%, amino acid sequence identity with SEQ ID NO:2.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:2; b) does not inhibit LOXL2 enzymatic activity; and c) does not compete with an AB0023 antibody and/or an AB0024 antibody for binding to an epitope within SRCR3-4.

Epitopes within Amino Acids 459-497 of LOXL2

In certain instances, a subject anti-LOXL2 antibody specifically binds an epitope within amino acids 459 to 497 of SRCR4. Thus, e.g., in some embodiments, a subject anti-LOXL2 antibody specifically binds an epitope within an amino acid sequence that has at least about 90%, at least about 95%, at least about 98%, at least about 99%, or 100%, amino acid sequence identity with the amino acid sequence:

(SEQ ID NO: 3)
VWGMVCGQNWGIVEAMVVCRQLGLGFASNAFQETWYWHG.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:3; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:3; b) inhibits LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

c) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:3; b) inhibits LOXL2 enzymatic activity; and c) does not compete with an AB0023 antibody and/or an AB0024 antibody for binding to an epitope within SRCR3-4.

d) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:3; and b) does not inhibit LOXL2 enzymatic activity.

e) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:3; b) does not inhibit LOXL2 enzymatic activity; and c) competes with an AB0023 antibody and/or an AB0024 antibody for binding to an epitope within SRCR3-4, e.g., i) binds to the same epitope as the AB0023 antibody; ii) binds to an epitope that is overlapping with the epitope bound by the AB0023 antibody; or iii) binds to an epitope that is non-overlapping with the epitope bound by the AB0023 antibody.

f) In certain embodiments, a subject anti-LOXL2 antibody: a) specifically binds an epitope within an amino acid sequence that has at least about 90%, at least about 95%, at least about 98%, at least about 99%, or 100%, amino acid sequence identity SEQ ID NO:3; b) does not inhibit LOXL2 enzymatic activity; and c) does not compete with an AB0023 antibody and/or an AB0024 antibody for binding to an epitope within SRCR3-4.

In certain embodiments, an antibody that binds an epitope within the amino acid sequence VWGMVCGQN-WGIVEAMVVCRQLGLGFASNAFQETWYWHG (SEQ ID NO:3) is specifically excluded.

LOXL2 Binding Agents that Bind an Epitope within SRCR1-2

In some embodiments, a LOXL2 binding agent, such as a subject anti-LOXL2 antibody, specifically binds an epitope within the SRCR1-linker-SRCR2 region, where such region is referred to as "SRCR1-2." An SRCR1-2 region can comprise an amino acid sequence that has at least about 90%, at least about 95%, at least about 98%, at least about 99%, or 100%, amino acid sequence identity with amino acids 58 to 302, or 58 to 324, of the amino acid sequence depicted in FIG. 1. Thus, e.g., in some embodiments, a subject anti-LOXL2 antibody specifically binds an epitope within an amino acid sequence that has at least about 90%, at least about 95%, at least about 98%, at least about 99%, or 100%, amino acid sequence identity with amino acids 58 to 302, or 58 to 324 of the amino acid sequence depicted in FIG. 1.

Epitopes within the SRCR1-Linker-SRCR2-Linker Region

In certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 58 to 324 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 324 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 324 of the amino acid sequence depicted in FIG. 1; and b) does not inhibit LOXL2 enzymatic activity.

Epitopes within SRCR1

In certain embodiments, a subject anti-LOXL2 antibody specifically binds an epitope within the SRCR1 region (and not within SRCR2). An SRCR1 region can comprise an amino acid sequence that has at least about 90%, at least about 95%, at least about 98%, at least about 99%, or 100%, amino acid sequence identity with amino acids 58 to 159 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 58 to 159 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 159 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 159 of the amino acid sequence depicted in FIG. 1; and b) does not inhibit LOXL2 enzymatic activity.

Epitopes within SRCR1-Linker

In certain embodiments, a subject anti-LOXL2 antibody specifically binds an epitope within the SRCR1-linker region. An SRCR1-linker region can comprise an amino acid sequence that has at least about 90%, at least about 95%, at least about 98%, at least about 99%, or 100%, amino acid sequence identity with amino acids 58 to 187 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 58 to 187 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 187 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 187 of the amino acid sequence depicted in FIG. 1; and b) does not inhibit LOXL2 enzymatic activity.

Epitopes within SRCR2

In certain embodiments, a subject anti-LOXL2 antibody specifically binds an epitope within the SRCR1 region (and not within SRC2). An SRCR2 region can comprise an amino acid sequence that has at least about 90%, at least about 95%, at least about 98%, at least about 99%, or 100%, amino acid sequence identity with amino acids 188 to 302 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 188 to 302 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 188 to 302 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 188 to 302 of the amino acid sequence depicted in FIG. 1; and b) does not inhibit LOXL2 enzymatic activity.

Epitopes within the Linker-SRCR2 Region

In certain embodiments, a subject anti-LOXL2 antibody specifically binds an epitope within the linker-SRCR2 region. A linker-SRCR2 region can comprise an amino acid sequence that has at least about 90%, at least about 95%, at least about 98%, at least about 99%, or 100%, amino acid sequence identity with amino acids 160 to 302 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 160 to 302 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 160 to 302 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 160 to 302 of the amino acid sequence depicted in FIG. 1; and b) does not inhibit LOXL2 enzymatic activity.

Epitopes within the SRCR2-Linker Region

In certain embodiments, a subject anti-LOXL2 antibody specifically binds an epitope within the SRCR2-linker region. An SRCR2-linker region can comprise an amino acid sequence that has at least about 90%, at least about 95%, at least about 98%, at least about 99%, or 100%, amino acid sequence identity with amino acids 188 to 324 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 188 to 324 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 188 to 324 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 188 to 324 of the amino acid sequence depicted in FIG. 1; and b) does not inhibit LOXL2 enzymatic activity.

Epitopes within the Linker-SRCR2-Linker Region

In certain embodiments, a subject anti-LOXL2 antibody specifically binds an epitope within the linker-SRCR2-linker region. A linker-SRCR2-linker region can comprise an amino acid sequence that has at least about 90%, at least about 95%, at least about 98%, at least about 99%, or 100%, amino acid sequence identity with amino acids 160 to 324 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 160 to 324 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 160 to 324 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 160 to 324 of the amino acid sequence depicted in FIG. 1; and b) does not inhibit LOXL2 enzymatic activity.

Epitopes within SRCR1-Linker-SRCR2 Region

In certain embodiments, a subject anti-LOXL2 antibody specifically binds an epitope within the SRCR1-linker-SRCR2 region. An SRCR1-linker-SRCR2 region can comprise an amino acid sequence that has at least about 90%, at least about 95%, at least about 98%, at least about 99%, or 100%, amino acid sequence identity with amino acids 58 to 302 of the amino acid sequence depicted in FIG. 1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 58 to 302 of the amino acid sequence depicted in FIG. 1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 302 of the amino acid sequence depicted in FIG. 1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 58 to 302 of the amino acid sequence depicted in FIG. 1; and b) does not inhibit LOXL2 enzymatic activity.

LOXL2 Binding Agents that Bind an Epitope within the Catalytic Domain

In some embodiments, a subject anti-LOXL2 antibody binds to an epitope within the catalytic domain of a LOXL2 polypeptide. A LOXL2 polypeptide catalytic domain can comprise an amino acid sequence that has at least about 90%, at least about 95%, at least about 98%, at least about 99%, or 100%, amino acid sequence identity with amino acids 546 to 774 of SEQ ID NO:1. Thus, e.g., in certain embodiments, a subject anti-LOXL2 antibody specifically binds an epitope within an amino acid sequence that has at least about 90%, at least about 95%, at least about 98%, at least about 99%, or 100%, amino acid sequence identity with amino acids 546 to 774 of SEQ ID NO:1.

a) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with amino acids 546 to 774 of SEQ ID NO:1; and b) inhibits LOXL2 enzymatic activity.

b) In certain embodiments, a subject anti-LOXL2 antibody: a) specifically binds an epitope within an amino acid sequence that has at least about 90%, at least about 95%, at least about 98%, at least about 99%, or 100%, amino acid sequence identity with SEQ ID NO:1; and b) does not inhibit LOXL2 enzymatic activity.

In certain embodiments, an antibody that binds an epitope that includes tyrosine. 593 (Y593) and/or histidine 739 (H739) of SEQ ID NO:1 is specifically excluded.

Modifications

A subject anti-LOXL2 antibody can comprise one or more modifications, as described below.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally-occurring amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for disclosure of exemplary non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally occurring amino acid" refers to an amino acid that is not one of the 20 common amino acids, or pyrolysine or selenocysteine. Other terms that may be used synonymously with the term "non-naturally occurring amino acid" are "non-natural amino acid," "unnatural amino acid," "non-naturally-encoded amino acid," and variously hyphenated and non-hyphenated versions thereof. The term "non-naturally occurring amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O— phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, acetonitrile butadiene styrene (ABS) resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly (propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50,000 Da, e.g., from 5,000 Da to 40,000 Da, or from 25,000 to 40,000 Da. For example, in some embodiments, in which a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O—CH_2—CH_2)_nO—R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives include, for example, those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., can comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable labels include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horseradish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, wherein the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (Gd-DTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody.

See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP. Many such GFP are available commercially, e.g., from Clontech, Inc. Additional fluorescent proteins include a red fluorescent protein; a yellow fluorescent protein; and any of a variety of fluorescent and colored proteins from Anthozoan species, as described in, e.g., Matz et al. (1999) *Nature Biotechnol.* 17:969-973; and the like.

A subject antibody will in some embodiments be linked (e.g., covalently or non-covalently linked) to a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification such as polyhistidine sequences, e.g., 6His (HHHHHH, SEQ ID NO:4), and the like; provide for secretion of the fusion protein from a cell; provide an epitope tag, e.g., GST, hemagglutinin (HA; e.g., CYPYDVPDYA; SEQ ID NO:5), FLAG (e.g., DYKDDDDK; SEQ ID NO:6), c-myc (e.g., CEQKLISEEDL; SEQ ID NO:7), and the like; provide a detectable signal, e.g., an enzyme that generates a detectable product (e.g., β-galactosidase, luciferase, beta-glucuronidase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:/8), HisX6 (HHHHHH) (SEQ ID NO:4), C-myc (EQKLISEEDL) (SEQ ID NO:7), Flag (DYKDDDDK) (SEQ ID NO:6), StrepTag (WSHPQFEK) (SEQ ID NO:9), hemagglutinin, e.g., HA Tag (YPYDVPDYA; SEQ ID NO:10), glutathinone-S-transferase (GST), thioredoxin, cellulose binding domain, RYIRS (SEQ ID NO:11), Phe-His-His-Thr (SEQ ID NO:12), chitin binding domain, S-peptide, T7 peptide, SH2 domain, C-end RNA tag, WEAAAREACCRECCARA (SEQ ID NO:13), metal binding domains, e.g., zinc binding domains or calcium binding domains such as those from calcium-binding proteins, e.g., calmodulin, troponin C, calcineurin B, myosin light chain, recoverin, S-modulin, visinin, visinin-like protein, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor. Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, ($C_1$-$C_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a $C_3$-$C_{16}$ long-chain aliphatic lipid; and the like. See, e.g., U.S. Pat. No. 6,638,513. In some embodiments, a subject antibody is incorporated into a liposome.

In some embodiments, a subject anti-LOLX2 antibody is conjugated or linked to a therapeutic and/or imaging/detectable moiety. Methods for conjugating or linking antibodies are well known in the art. Associations between antibodies and labels include any means known in the art including, but not limited to, covalent and non-covalent interactions.

In one non-limiting embodiment, a subject anti-LOLX2 antibody can be associated with a toxin, a radionuclide, an iron-related compound, a dye, an imaging reagent, a fluorescent label or a chemotherapeutic agent that would be toxic when delivered to a cancer cell. Alternatively, a subject anti-LOLX2 antibody can be associated with detectable label, such as a radionuclide, iron-related compound, a dye, an imaging agent or a fluorescent agent for immunodetection of target antigens.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{77}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Ho$, $^{169}Eu$, $^{177}Lu$, $^{186}Re$, $^{188}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$, and $^{213}Bi$.

Non-limiting examples of toxins include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, tricothecenes, *Clostridium perfringens* phospholipase C (PLC), bovine pancreatic ribonuclease (BPR), antiviral protein (PAP), abrin, cobra venom factor (CVF), gelonin (GEL), saporin (SAP), and viscumin.

Non-limiting examples of iron-related compounds include, for example, magnetic iron-oxide particles, ferric or ferrous particles, $Fe^{203}$ and $Fe^{304}$. Iron-related compounds and Methods of labeling polypeptides, proteins and peptides can be found, for example, in U.S. Pat. Nos. 4,101,435 and 4,452,773, and U.S. published applications 20020064502 and 20020136693.

In certain embodiments, a subject antibody can be covalently or non-covalently coupled to a cytotoxin or other cell proliferation inhibiting compound, in order to localize delivery of that agent to a tumor cell. For instance, the agent can be selected from: alkylating agents, enzyme inhibitors, proliferation inhibitors, lytic agents, DNA- or RNA-synthesis inhibitors, membrane permeability modifiers, DNA metabolites, dichloroethylsulfide derivatives, protein production inhibitors, ribosome inhibitors, inducers of apoptosis, and neurotoxins.

In certain embodiments, the subject antibodies can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanospheres; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality/moiety will be relatively large, e.g., at least 25 atomic mass units (amu) in size, and in many instances can be at least 50,100 or 250 amu in size.

In certain embodiments, the secondary functionality is a chelate moiety for chelating a metal, e.g., a chelator for a radiometal or paramagnetic ion. In additional embodiments, it is a chelator for a radionuclide useful for radiotherapy or imaging procedures. Conditions under which a chelator will coordinate a metal are described, for example, by Gasnow et al. U.S. Pat. Nos. 4,831,175, 4,454,106 and 4,472,509, each of which is incorporated herein by reference. As used herein, "radionuclide" and "radiolabel" are interchangeable.

Radionuclides suitable for inclusion in a subject anti-LOXL2 antibody include gamma-emitters, positron-emitters, Auger electron-emitters, X-ray emitters and fluorescence-emitters. In some embodiments, beta- or alpha-emitters are used. Examples of radionuclides useful as toxins in radiation therapy include: $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81}MKr$, $^{87}MSr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Exemplary therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$, $^{166}Ho$ or $^{177}Lu$.

$^{99}Tc$ is a particularly attractive radioisotope for diagnostic applications, as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain embodiments, a subject antibody is modified to include a chelating agent for technium.

In still other embodiments, the secondary functionality can be a radiosensitizing agent, e.g., a moiety that increases the sensitivity of cells to radiation. Examples of radiosensitizing agents include nitroimidazoles, metronidazole and misonidazole (see: DeVita, V. T. in Harrison's Principles of Internal Medicine, p. 68, McGraw-Hill Book Co., NY, 1983, which is incorporated herein by reference). The modified antibodies that comprise a radiosensitizing agent as the active moiety are administered and localize at the target cell. Upon exposure of the individual to radiation, the radiosensitizing agent is "excited" and causes the death of the cell.

There is a wide range of moieties which can serve as chelators and which can be derivatized to a subject antibody. For instance, the chelator can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to subject antagonists. Such groups include, e.g., benzylisothiocyanate, by which the DOTA, DTPA or EDTA can be coupled to, e.g., an amine group.

In one embodiment, the chelate moiety is an "NxSy" chelate moiety. As defined herein, the "NxSy chelates" include bifunctional chelators that are capable of coordinately binding a metal or radiometal and, may have N2S2 or N3S cores. Exemplary NxSy chelates are described, e.g., in Fritzberg et al. (1998) PNAS 85: 4024-29; and Weber et al. (1990) Chem. 1: 431-37; and in the references cited therein.

In some embodiments, a subject anti-LOXL2 antibody is modified to include a chemotherapeutic agent, e.g., a chemotherapeutic agent is covalently or non-covalently linked to a subject anti-LOXL2 antibody.

Chemotherapeutic agents ("chemotherapeutics") suitable for use in modifying a subject antibody include small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known cytotoxic agents suitable for use are listed, for example, in Goodman et al., "The Pharmacological Basis of Therapeutics," Sixth Edition, A. B. Gilman et al., eds./Macmillan Publishing Co. New York, 1980. These include taxanes, such as paclitaxel and docetaxel; nitrogen such as mechlorethamine, melphalan, uracil mustard and chlorambucil; ethylenimine derivatives, such as thiotepa; alkyl sulfonates, such as busulfan; nitrosoureas, such as lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, and mitomycin; enzymes, such as platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, acetate and megestrol acetate), estrogens (diethylstilbestrol and ethinyl estradiol), and androgens (testosterone propionate and fluoxymesterone).

In some embodiments, a subject anti-LOXL2 antibody is modified to include a chemotherapeutic agent that interferes with protein synthesis. Drugs that interfere with protein synthesis include, e.g., puromycin, cycloheximide, and ribonuclease.

Most of the chemotherapeutic agents currently in use in treating cancer possess functional groups that are amenable to chemical cross-linking directly with an amine or carboxyl group of a subject antibody. For example, free amino groups are available on methotrexate, doxorubicin, daunorubicin, cytosinarabinoside, bleomycin, fludarabine, and cladribine while free carboxylic acid groups are available on methotrexate, melphalan and chlorambucil.

These functional groups, that is free amino and carboxyl groups, are targets for a variety of homobifunctional and heterobifunctional chemical cross-linking agents which can crosslink these drugs directly to, e.g., a free amino group of a subject antibody.

Chemotherapeutic agents contemplated for modification of a subject antibody also include other chemotherapeutic drugs that are commercially available. Merely to illustrate, the chemotherapeutic can be an inhibitor of chromatin function, a DNA damaging agent, an antimetabolite (such as folate antagonists, pyrimidine analogs, purine analogs, and sugar-modified analogs), a DNA synthesis inhibitor, a DNA interactive agent (such as an intercalating agent), or a DNA repair inhibitor.

Chemotherapeutic agents may be categorized by their mechanism of action into, for example, the following groups: anti-metabolites/anti-cancer agents, such as pyrimidine analogs (floxuridine, capecitabine, and cytarabine) and purine analogs; folate antagonists and related inhibitors; antiproliferative/antimitotic agents including natural products such as vinca alkaloid (vinblastine, vincristine, and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, triethylenethiophosphoramide and etoposide; antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; anti migratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin. Preferred dosages of the chemotherapeutic agents are consistent with currently prescribed dosages.

As used herein, the terms "nucleic acid damaging treatment" and "nucleic acid damaging agent" refer to any treatment regimen that directly or indirectly damages nucleic acid (e.g., DNA, cDNA, genomic DNA, mRNA, tRNA or rRNA). Examples of such agents include alkylating agents, nitrosoureas, anti-metabolites, plant alkaloids, plant extracts and radioisotopes. Examples of agents also include nucleic acid damaging drugs, for example, 5-fluorouracil (5-FU), capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathioputrine, thioguanine), gemcitabine hydrochloride (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubibcin (Cerubicine), idarubicin (Idamycin) and epirubicin (Ellence), anthracyclin analogues such as mitoxantrone, actinomycin D, non intercalating topoisomerase inhibitors such as epipodophyllotoxins (etoposide=VP16, teniposide=VM-26), podophylotoxin, bleomycin (Bleo), pepleomycin, compounds that form adducts with nucleic acid including platinum derivatives (e.g., cisplatin (CDDP), trans analogue of cisplatin, carboplatin, iproplatin, tetraplatin and oxaliplatin), camptothecin, topotecan, irinotecan (CPT-11), and SN-38. Specific examples of nucleic acid damaging treatments include radiation (e.g., focused microwaves, ultraviolet (UV), infrared (IR), or alpha-, beta- or gamma-radiation) and environmental shock (e.g., hyperthermia).

As used herein, the terms "anti-proliferative treatment" and "anti-proliferative agent" means any treatment regimen that directly or indirectly inhibits proliferation of a cell, virus, bacteria or other unicellular or multicellular organism regardless of whether or not the treatment or agent damages nucleic acid. Particular examples of anti-proliferative agents are anti-tumor and anti-viral drugs, which inhibit cell proliferation or virus proliferation or replication. Examples include, inter alia, cyclophosphamide, azathioprine, cyclosporin A, prednisolone, melphalan, chlorambucil, mechlorethamine, busulphan, methotrexate, 6-mercaptopurine, thioguanine, cytosine arabinoside, taxol, vinblastine, vincristine, doxorubicin, actinomycin D, mithramycin, carmustine, lomustine, semustine, streptozotocin, hydroxyurea, cisplatin, mitotane, procarbazine, dacarbazine and dibromomannitol. Anti proliferative agents that cause nucleic acid replication errors or inhibit nucleic acid replication are those such as nucleoside and nucleotide analogues (e.g., AZT or 5-AZC).

In another embodiment, a subject anti-LOXL2 antibody can be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionuclide).

Methods of Producing Antibodies

A subject antibody can be produced by any known method, e.g., conventional synthetic methods for protein synthesis; recombinant DNA methods; etc.

For those embodiments in which a subject antibody is a single chain polypeptide, it can synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med. Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase-attached peptide is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the genetic code, a variety of nucleic acid sequences can encode each immunoglobulin amino acid sequence. The desired nucleic acid sequences can be produced by de novo solid-phase DNA synthesis, by polymerase chain reaction (PCR), or by mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce a subject antibody. See Winnacker, From Genes to Clones, VCH Publishers, N.Y., N.Y. (1987). Suitable mammalian host cells include CHO cell lines, various COS cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The present disclosure provides compositions, including pharmaceutical compositions, comprising a subject antibody. In general, a composition comprises an effective amount of a subject antibody. An "effective amount" means a dosage sufficient to produce a desired result, e.g., reduction in cancer cell number, tumor size, etc., amelioration of a symptom of cancer or a fibrotic disease. Generally, the desired result is at least a reduction in a symptom of cancer or a fibrotic disorder, as compared to a control. A subject antibody can be delivered in such a manner as to avoid the blood-brain barrier, as described in more detail below. A subject antibody can be formulated and/or modified to enable the antibody to cross the blood-brain barrier.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying it in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose: and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject antibody (ies). Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject LOXL2 binding agent calculated in an amount sufficient to produce the desired effect in association with a pharmaceutically acceptable diluent, carrier or vehicle. The specifications for a subject LOXL2 binding agent may depend on the particular LOXL2 binding agent employed and the effect to be achieved, and the pharmacodynamics associated with each antibody in the host.

Other modes of administration will also find use in a subject method. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(–)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release can be taken to mean any one of a number of extended release dosage forms. The following terms may be considered to be substantially equivalent to controlled release: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated for use include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By "treatment" is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer, and pain associated therewith. As such, treatment also includes situations in which the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans: and non-human primates such as chimpanzees and monkeys). In some embodiments, the hosts will be humans.

Treatment Methods

The present disclosure further provides compositions, kits, methods for preventing and treating diseases associated with angiogenesis, fibrosis, tumors and metastasis.

In one embodiment, methods are provided for treating or preventing tumor invasion or metastasis in a subject in vivo, comprising administering to the subject an effective amount of a subject antibody.

In another embodiment, methods are provided for reducing tumor growth in a subject in vivo, comprising administering to the subject an effective amount of a subject antibody such that the tumor growth is reduced by at least 25%, 50%, 75%, 90%, or 95%. According to some embodiments, the tumor may be metastatic tumor.

In yet another embodiment, methods are provided for increasing or enhancing the chances of survival of a subject with metastatic tumor, comprising administering to a subject in need thereof an effective amount of a subject antibody, thereby increasing or enhancing the chances of survival of the subject treated by a certain period of time. In some embodiments, the survival of the subject is increased by at least 10 days, 1 month, 3 months, 6 months, 1 year, 1.5 years, 2 years, 3 years, 4 years, 5 years, 8 years, or 10 years.

Compositions may be administered to a patient (e.g., a mammal such as a human or a non-human animal such as a primate, rodent, cow, horse, pig, sheep, etc.) in therapeutically effective amounts which are effective for producing a desired therapeutic effect by inhibiting a disease or disorder such as those described herein, at a reasonable benefit/risk ratio applicable to any medical treatment. For human administration of the present compositions, the compositions may be formulated using methodology known by one of ordinary skill in the art. A therapeutically effective amount is an amount that achieves at least partially a desired therapeutic or prophylactic effect in an organ or tissue. In one example, the amount of a subject antibody necessary to bring about prevention and/or therapeutic treatment of a disease or disorder is not fixed per se. The amount of a subject antibody administered will vary with the type of disease or disorder, extensiveness of the disease or disorder, and size of the mammal suffering from the disease or disorder.

A response is achieved when the patient experiences partial or total alleviation, or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month, about at least 2 months, about at least 3 months, about at least 4 months, about at least 6 months, about at least 1 year, about at least 2 years, about at least 3 years, or more. Overall survival may also be measured in months to years. The patient's symptoms may remain static or may decrease.

The pharmaceutical formulations described herein may be used for the prevention or treatment of a wide variety of diseases which have collagen cross-linking or increased fibrosis as one part of their etiology. For example, the indication for the composition can also include fibrosis. Fibrosis is the abnormal accumulation of fibrous tissue that can occur as a part of the wound-healing process in damaged tissue. Such tissue damage may result from physical injury, inflammation, infection, exposure to toxins, and other causes.

Combination Therapy

A subject antibody can be administered alone (e.g., as monotherapy) to an individual in need thereof. However, a subject antibody can also be administered in combination therapy with one or more additional therapeutic agents. Suitable therapeutic agents include, e.g., chemotherapeutic agents, anti-neoplastic biologics, anti-angiogenic agents, and anti-fibrotic agents, to prevent or treat these diseases or conditions.

A subject antibody can, in some embodiments, slow or halt the progression of the epithelial-mesenchymal transition (EMT) in tumor cells, or induce a mesenchymal-epithelial transition (MET) to a less tumorigenic state, thereby rendering the tumor or diseased cells more susceptible to chemotherapeutic drugs, anti-neoplastic biologics, anti-angiogenic agents, and anti-fibrotic agents. A synergistic combination of a subject antibody with another therapeutic agent is useful for preventing or inhibiting tumor invasion and metastasis, inhibiting growth of primary tumors by sensitizing the tumor cells to the cytotoxic effects of the therapeutic agent, and also for efficaciously prevention or treatment of cancer.

As used herein the term "chemotherapeutic agent" or "chemotherapeutic" (or "chemotherapy", in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (e.g., bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phi11, see, e.g., Agnew, Chem. Intl. Ed. Engl., 33: 183-186 (1994); dynemicin, including dynemicin A: bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubincin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimeterxate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiadrenals such as aminoglutethimide, mitotane, trilostane; folic acid replinisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine): urethane; vindesine; dacarbazine; mannomustine; mitobronitol; mitolactol; pipobroman; gacytosine; cytosine arabinoside ("Ara-C"); cyclophosphamide; thiopeta; taxoids, e.g. paclitaxel (TAXOL™, Bristol Meyers Squibb Oncology, Princeton, N.J.) and docetaxel (TAXOTERE™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

In some embodiments, the anti-neoplastic agent in combination with a subject antibody is a tyrosine kinase inhibitor. For example, ZD1839 (Iressa™ of AstraZeneca K.K.) shows a competitive effect for ATP in ATP binding site of EGFR (epidermal growth factor receptor) tyrosine kinase, and inhibits tyrosine kinase activity by inhibiting autophosphorylation of tyrosine kinase.

As a result, the anticancer effect is expressed by blocking an EGFR-equipping signal transduction (ligands such as epidermal growth factor (EGF) are bound to the extracellular domain of EGFR, followed by activation of EGFR tyrosine kinase in the intracellular domain, causing not only autophosphorylation of EGFR but also phosphorylation of various intracellular target proteins, then transducing the proliferation signals from the cancer cell surface to nucleus, resulting in proliferation, infiltration, metastasis, and angiogenesis of cancer cells.

IMC-C225 or cetuximab (Erbitux™) which is an EGFR-targeting monoclonal antibody) recognizes the receptor part of EGFR on a cell membrane surface and inhibits the autophosphorylation of EGFR thereby inhibiting the tyrosine kinase activity. Herceptin, a monoclonal antibody against Her2/Neu which is homologous to EGFR, and imatinib mesylate (GLEEVEC™, formerly STI-571) can inhibit both tyrosine kinase activities of BCR-Abl and c-kit. Sorafenib (Nexavar™) is a small molecular inhibitor of Raf kinase, PDGF (platelet-derived growth factor), VEGF receptor 2 & 3 kinases and c-Kit.

As used herein, monoclonal antibodies against tumor antigens are antibodies elicited against antigens expressed by tumors and leukemic cells, for example, tumor-specific antigens. The monoclonal antibody also includes fully human and humanized antibody.

Other examples of therapeutic antibodies for cancer therapy include Trastuzumab (HERCEPTIN™; Overexpression of HER2 protein is associated with more aggressive disease and poorer prognosis in the clinic); Rituximab (RITUXAN™) that is raised against CD20 on lymphoma cells and selectively deplete normal and maligant CD20$^+$ pre-B and mature B cells; Alemtuzumab (CAMPATH™), a monoclonal antibody that specifically targets CD52 antigen that is found on B and T lymphocytes and used for the treatment of chronic lymphocytic leukemia (CLL) and lymphoma; and Gemtuzumab zogamicin (MYLOTARG™), an antibody conjugate that combines a specific antibody against CD33 with a chemotherapeutic drug (zogamicin) and is indicated for the treatment of relapsed adult acute myelocytic leukemia.

In another embodiment, anti-angiogenic agent is combined with a subject antibody to treat cancer and other diseases associated with abnormal or undesirable angiogenesis. Examples of anti-angiogenic agents include, but are not limited to, retinoid acid and derivatives thereof, 2-methoxyestradiol, ANGIOSTATIN™, ENDOSTATIN™, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide Peptidoglycan complex (sp-pg), staurosporine, modulators of matrix metabolism, including for example, proline analogs ((1-azetidine-2-carboxylic acid (LACA), cishydroxyproline, d,I-3, 4-dehydroproline, thiaproline, α-dipyridyl, β-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, β-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, for example, monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) *Nature Medicine* 5:1359-1364. Other anti-angiogenesis agents may include inhibitors of VEGF transcription.

Diagnostic Methods

A subject antibody is useful for detecting a pre-cancerous cell or a cancer cell. Thus, the present disclosure provides diagnostic methods, involving contacting a biological sample, obtained from an individual being tested, with a subject anti-LOXL2 antibody; and detecting binding of the anti-LOXL2 antibody to an epitope in the biological sample. The biological sample can be a tissue; a liquid sample that includes cells; or an acellular sample. A subject detection method detects the presence and/or levels of LOXL2 in a biological sample. A detected level of LOXL2 polypeptide that is higher than a normal, control value, indicates a cancerous or pre-cancerous state (e.g., indicates the presence, in a biological sample that includes cells, of a cancerous or pre-cancerous cell). In some embodiments, the anti-LOXL2 antibody is detectably labeled. In some embodiments, the anti-LOXL2 antibody is immobilized on an insoluble support (e.g., a test strip, a bead, the well of a multi-well plate, etc.).

In some embodiments, a subject diagnostic method detects a cell that is undergoing or that is about to undergo an epithelial-to-mesenchymal transition. Epithelial-to-Mesenchymal Transition (EMT) refers to the process whereby a cell with a gene expression/phenotype characteristic of epithelial cell (i.e., expressing specific proteins, factors, and molecules) changes or alters the genes or their level of expression which results in a change in the phenotype of the cell as exhibited by the alteration or change in the genes expressed. EMT can include loss of contact inhibition, altered growth control, and/or enhanced invasiveness (Christiansen and Rajasekaran, Cancer Res., 66(17): 8319-8326 (2006); and Thiery et al., Curr. Opin. Cell. Biol., 15: 740-6 (2003)). Molecular and morphologic features indicative of EMT correlate with poor histologic differentiation, destruction of tissue integrity, and metastasis. EMT provides mechanisms for epithelial cells to overcome the physical constraints imposed on them by intercellular junctions and adopt a motile phenotype (Burdsal et al. Development, 118:829-44 (1993); and Nieto et al., Mech, Dev., 105:27-35 (2001)).

Commonly used molecular markers for EMT include increased expression of N-cadherin and vimentin, nuclear localization of β-catenin, and increased production of the transcription factors such as Snail1 (Snail), Snail2 (Slug), Twist, EF1/ZEB1, SIP1/ZEB2, and/or E47 that inhibit E-cadherin production. Phenotypic markers for an EMT include, but are not limited to, an increased capacity for migration and three-dimensional invasion, as well as resistance to apoptosis. These markers have further been correlated with induction of EMT and an association with cancerous phenotypes. A subject diagnostic method will in some embodiments involve, in addition to detecting a LOXL2 polypeptide, detecting one or more of Snail1 (Snail), Snail2 (Slug), Twist, EF1/ZEB1, SIP1/ZEB2, and E47.

The occurrence of EMT during tumor progression allows tumor cells to acquire the capacity to infiltrate surrounding tissue and ultimately to metastasize to distant sites. Changes in gene expression within tumor cells can indicate a progression from epithelial or epithelial-like gene expression pattern to a mesenchymal or mesenchymal-like gene expression pattern. By way of example, the identification of loss of E-cadherin is correlated with metastatic carcinoma as well as resistance to cancer therapies such as EGFR inhibitors and IGF-R1 inhibitors. Analysis of many different types of cancer reveals that circulating tumor cells, or those found as micrometastases, evidence mesenchymal conversion based on changes of expression in a set of markers. These markers include, but are not limited to, EGFR, E-cadherin, ErbB3, RAB25, integrin beta 6, cadherin-2, fibroblast growth factor binding protein 1, distal-less homeo box 1, ZEB1 (transcription factor 8) SIP1, and vimentin. A subject diagnostic method will in some embodiments involve, in addition to detecting a LOXL2 polypeptide, detecting one or more of EGFR, E-cadherin, ErbB3, RAB25, integrin beta 6, cadherin-2, fibroblast growth factor binding protein 1, distal-less homeo box 1, ZEB1 (transcription factor 8) SIP1, and vimentin.

A subject diagnostic method will in some embodiments involve, in addition to detecting a LOXL2 polypeptide, detecting one or more of EGFR, E-cadherin, ErbB3, RAB25, integrin beta 6, cadherin-2, fibroblast growth factor binding protein 1, distal-less homeo box 1, ZEB1 (transcription factor 8) SIP1, vimentin, Snail1 (Snail), Snail2 (Slug), Twist, EF1/ZEB1, SIP1/ZEB2, and E47.

For assessment of tumor cell epithelial or mesenchymal biomarker expression, patient samples containing tumor cells, or proteins or nucleic acids produced by these tumor cells, can be used in methods described, for example, in U.S. patent application Publication Number 20070065858. Briefly, the level of expression of the biomarker can be assessed by assessing the amount (e.g., absolute amount or concentration) of the marker in a tumor cell sample, e.g., a tumor biopsy obtained from a patient, or other patient sample containing material derived from the tumor (e.g., blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies can also be subjected to post-collection preparative and storage techniques, e.g., fixation.

LOXL2 can be detected using a subject antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin), or an antibody fragment (e.g., a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

When a plurality of biomarkers (e.g., LOXL2 and one or more of the aforementioned biomarkers) is detected using a subject method, the level of each biomarker in a biological sample can be compared with a normal, control value, e.g., a normal level of each of the plurality of biomarkers in non-cancerous samples of the same type, either in a single reaction mixture (i.e., using reagents, such as different fluorescent probes, for each biomarker) or in individual reaction mixtures corresponding to one or more of the biomarkers.

The level of expression of a biomarker in normal (i.e., non-cancerous) human tissue can be assessed in a variety of ways. This normal level of expression can be assessed by assessing the level of expression of the biomarker in a portion of cells which appears to be non-cancerous, and then comparing the normal level of expression with the level of expression in a portion of the tumor cells. As further information becomes available as a result of routine performance of the methods described herein, population-average values for normal expression of the biomarkers can be used. Alternatively, the normal level of expression of a biomarker can be determined by assessing expression of the biomarker in a patient sample obtained from a non-cancer-afflicted patient, from a patient sample obtained from a patient before the suspected onset of cancer in the patient, from archived patient samples, and the like.

In general, a subject diagnostic method involves contacting a biological sample that may contain a biomarker (e.g., a LOXL2 polypeptide), with a subject anti-LOXL2 antibody, under appropriate conditions and for a time sufficient to allow the LOXL2 polypeptide (if present) and the antibody to interact and bind, thus forming a complex that can be removed and/or detected. Detection of binding between a LOXL2 polypeptide that may be present in a biological sample and a subject anti-LOXL2 antibody can be conducted in a variety of ways.

For example, one method to conduct such an assay involves anchoring the biomarker or anti-LOXL2 antibody onto a solid phase support, also referred to as a substrate, and detecting target biomarker/anti-LOXL2 antibody complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the anti-LOXL2 antibody can be anchored to a solid phase and a sample from a subject can be allowed to react as an unanchored component of the assay.

There are several established methods for anchoring assay components to a solid phase. These include, without limitation, biomarker or anti-LOXL2 antibody which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored. Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, and magnetite. In order to conduct assays with the above mentioned approaches, the non-immobilized component is added to the solid phase upon which the second component is anchored. After the reaction is complete, uncomplexed components can be removed (e.g., by washing) under conditions such that any complexes formed will remain immobilized upon the solid phase. The detection of LOXL2/anti-LOXL2 antibody complexes anchored to the solid phase can be accomplished in a number of methods outlined herein. In one embodiment, the anti-LOXL2 antibody, when it is the unanchored assay component, can be labeled for the purpose of detection and readout of the assay, either directly or indirectly, with detectable labels discussed herein and which are well-known to one skilled in the art.

As noted above, in some embodiments, a subject diagnostic method involves use of a subject anti-LOXL2 antibody that is detectably labeled. The term "labeled," with regard to a subject antibody, is intended to encompass direct labeling of the antibody by coupling (i.e., physically linking) a detectable substance to the antibody, as well as indirect labeling of the antibody by reactivity with another reagent that is directly labeled. Examples of indirect labeling include detection of a primary antibody using a fluorescently labeled secondary antibody.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a subject anti-LOXL2 antibody. Examples of such formats include, but are not limited to, enzyme immunoassay (EIA), radioimmunoassay (RIA), Western blot analysis and enzyme linked immunosorbent assay (ELISA). A skilled artisan can readily adapt known protein/antibody detection methods for use in determining whether tumor cells express a particular biomarker (e.g., a LOXL2 polypeptide).

In one format, antibodies, or antibody fragments or derivatives, can be used in methods such as Western blots or immunofluorescence techniques to detect the expressed proteins. In such uses, either the antibody or proteins can be immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. One skilled in the art will know many other suitable carriers for binding antibody or antigen, and will be able to adapt such support for use with a subject method. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin B12, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional cross-linking, and heterobifunctional cross-linking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional cross-linkers, including the bifunctional imidoesters and bifunctional N-hydroxysuccinimide esters, are commercially available and are employed for coupling amine groups on one substance to amine groups on another. Heterobifunctional cross-linkers are reagents which possess different functional groups. The most common commercially available heterobifunctional cross-linkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$. The term "detectably-labeled" refers to a molecule labeled in such a way that it can be readily detected by the intrinsic enzymatic activity of the label or by the binding to the label of another component, which can itself be readily detected.

Enzymes suitable for use include, but are not limited to, horseradish peroxidase, alkaline phosphatase, β-galactosidase, glucose oxidase, luciferases (including firefly and renilla luciferases), β-lactamase, urease, green fluorescent protein (GFP), red fluorescent protein, yellow fluorescent protein, and lysozyme. Enzyme labeling is facilitated by using dialdehyde, carbodiimide coupling, homobifunctional cross-linkers and heterobifunctional cross-linkers as described above for coupling an antibody with a member of a specific binding pair.

The labeling method chosen depends on the functional groups available on the enzyme and the material to be labeled, and the tolerance of both to the conjugation conditions. The labeling method used in a subject method can be one of, but not limited to, any conventional methods currently employed including those described by Engvall and Pearlmann, Immunochemistry 8, 871 (1971), Avrameas and Temynck. Immunochemistry 8, 1175 (1975), Ishikawa et al., J. Immunoassay 4(3):209-327 (1983) and Jablonski; Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, a subject antibody can be detectably labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above. Thus, in one embodiment, biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used for chromogenic detection.

In one immunoassay format for practicing a subject method, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g., aminated or carboxylated polystyrene, polyacrylamides, polyamides, polyvinylchloride, glass beads, agarose, or nitrocellulose.

Subjects Suitable for Treatment and/or Diagnosis

Subjects suitable for treatment with a subject method of treating cancer (e.g., a subject method of reducing tumor growth and/or metastasis) include individuals who have been diagnosed as having a cancer; individuals who have been treated for cancer with a treatment regimen other than a subject treatment regimen, and who have relapsed; and individuals who have failed treatment for cancer with a treatment regimen other than a subject treatment regimen, e.g., failed to respond to treatment with a treatment regimen other than a subject treatment regimen.

Subjects suitable for treatment with a subject method of treating a fibrotic disorder include individuals who have been diagnosed as having a fibrotic disorder; individuals who have been treated for a fibrotic disorder with a treatment regimen other than a subject treatment regimen, and who have relapsed; and individuals who have failed treatment for a fibrotic disorder with a treatment regimen other than a subject treatment regimen, e.g., failed to respond to treatment with a treatment regimen other than a subject treatment regimen.

Subjects suitable as subjects of a diagnostic assay as described herein include individuals who are being tested for the presence of a cancerous or a pre-cancerous cell; individuals who have been treated for cancer, and who are being monitored for the presence of a cancerous or pre-cancerous cell following treatment, e.g., to monitor efficacy of treatment; and individuals who have been treated for cancer, who are in remission for the cancer, and who are being monitored for the presence of a cancerous or pre-cancerous cell following remission.

Kits

The present disclosure provides a kit for carrying out a subject treatment or a subject diagnostic method.

A subject kit includes a subject antibody; and can include one or more additional reagents. The subject antibody in a subject kit can be humanized. A subject kit can include reagents for labeling the antibody. In some embodiments, the antibody in a subject kit comprises a detectable label. In some embodiments, the antibody in a subject kit is lyophilized.

In some embodiments, the antibody in a subject kit is present in a composition comprising: a) the antibody; and b) a pharmaceutically acceptable excipient. In some embodiments, e.g., where the kit is for use in a subject treatment method, the composition comprising a subject antibody is free of pyrogens. Where a subject kit is to be used in a subject treatment method, the antibody can be present in a syringe. The antibody can be provided in a lyophilized state, and solubilized in an appropriate liquid (e.g., an aqueous solution, such as saline, phosphate-buffered saline, or other buffered aqueous solution) prior to use.

Where a subject kit is to be used in a diagnostic method, the antibody can be immobilized onto an insoluble support (e.g., a bead, a test strip, a well of a multi-well plate, etc.).

Other optional components of the kit include: a buffer; a protease inhibitor; a detectable label; etc. The various components of the kit may be present in separate containers or certain compatible components may be pre-combined into a single container, as desired.

In addition to the above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kbp, kilobase pair(s); bp, base pair(s); nt, nucleotide(s); i.m., intramuscular(ly); i.p., intraperitoneal(ly); s.c., subcutaneous(ly); and the like.

Example 1

Generation of Antibodies to Human LOXL2 Protein

Full-length human LOXL2 protein (amino acid sequence shown in FIG. 1), a processed fragment of LOXL2 resulting from in vivo cleavage between the SRCR2 and SRCR3 domains, and the LOXL2 catalytic domain were used as immunogens in a series of mouse immunizations. A $His_6$ purification tag was appended to the carboxy terminus of the proteins. A subcutaneous immunization was conducted using a mixture containing 50% full-length LOXL2 and 50% processed LOXL2 as immunogen (3 mg total protein) and alhydrogel ($Al(OH)_3$) as adjuvant (proB immunization). A footpad immunization was conducted using a mixture containing 90% full-length LOXL2 and 10% processed LOXL2 as immunogen (0.3 mg total protein) and TiterMax® (TiterMax®, Norcross, Ga.) as adjuvant (RPDS-1 immunization). A second footpad immunization used the LOXL2 catalytic domain (0.3 mg total protein, amino acids 546-774 of FIG. 1) as immunogen and TiterMax® as adjuvant (RPDS-2 immunization). Sera from mice testing positive for anti-LOXL2 antibody by ELISA were used for the generation of hybridoma libraries, from which single clones were obtained. Antibodies were purified from the clones and screened for LOXL2 binding using an ELISA assay, as described in Example 2.

Example 2

ELISA Assay for LOXL2-Binding Antibodies

Nunc Maxisorp™ plates (Thermo Fisher Scientific, Rochester, N.Y.) were coated overnight with 1 ug/mL of LOXL2 in borate buffer at 4° C. (100 ul per well). The following day the plates were washed three times with PBST (50 mM sodium phosphate, 140 mM sodium chloride, 0.05% tween-20, pH 7.4) and blocked with bovine serum albumin solution (5% BSA in 50 mM sodium phosphate, 140 mM sodium chloride pH 7.4, 200 uL per well) for one hour at ambient temperature. Plates were then washed three times with 300 ul of PBST, and dilutions (two-fold) of purified antibody from the hybridoma clones described in Example 1, in a volume of 100 ul, were added to the blocked plates and incubated at ambient temperature for one hour. Plates were washed 3 times with 300 ul PBST, and 100 ul of a 1:10,000 dilution of horseradish peroxidase-conjugated goat anti-mouse secondary antibody (Pierce, Rockford, Ill.), diluted in 0.5% BSA solution (0.5% BSA in 50 mM sodium phosphate, 140 mM sodium chloride pH 7.4), was added, followed by incubation at ambient temperature for one hour.

Plates were washed 3 times with 300 ul PBST, then developed, at ambient temperature, using 100 uL of 3,3',5,5'-Tetramethylbenzidine (TMB) until a moderate blue color had developed (i.e., to an optical density that did not exceed 1.0). Reactions were then quenched with the addition of 100 ul of 1M hydrochloric acid. Quantitation was carried out on a SpectraMax® M5 (Molecular Devices, Sunnyvale, Calif.) in absorption mode at 450 nm. Dissociation constants were determined by plotting the absorbance values versus the concentration of antibody and fitting the data to the equation shown below (where PL is equal to the absorbance value (proportional to concentration of bound antibody), L is the antibody concentration (mM), $B_{MAX}$ is the maximal binding (nM) and $K_D$ is the dissociation constant (nM):

$$[PL] = \frac{B_{MAX} * [L]}{K_D + [L]}$$

Antibodies having a IQ of 1 nM or less were judged to be LOXL2-binding antibodies. From the three immunizations described in Example 1, 72 hybridoma clones expressing LOXL2-binding antibodies were obtained. Antibodies were named using a prefix denoting the immunization from which they were obtained (proB, RPDS-1, or RPDS-2), the letter M (for "monoclonal") and a number. Antibody AB0023 corresponds to proBM64, AB0024 is a humanized derivative of AB0023. See co-owned US 2009/0053224. Antibody AB0030 corresponds to proBM20. See co-owned US 2009/0053224. Antibodies were characterized further with respect to their ability to inhibit LOXL2 enzymatic activity, as described in Example 3.

Some of the 72 antibodies (from the RPDS-1 and RPDS-2 immunizations) were also re-screened against a fragment of LOXL2 containing only the catalytic domain (FIG. 1, amino acids 546-774). Thirty-seven of these were found to bind within the catalytic domain. These included RPDS-1M1, RPDS-1M3, RPDS-1M8, RPDS-1M9, RPDS-1M11, RPDS-1M15, RPDS-1M17, RPDS-1M19, RPDS-1M20 (AB0030), RPDS-1M22, RPDS-1M24, RPDS-1M25, RPDS-1M27, RPDS-1M28, RPDS-1M29, RPDS-1M30, RPDS-1M31, RPDS-1M32, RPDS-2M1, RPDS-2M2, RPDS-2M3, RPDS-2M4, RPDS-2M5, RPDS-2M6, RPDS-2M7, RPDS-2M8, RPDS-2M9, RPDS-2M10, RPDS-2M11, RPDS-2M12, RPDS-2M13, RPDS-2M14, RPDS-2M15, RPDS-2M16, RPDS-2M17, RPDS-2M18, and RPDS-2M19.

Example 3

Assays for Antibodies that Inhibit LOXL2 Enzymatic Activity

The 72 LOXL2-binding antibodies, as identified in Example 2, were further screened for their ability to inhibit the enzymatic activity of LOXL2. Two inhibition assays were employed: one used diaminopentane (DAP) as a substrate; the other used collagen as a substrate. In both assays, enzymatic activity of LOXL2 was measured using an assay that couples production of hydrogen peroxide (liberated by LOXL2 upon deamination of substrate) to horseradish peroxidase-catalyzed conversion of Amplex® Red (Invitrogen, Carlsbad, Calif.) to resorufin (a fluorescent product).

In assays using DAP as substrate, substrate mixture contained 50 mM borate pH 8.0, 100 uM Amplex® Red reagent, $1 \times 10^{-4}$% antifoam 204, and 30 mM diaminopentane (DAP). Enzyme mixture contained 50 mM borate pH 8.0, 2 Units/mL horseradish peroxidase (HRP, Sigma, St. Louis Mo.), 50 nM LOXL2, and $1 \times 10^{-4}$% antifoam 204. In assays using collagen as substrate, the substrate mixture lacked DAP and contained 1 mg/ml type I collagen (BD Biosciences, San Jose, Calif.) and, in the enzyme mixture, the concentration of LOXL2 was increased to 100 nM. Collagen was polymerized according to the supplier's directions prior to use and kept on ice until added to the substrate mixture.

The enzymatic reaction was initiated by adding 50 ul of substrate mixture to 50 ul of enzyme mixture. Assays were conducted at 37° C. on a SpectraMax® M5 (Molecular Devices, Sunnyvale, Calif.) in kinetics mode with an excitation wavelength of 544 nm and an emission wavelength of 590 nm. Measurements were made at 30 second intervals for 1 hour at 37° C. The slope of the progress curve, expressed as relative fluorescence units (RFU) per second, was determined in the linear region.

To test for inhibition of LOXL2 activity by LOXL2-binding antibodies, a dilution series of each of the 72 antibodies identified in Example 2 was incubated with LOXL2, in 50 ul of enzyme mixture, at ambient temperature, for one hour, and then the reaction was initiated with the addition of 50 μl of DAP substrate mixture, as described above. Data was collected as described above and the observed reaction rates, expressed as RFU/sec, were plotted as a function of antibody concentration.

$IC_{50}$ (the concentration of inhibitor that results in a 50% decrease in activity relative to no inhibitor) was determined by fitting these data to a four parameter fit, as shown in the equation below, in which y is the observed reaction rate (in RFU/sec), range is the reaction rate (RFU/sec) in the absence of antibody minus background rate (see below), s is the slope of the curve generated by plotting reaction rate versus antibody concentration, background is the reaction rate (RFU/sec) in the absence of enzyme and antibody, and x is the nanomolar concentration of antibody.

$$y = \frac{\text{Range}}{1 + \left(\frac{x}{IC50}\right)^s} + \text{background}$$

None of the antibodies were found to totally inhibit enzymatic activity. Consequently, each $IC_{50}$ value is an apparent $IC_{50}$ ($IC_{50}'$) based on the maximal inhibition observed with each antibody. Any antibody having an $IC_{50}'$ of 500 nM or less was scored, for the purposes of the present disclosure, as an inhibitor of LOXL2 activity.

Antibodies were first tested for inhibitory activity in an assay using DAP as substrate, and four inhibitory antibodies were identified (Table 2). The remaining antibodies were re-tested in an assay using collagen as substrate, as described above. Using the collagen substrate assay, four additional inhibitory antibodies were identified. In subsequent experiments, the four antibodies that were inhibitory in the DAP substrate assay were also found to inhibit when collagen was used as substrate.

By these criteria, eight out of the 72 LOXL2-binding antibodies identified in Example 2 were determined to be LOXL2 inhibitors. The names, and apparent $IC_{50}$ values, for each of these antibodies are presented in Table 2.

Additional experiments showed that, of the antibodies that inhibited the enzymatic activity of LOXL2, the following bound in the catalytic domain: RPDS-2M2, RPDS-2M4, RPDS-1M19, RPDS-1M20(AB0030), RPDS-1M27, and RPDS-1M31. Antibodies AB0023 and RPDS1-M21 bound outside the catalytic domain.

TABLE 2

Inhibitory Antibodies

| Antibody | $IC_{50}'$(nM) | Substrate |
|---|---|---|
| AB0023 | 62 | DAP, collagen |
| RPDS2-M2 | 90 | DAP, collagen |
| RPDS-2M4 | 114 | DAP, collagen |
| AB0030 | 35 | collagen |
| RPDS-1M19 | 33 | collagen |
| RPDS-1M21 | 32 | DAP, collagen |
| RPDS-1M27 | 39 | collagen |
| RPDS-1M31 | 210 | collagen |

Inhibitory antibodies AB0030, RPDS-1M19, RPDS-1M21, RPDS-1M27, RPDS1-M31, RPDS-2M2 and RPDS-2M4 were deposited ed under the terms of the Budapest Treaty with the Bureau of Microbiology at Health Canada (BMHC, Winnipeg, Manitoba, Canada) on Mar. 26, 2010, as shown in Table 3.

TABLE 3

| Material Deposited | Date of Deposit | Accession Number |
|---|---|---|
| RPDS1-M20 (AB0030) | Mar. 26, 2010 | 050210-04 |
| RPDS-1M19 | Mar. 26, 2010 | 050210-02 |
| RPDS-1M21 | Mar. 26, 2010 | 050210-03 |
| RPDS-1M27 | Mar. 26, 2010 | 050210-01 |
| RPDS1-M31 | Mar. 26, 2010 | 260310-01 |
| RPDS-2M2 | Mar. 26, 2010 | 260310-02 |
| RPDS-2M4 | Mar. 26, 2010 | 260310-03 |

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by the BMHC under the terms of the Budapest Treaty, and subject to an agreement between the BMHC and the assignee(s) of the present application which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee(s) of the present application has agreed that if a culture of the materials on deposit should die or be lost or destroyed when cultivated under suitable conditions, the materials will be promptly replaced, on notification, with another culture of the same. Availability of the deposited material is not to be construed as a license to practice the invention in contravention of the rights granted under the authority of any government in accordance with its patent laws.

Example 4

Further Screening of Antibodies to Human LOXL2

Antibodies that bound to full-length LOXL2, but not to the fragment containing the LOXL2 catalytic domain, were further characterized to determine where, outside the catalytic domain, their epitopes were located. To this end, ELISA assays were conducted using, as targets, polypeptides corresponding to the different SRCR domains of LOXL2 and their intervening linker sequences. The portions of the LOXL2 amino acid sequence (as shown in FIG. 1) contained in each polypeptide, and the names of the polypeptides, are shown in the second and first columns, respectively, of Table 4. The amino acid sequences of the polypeptides are shown in FIG. 2.

For these assays, Nunc plates were coated with 100 ul of a 1 ug/ml solution of the particular polypeptide used as target, in 50 mM sodium borate pH 8, overnight at 4° C. Plates were washed three times with 300 ul of PBST, then 200 ul of 5% BSA in PBS was added to each well and plates were incubated at ambient temperature for 1 hour with gentle rocking. Plates were then washed again, three times with 300 ul of PBST per well, then antibody (100 ul in PBST) was added to the wells. Antibodies were assayed either at a fixed concentration of 100 nM or in a twelve-point dilution series diluting down in two-fold increments from 10 nM (100 ul per well or per dilution). After addition of antibody solution, plates were incubated for 1 hour at ambient temperature with gentle rocking. Plates were then washed three times with the addition of 300 ul of PBST per well. An HRP-conjugated goat anti-mouse secondary antibody (Pierce, Rockford, Ill.) was diluted 10,000-fold in 0.5% BSA in PBS; 100 ul of this solution was added to each well and plates were incubated at ambient temperature for 1 hour. Plates were washed three times with 300 ul of PBST per well. Plates were then developed by addition of 100 ul of TMB per well, and the reaction was quenched, after a moderate blue color (<OD) was observed, by addition of 100 ul of 1N HCl. Color was quantitated on a SpetcraMax® M5 (Molecular Devices, Sunnyvale, Calif.) by measuring absorbance at 450 nm.

An antibody was scored as binding to a polypeptide if absorbance values as a function of antibody concentration yielded a dose-dependent increase in signal. For antibodies that were tested at a single concentration, an absorbance value of at least 0.5 OD units above that obtained in a well not containing antibody was required for the antibody to be scored as positive for binding.

The results of this analysis are shown in Table 4. One antibody (RPDS-1M7) was shown to bind within the SRCR1 domain, but this antibody was found not to be inhibitory (see Example 3). No antibodies were obtained that bound to the SRCR2 region. Out of seven antibodies that bound to the SRCR3 region (RPDS-1M2, RPDS-1M4, RPDS-1M5, RPDS-1M 10. RPDS-1M13, RPDS-1M18, RPDS1-1M26), none were found to be inhibitory (see Example 3). One antibody (RPDS-1-M21) was shown to bind in the sequence between SRCR3 and SRCR4 (the SRCR3/4 "linker") and was determined to be inhibitory (see Example 3, Table 2). Of two antibodies (RPDS-1M14, AB0023) that bound in the SRCR4 region, one (AB0023) was found to be inhibitory (see Example 3, Table 2).

TABLE 4

| LOXL2 Fragment | Amino Acids | Antibodies bound |
|---|---|---|
| 1A | 1-159 | RPDS-1M7 |
| 1B | 58-187 | RPDS-1M7 |
| 1C | 1-187 | RPDS-1M7 |
| 2A | 160-302 | NONE |
| 2B | 188-324 | NONE |
| 2C | 160-324 | NONE |
| 3A | 303-425 | NONE |
| 3B | 325-434 | RPDS-1M2, RPDS-1M4, RPDS-1M5, RPDS-1M10, RPDS-1M13, RPDS-1M18, RPDS-1M21, RPDS-1M26 |
| 3C | 303-434 | RPDS-1M2, RPDS-1M4, RPDS-1M5, RPDS-1M10, RPDS-1M13, RPDS-1M18, RPDS-1M21, RPDS-1M26 |
| 4A | 426-547 | RPDS-1M14, RPDS-1M21, AB0023, AB0024 |
| 4B | 435-547 | RPDS-1M14, AB0023, AB0024 |

These results show that inhibitory antibodies can bind in the linker sequence between SRCR3 and SRCR4 (RPDS-1M21) and in the SRCR4 domain (AB0023). Additional experiments, discussed above, showed that inhibitory antibodies can also bind in the catalytic domain (RPDS-2M2, RPDS-2M4, RPDS-1M19, RPDS-1M20(AB0030), RPDS-1M27, and RPDS-1M31).

Example 5

Peptide Mapping

Peptides corresponding to overlapping 15-amino acid stretches of SRCR3 and SRCR4 from LOXL2 were synthesized (Elim Biopharmaceuticals, Hayward, Calif.) and assayed for their ability to bind to AB0023 and its humanized derivative AB0024. The amino acid sequences of the peptides are shown in Table 5. Lyophilized peptides were dissolved, to a final concentration of 10 mM, in PBS+5% acetonitrile. Stock solutions of antibodies, at 2 mg/ml, were made in PBS (AB0023) or 10 mM Na phosphate, 140 mM NaCl (AB0024). Six microliters of peptide solution was added to 496 ul of antibody solution, and the final volume was brought to 1 ml (with PBS for AB0023 or 10 mM Na phosphate for AB0024) to give final concentrations of 60 uM peptide and 6.6 uM antibody, and incubated at 25° C. for 1 hour at room temperature. Samples were then injected onto an Agilent 1100 SEC-HPLC column (Tosoh TSKgel G3000SWx resin). Columns were developed with PBS+250 mM NaCl, pH 7.4 (AB0023) or 10 mM Na phosphate, 250 mM NaCl, pH 5.8 (AB0024); at a rate of 0.5 ml/min, and peak areas of UV-absorbing material (210 nm) were measured. Because the molecular weight of the 15-mer peptides was small compared to the molecular weight of the antibodies, formation of an antibody-peptide complex did not result in a shift in the retention time of either molecule. Consequently, formation of antibody-peptide complexes was indicated by an increase in the area of the peak corresponding to free antibody, along with a concurrent decrease in the area of the peak corresponding to free peptide. ChemStation software (Agilent, Palo Alto, Calif.) was used for integration of peak areas.

The results of this analysis (summarized in right-most column of Table 5) showed that peptides 3, 4 and 5 were able to bind AB0023. Although not shown in the Table, the same three peptides were also shown to be bound by AB0024. These peptides define a 39-amino acid functional epitope, within the SRCR4 domain of LOXL2, having the following amino acid sequence:

(SEQ ID NO: 3)
VWGMVCGQNWGIVEAMVVCRQLGLGFASNAFQETWYWHG

TABLE 5

Peptide mapping

| Peptides | Sequence | SEQ ID NO | AB0023 Binding |
|---|---|---|---|
| 1 | LRLNGGRNPYEGRVE | 25 | − |
| 2 | RVEVLVERNGSLVWG | 26 | − |
| 3 | VWGMVCGQNWGIVEA | 27 | + |
| 4 | VEAMVVCRQLGLGFA | 28 | + |
| 5 | GFASNAFQETWYWHG | 29 | + |
| 6 | WHGDVNSNKVVMSGV | 30 | − |
| 7 | SGVKCSGTELSLAHC | 31 | − |
| 8 | AHCRHDGEDVACPQG | 32 | − |
| 9 | PQGGVQYGAGVACSE | 33 | − |
| 10 | CSETAPDLVLNAEMV | 34 | − |

Legend to Table 5: Amino acids sequences of the peptides (in one-letter code) are given in the second column. In the fourth column, "+" indicates that the peptide was bound by AB0023, "−" indicates that no binding was observed.

Example 6

Alanine Scanning Mutagenesis

Alanine scanning mutagenesis of the SRCR4 domain of LOXL2 was conducted to identify amino acid residues in the LOXL2 SRCR4 domain involved in the binding of the AB0023, AB0024 and M14 antibodies. To this end, a DNA fragment comprising sequences encoding the SRCR4 domain of LOXL2 (amino acids 435-547 of SEQ ID NO:1) was constructed; a signal sequence, linker sequences, a myc epitope tag and a $(His)_6$ purification tag were added, and the construct was cloned. Additional constructs were made such that certain amino acids in the SRCR4 domain were converted to alanine. The ability of AB0023, AB0024 and M14 to bind to the various mutant amino acid sequences was determined by ELISA, surface plasmon resonance (SPR) and SEC-HPLC for AB0023 and AB0024; and by ELISA for M14. ELISA assays were conducted exactly as described in Example 2, using the different alanine scanning mutants as targets.

For SPR analyses, the binding of antibodies to LOXL2 SRCR4 alanine scanning mutant constructs was determined using a ProteOn XPR36 instrument (Bio-Rad, Hercules, Calif.). Proteins were immobilized to a GLC sensor chip. The GLC sensor chip was activated with a 1:1 ratio mixture of 1-Ethyl-3-[3-dimethylaminopropyl]carbodiimide hydrochloride (EDC) and N-hydroxysulfosuccinimide (Sulfo-NHS), prepared according to the manufacturer's directions, passed over the chip at a flow rate of 30 μL/min for 300 seconds. Protein solution, at 1 μg/mL in acetate buffer pH 4.5, was then passed over the chip at a rate of 30 μL/min for 300 seconds, then unreacted sites on the chip were blocked with 1M ethanolamine passed over the chip at a flow rate of 30 μL/min for 300 seconds. A reference channel was created using the same procedure by flowing acetate buffer over the surface. Dilutions of purified antibodies were passed over the surface at a rate of 100 uL/min for 150 seconds, and a buffer control was included in the series. Sensograms were analyzed using the ProteOn manager software and data was fit to the Langmuir model within the software. The data represent the average and standard deviation of four separate experiments.

SEC-HPLC was conducted s described in Example 5, using the different alanine scanning mutants of SRCR4 in place of the 15-mer peptides.

Results obtained using these three different methods were consistent with one another, and Table 6 shows a compilation of the data.

TABLE 6

Alanine scanning mutagenesis

| Mutation | A0023 binding | AB0024 binding | M14 binding |
|---|---|---|---|
| N438A | + | + | + |
| G440A | + | + | ND |
| N442A | + | + | ND |
| Y444A | + | + | + |
| V450A | + | + | ND |
| R454A | + | + | ND |
| G456A | + | + | ND |
| L458A | + | + | + |
| W460A | + | + | ND |
| G465A | + | + | ND |
| N467A | + | + | ND |
| G469A | + | + | ND |
| V471A | + | + | ND |
| M474A | + | + | ND |
| V476A | +/− | +/− | ND |
| R478A | 0 | 0 | + |
| F484A | 0 | 0 | ND |
| S486A | + | + | ND |
| N487A | + | + | + |
| F489A | + | + | ND |
| Q490A | + | + | + |
| E491A | + | + | ND |
| T492A | + | + | ND |
| W493A | + | + | ND |
| Y494A | + | + | + |
| W495A | + | + | ND |
| H496A | + | + | ND |
| G497A | + | + | ND |
| K510A | + | + | + |
| S512A | + | + | + |

Legend to Table 6: Numbers in the first column refer to amino acid residues in the LOXL2 amino acid sequence shown in FIG. 1. The letter preceding the number represents the amino acid present at that position (in one-letter amino acid code) in the wild-type protein. The letter following the number indicates conversion of the wild-type residue to alanine in that particular mutant. The remaining columns indicate whether the particular mutant polypeptide was bound by AB0023 (second column), AB0024 (third column) or M14 (fourth column). M14 refers to the RPDS-1M14 antibody. "+" indicates binding, "+/−" indicates weak binding, "0" indicates binding not detectable, "ND" indicates "not done."

Example 7

AB0023 Binds Specifically to LOXL2

The lysyl oxidase-like proteins LOXL3 and LOXL4 also contain four SRCR domains, which have some homology to, but are not identical with, the four SRCR domains of LOXL2. To assess its specificity, and provide further information about the nature of its epitope, the binding of AB0023 to the LOXL3 and LOXL4 SRCR sequences was tested. ELISA assays were conducted exactly as described in Example 2, using human LOX, LOXL1, LOXL2, LOXL3 and LOXL4 as targets. Results, shown in FIG. 3, indicate that AB0023 does not bind to any of the other known human lysyl oxidase-type enzymes. Thus, AB0023 is specific to LOXL2, as compared to other lysyl oxidase-type enzymes and, in particular, AB0023 does not bind to the SRCR4 domains of either LOXL3 or LOXL4.

An alignment of the amino acid sequences of the SCRC4 domains from LOXL2, LOXL3 and LOXL4 is presented in FIG. 4. Differences in the amino acid sequence between the LOXL2 SRCR4 domain and the SRCR4 domains of LOXL3 and LOXL4 can be used for further definition of the epitope recognized by AB0023.

Example 8

M14 Binds to a Different Epitope than the One Bound by AB0023 and AB0024

Table 6 above shows that conversion of amino acid 478 of the LOXL2 SRCR4 domain from arginine to alanine abolished its ability to be bound by the AB0023 and AB0024 antibodies, but did not affect its ability to be bound by the M14 antibody. This suggests that M14 recognizes an epitope that is distinct from that recognized by AB0023 and AB0024. In separate experiments, it was determined, by surface plasmon resonance analysis as described in Example 6, that the F484A mutant, which also is not bound by AB0023, was bound by the M14 antibody. Thus, the M14 antibody defines a second epitope in the SRCR4 domain, distinct from that recognized by AB0023 and AB0024.

Example 9

AB0030 Epitope in Catalytic Domain

The AB0030 antibody binds in the catalytic domain of human LOXL2 and inhibits its enzymatic activity. ELISA assays comparing the binding of AB0030 to human. *Cynomolgus*, rat and mouse LOXL2 proteins showed that AB0023 also binds to *Cynomolgus* LOXL2, but not to rat or mouse LOXL2. When the amino acid sequences of the catalytic domains of human and *cynomolgus* LOXL2, on the one hand, and rat and mouse LOXL2, on the other, were compared, 21 residues were found to differ in sequence. See FIG. 5. Accordingly, variants of the rat protein, in which each of these amino acids was altered individually to correspond to the human sequence, were assayed, by ELISA and SPR, for their ability to be bound by AB0030.

The results of these analyses indicated that changes at two positions conferred AB0030-binding ability on the rat LOXL2 protein (indicated by asterisks in FIG. 5). These changes were conversion of mouse residue H595 to Y (corresponding to human Y593) and conversion of mouse residue Y741 to H (corresponding to human H739). Accordingly, these two residues constitute part of the epitope bound by AB0030.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated monoclonal antibody to lysyl oxidase-like-2 (LOXL2) that specifically binds to an epitope within amino acids 325 through 434 of the sequence set forth in SEQ ID NO:1, wherein the antibody does not compete for binding with antibody AB0023 or AB0024.

2. The antibody of claim 1, wherein the epitope comprises amino acids within the sequence TPAMGLQKK (SEQ ID NO:2).

3. The isolated antibody of claim 1, wherein the antibody inhibits enzymatic activity of a LOXL2 polypeptide.

4. The isolated antibody of claim 1, wherein the antibody does not inhibit enzymatic activity of a LOXL2 polypeptide.

5. The isolated antibody of claim 1, wherein the antibody binds the epitope with an affinity of from about $10^7$ $M^{-1}$ to about $10^{12}$ $M^{-1}$.

6. The isolated antibody of claim 1, wherein the antibody comprises a heavy chain, and wherein the heavy chain of the antibody is of the isotype IgG1, IgG2, IgG3, or IgG4.

7. The isolated antibody of claim 1, wherein the antibody is detectably labeled.

8. The isolated antibody of claim 1, wherein the antibody is a Fv, scFv, Fab, F(ab')2, or Fab'.

9. The isolated antibody of claim 1, wherein the antibody is humanized.

10. The isolated antibody of claim 1, wherein the antibody is chimeric.

11. The isolated antibody of claim 1, wherein the antibody comprises a covalently linked moiety selected from the group consisting of a non-peptide synthetic polymer, a lipid, a fatty acid, a polysaccharide, a carbohydrate, or a contrast agent.

12. The isolated antibody of claim 11, wherein the synthetic polymer is poly(ethylene glycol) polymer.

13. The isolated antibody of claim 1, wherein the antibody is immobilized on a solid support.

14. The isolated antibody of claim 1, wherein the antibody comprises a cancer chemotherapeutic agent covalently or non-covalently linked to the antibody.

15. A kit for treating a condition associated with LOXL2 comprising a composition comprising an isolated antibody of claim 1 and a pharmaceutically acceptable carrier or excipient.

16. The kit of claim 15, wherein said condition associated with LOXL2 is a tumor, a metastasis, angiogenesis, or fibrosis.

17. The kit of claim 15, wherein the antibody comprises a detectable label, a therapeutic agent or both.

18. An isolated monoclonal antibody to lysyl oxidase-like-2 (LOXL2) that specifically binds to a peptide consisting of amino acids 325 through 434 of the sequence set forth in SEQ ID NO:1, wherein the antibody does not compete for binding with antibody AB0023 or AB0024.

19. The antibody of claim 18, wherein the antibody specifically binds to an epitope comprising the sequence TPAMGLQKK (SEQ ID NO:2).

20. The isolated antibody of claim 18, wherein the antibody inhibits enzymatic activity of a LOXL2 polypeptide.

21. The isolated antibody of claim 18, wherein the antibody does not inhibit enzymatic activity of a LOXL2 polypeptide.

22. The isolated antibody of claim 18, wherein the antibody binds the epitope with an affinity of from about $10^7$ $M^{-1}$ to about $10^{12}$ $M^{-1}$.

23. The isolated antibody of claim 18, wherein the antibody comprises a heavy chain, and wherein the heavy chain of the antibody is of the isotype IgG1, IgG2, IgG3, or IgG4.

24. The isolated antibody of claim 18, wherein the antibody is detectably labeled.

25. The isolated antibody of claim 18, wherein the antibody is a Fv, scFv, Fab, F(ab')2, or Fab'.

26. The isolated antibody of claim 18, wherein the antibody is humanized.

27. The isolated antibody of claim 18, wherein the antibody is chimeric.

* * * * *